(12) United States Patent
Cassayre et al.

(10) Patent No.: US 9,307,766 B2
(45) Date of Patent: Apr. 12, 2016

(54) ISOXAZOLINE DERIVATIVES AS INSECTICIDAL COMPOUNDS

(75) Inventors: Jerome Yves Cassayre, Stein (CH); Peter Renold, Stein (CH); Thomas Pitterna, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/240,052

(22) PCT Filed: Aug. 24, 2012

(86) PCT No.: PCT/EP2012/066556
§ 371 (c)(1),
(2), (4) Date: Feb. 21, 2014

(87) PCT Pub. No.: WO2013/026933
PCT Pub. Date: Feb. 28, 2013

(65) Prior Publication Data
US 2014/0194376 A1 Jul. 10, 2014

(30) Foreign Application Priority Data

Aug. 25, 2011 (EP) .................................... 11178927

(51) Int. Cl.
| | | |
|---|---|---|
| A01N 43/80 | (2006.01) | |
| A01N 43/40 | (2006.01) | |
| C07D 413/14 | (2006.01) | |
| C07D 413/12 | (2006.01) | |
| A01N 37/42 | (2006.01) | |
| A01N 37/50 | (2006.01) | |
| A01N 43/42 | (2006.01) | |
| C07F 7/18 | (2006.01) | |
| A01N 43/20 | (2006.01) | |

(52) U.S. Cl.
CPC .............. *A01N 43/80* (2013.01); *A01N 37/42* (2013.01); *A01N 37/50* (2013.01); *A01N 43/20* (2013.01); *A01N 43/40* (2013.01); *A01N 43/42* (2013.01); *C07D 413/12* (2013.01); *C07D 413/14* (2013.01); *C07F 7/1856* (2013.01)

(58) Field of Classification Search
None
See application file for complete search history.

(56) References Cited

U.S. PATENT DOCUMENTS 8,686,014 B2 * 4/2014 Renold et al. ............... 514/378
8,822,502 B2 * 9/2014 Pitterna et al. ............. 514/340

FOREIGN PATENT DOCUMENTS

WO        2010020522         2/2010

OTHER PUBLICATIONS

International Search Report and Written Opinion dated Oct. 5, 2012 International Patent Application No. PCT/EP2012/066556.

* cited by examiner

*Primary Examiner* — Kamal Saeed
(74) *Attorney, Agent, or Firm* — Brian D. McAlhaney

(57) ABSTRACT

The present invention provides compounds of formula (I) wherein $G^1$ is oxygen; $R^1$ is hydrogen; $R^2$ is group (P) L is a bond, methylene or ethylene; one of $A^1$ and $A^2$ is S, SO or $SO_2$ and the other is $—C(R^4)R^4—$; $R^3$ is hydrogen or methyl; each $R^4$ is independently hydrogen or methyl; $Y^2$ and $Y^3$ are independently CH or nitrogen, wherein $Y^2$ and $Y^3$ are not both nitrogen; $X^2$ is $C—X^6$ or nitrogen; $X^1$, $X^3$ and $X^6$ are independently hydrogen, halogen or trihalomethyl, wherein at least two of $X^1$, $X^3$ and $X^6$ are not hydrogen; $X^4$ is trifluoromethyl, difluoromethyl or chlorodifluoromethyl. The invention also provides intermediates useful for the preparation of compounds of formula (I), as well as methods of controlling insects, acarines, nematodes or molluscs using the compounds of formula (I).

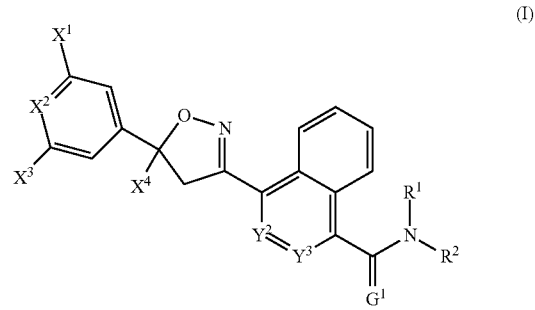

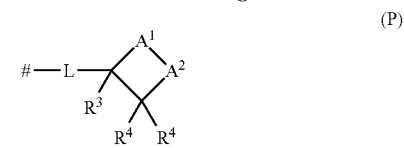

10 Claims, No Drawings

ISOXAZOLINE DERIVATIVES AS INSECTICIDAL COMPOUNDS

RELATED APPLICATION INFORMATION

This application is a 371 of International Application No. PCT/EP2012/066556, filed 24 Aug. 2012, which claims priority to EP Patent Application No. 11178927.7, filed 25 Aug. 2011, the contents of which are incorporated herein by reference herein.

The present invention relates to certain isoxazolines derivatives, to processes and intermediates for preparing these derivatives, to insecticidal, acaricidal, nematicidal and molluscicidal compositions comprising these derivatives and to methods of using these derivatives to control insect, acarine, nematode and mollusc pests. The present invention also relates to use of these compounds in the field of animal health.

Certain isoxazoline derivatives with insecticidal properties are disclosed, for example, in WO2010/025998.

There is an ongoing need to find compounds that exhibit higher levels of activity, broader spectrum of control, higher levels of activity against specific pests, increased safety, reduced impact on the environment. The present invention seeks to address these needs at least in part.

The present invention provides compounds of formula I

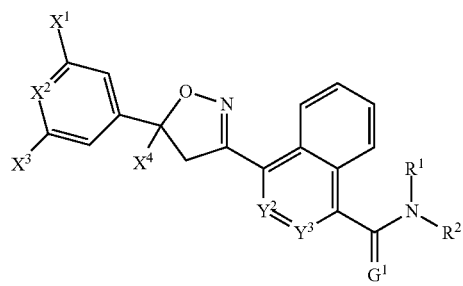

(I)

wherein
$G^1$ is oxygen;
$R^1$ is hydrogen;
$R^2$ is group P

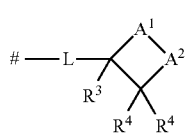

(P)

L is a bond, methylene or ethylene;
one of $A^1$ and $A^2$ is S, SO or $SO_2$ and the other is $-C(R^4)R^4-$;
$R^3$ is hydrogen or methyl;
each $R^4$ is independently hydrogen or methyl;
$Y^2$ and $Y^3$ are independently CH or nitrogen, wherein $Y^2$ and $Y^3$ are not both nitrogen;
$X^2$ is $C-X^6$ or nitrogen;
$X^1$, $X^3$ and $X^6$ are independently hydrogen, halogen or trihalomethyl, wherein at least two of $X^1$, $X^3$ and $X^6$ are not hydrogen;
$X^4$ is trifluoromethyl, difluoromethyl or chlorodifluoromethyl.

The compounds of formula (I) may exist in different geometric or optical isomers or tautomeric forms. This invention covers all such isomers and tautomers and mixtures thereof in all proportions as well as isotopic forms such as deuterated compounds. The invention also covers salts and N-oxides of the compounds of the invention.

The compounds of the invention may contain one or more asymmetric carbon atoms and may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, $-CH_2-$, $-CH_2-CH_2-$, $-CH(CH_3)-$, $-CH_2-CH_2-CH_2-$, $-CH(CH_3)-CH_2-$, or $-CH(CH_2CH_3)-$. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include isoxazolyl, thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $R^2$, $Y^2$, $Y^3$, $X^1$, $X^2$, $X^3$, $X^4$, $X^5$ and $X^6$ are, in any combination, as set out below.

Preferably $R^2$ is thietan-3-yl-, 1-oxo-thietan-3-yl-, 1,1-Dioxo-thietan-3-yl-, 2,2-dimethylthietan-3-yl-, 2,2-dimethyl-1-oxo-thietan-3-yl-, 2,2-dimethyl-1,1-Dioxo-thietan-3-yl-, 3-Methyl-thietan-3-yl-, 3-Methyl-1-oxo-thietan-3-yl-, 3-Methyl-1,1-Dioxo-thietan-3-yl-, thietan-3-ylmethyl-, 1-oxo-thietan-3-ylmethyl-, 1,1-Dioxo-thietan-3-ylmethyl-, thietan-2-ylmethyl-, (1-oxothietan-2-yl)methyl-, (1,1-dioxothietan-2-yl)methyl-, 2-(thietan-3-yl)ethanyl, 2-(1,1-dioxothietan-3-yl)ethanyl, or 2-(1-oxothietan-3-yl)ethanyl more preferably $R^2$ is 2-(thietan-3-yl)ethanyl, 2-(1,1-dioxothietan-3-yl)ethanyl, 2-(1-oxothietan-3-yl)ethanyl, thietan-3-ylmethyl-, 1-oxo-thietan-3-ylmethyl-, 1,1-Dioxo-thietan-3-ylmethyl-, thietan-3-yl-, 1-oxo-thietan-3-yl-, 1,1-Dioxo-thietan-3-yl-.

Preferably $Y^2$ is CH, $Y^3$ is CH, or $Y^2$ is N, $Y^3$ is CH, or $Y^2$ is CH, $Y^3$ is N.

Preferably $X^1$ is chloro, $X^2$ is CH, $X^3$ is chloro, or $X^1$ is chloro, $X^2$ is C—F, $X^3$ is hydrogen, or $X^1$ is fluoro, $X^2$ is C—Cl, $X^3$ is hydrogen, or $X^1$ is chloro, $X^2$ is C—Cl, $X^3$ is hydrogen, or $X^1$ is chloro, $X^2$ is C—Br, $X^3$ is chloro, or $X^1$ is chloro, $X^2$ is C—F, $X^3$ is chloro, or $X^1$ is chloro, $X^2$ is C—Cl, $X^3$ is chloro, or $X^1$ is chloro, $X^2$ is C—I, $X^3$ is chloro, or $X^1$ is fluoro, $X^2$ is C—F, $X^3$ is fluoro, or $X^1$ is chloro, $X^2$ is CH, $X^3$ is bromo, or $X^1$ is chloro, $X^2$ is CH, $X^3$ is fluoro, or $X^1$ is chloro, $X^2$ is CH, $X^3$ is trifluoromethyl, or $X^1$ is chloro, $X^2$ is C—Cl, $X^3$ is trifluoromethyl, or $X^1$ is trifluoromethyl, $X^2$ is CH, $X^3$ is trifluoromethyl, or $X^1$ is trifluoromethyl, $X^2$ is C—Cl, $X^3$ is trifluoromethyl, or $X^1$ is trifluoromethyl, $X^2$ is CH, $X^3$ is hydrogen, or $X^1$ is chloro, $X^2$ is N, $X^3$ is chloro, or $X^1$ is trifluoromethyl, $X^2$ is N, $X^3$ is trifluoromethyl.

The invention also relates to the following intermediates which are useful for the preparation of compounds of formula I:

Compounds of formula X1

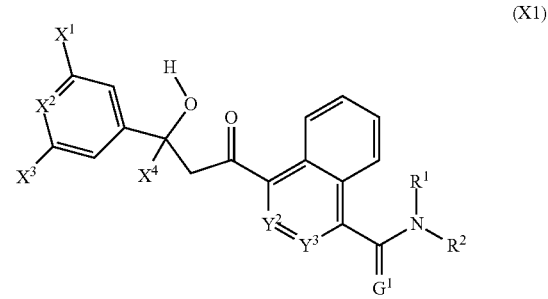

(X1)

wherein $G^1$, $R^1$, $R^2$, $X^1$, $X^2$, $X^3$, $X^4$, $Y^2$, and $Y^3$ are as defined for the compound of formula I. Preferred definitions of $G^1$, $R^1$, $R^2$, $X^1$, $X^2$, $X^3$, $X^4$, $Y^2$, and $Y^3$ are the same as for the corresponding substituents of compounds of formula I.

Compound of formula X2

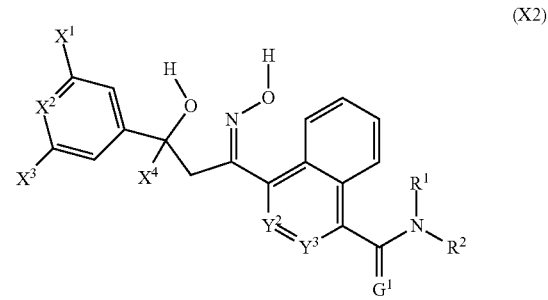

(X2)

wherein $G^1$, $R^1$, $R^2$, $X^1$, $X^2$, $X^3$, $X^4$, $Y^2$, and $Y^3$ are as defined for the compound of formula I. Preferred definitions of $G^1$, $R^1$, $R^2$, $X^1$, $X^2$, $X^3$, $X^4$, $Y^2$, and $Y^3$ are the same as for the corresponding substituents of compounds of formula I.

Compound of formula X3

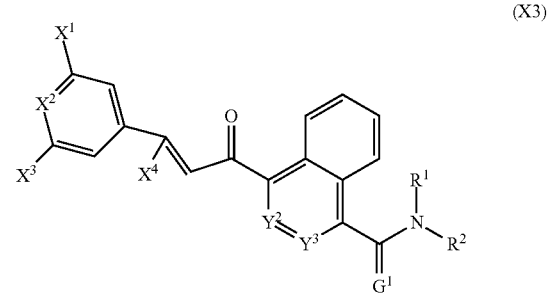

(X3)

wherein $G^1$, $R^1$, $R^2$, $X^1$, $X^2$, $X^3$, $X^4$, $Y^2$, and $Y^3$ are as defined for the compound of formula I. Preferred definitions of $G^1$, $R^1$, $R^2$, $X^1$, $X^2$, $X^3$, $X^4$, $Y^2$, and $Y^3$ are the same as for the corresponding substituents of compounds of formula I.

Compound of formula X4

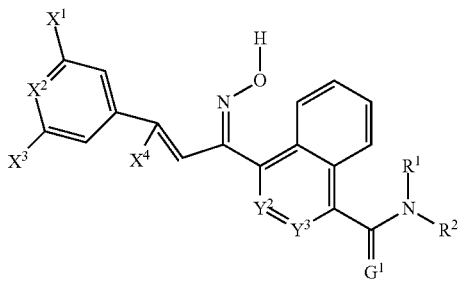

(X4)

wherein $G^1$, $R^1$, $R^2$, $X^1$, $X^2$, $X^3$, $X^4$, $Y^2$, and $Y^3$ are as defined for the compound of formula I. Preferred definitions of $G^1$, $R^1$, $R^2$, $X^1$, $X^2$, $X^3$, $X^4$, $Y^2$, and $Y^3$ are the same as for the corresponding substituents of compounds of formula I.

Compound of formula X5

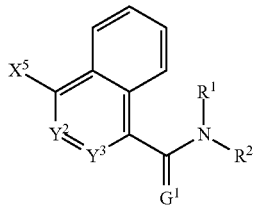

(X5)

wherein $G^1$, $R^1$, $R^2$, $Y^2$, and $Y^3$ are as defined for the compound of formula I and $X^5$ is chloro, bromo, iodo, amino, CHO, CN, OH, C(=O)OH, C(=NOH)H, C(=NOH)Cl, C(=NOH)NH$_2$, C(=O)CH$_3$, C(=NOH)CH$_3$, C(=O)CH$_2$Cl, or C(=O)CH$_2$Br. Preferred definitions of $G^1$, $R^1$, $R^2$, $Y^2$, and $Y^3$ are the same as for the corresponding substituents of compounds of formula I.

The following embodiments apply to intermediates $X^1$, $X^2$, $X^3$, $X^4$ and $X^5$ as well as compounds of formula I. Embodiments may be combined where possible.

In embodiment A1 $A^1$ is S and $A^2$ is CH$_2$.
In embodiment A2 $A^1$ is SO and $A^2$ is CH$_2$.
In embodiment A3 $A^1$ is SO$_2$ and $A^2$ is CH$_2$.
In embodiment A4 $A^1$ is CH$_2$ and $A^2$ is S.
In embodiment A5 $A^1$ is CH$_2$ and $A^2$ is SO.
In embodiment A6 $A^1$ is CH$_2$ and $A^2$ is SO$_2$.
In embodiment B1 $A^1$ is S and $A^2$ is CH$_2$ and L is a bond.
In embodiment B2 $A^1$ is SO and $A^2$ is CH$_2$ and L is a bond.
In embodiment B3 $A^1$ is SO$_2$ and $A^2$ is CH$_2$ and L is a bond.
In embodiment B4 $A^1$ is CH$_2$ and $A^2$ is S and L is a bond.
In embodiment B5 $A^1$ is CH$_2$ and $A^2$ is SO and L is a bond.
In embodiment B6 $A^1$ is CH$_2$ and $A^2$ is SO$_2$ and L is a bond.
In embodiment B7 $A^1$ is S and $A^2$ is CH$_2$ and L is methylene.
In embodiment B8 $A^1$ is SO and $A^2$ is CH$_2$ and L is methylene.
In embodiment B9 $A^1$ is SO$_2$ and $A^2$ is CH$_2$ and L is methylene.
In embodiment B10 $A^1$ is CH$_2$ and $A^2$ is S and L is methylene.
In embodiment B11 $A^1$ is CH$_2$ and $A^2$ is SO and L is methylene.
In embodiment B12 $A^1$ is CH$_2$ and $A^2$ is SO$_2$ and L is methylene.
In embodiment B13 $A^1$ is S and $A^2$ is CH$_2$ and L is ethylene.
In embodiment B14 $A^1$ is SO and $A^2$ is CH$_2$ and L is ethylene.
In embodiment B15 $A^1$ is SO$_2$ and $A^2$ is CH$_2$ and L is ethylene.
In embodiment B16 $A^1$ is CH$_2$ and $A^2$ is S and L is ethylene.
In embodiment B17 $A^1$ is CH$_2$ and $A^2$ is SO and L is ethylene.
In embodiment B18 $A^1$ is CH$_2$ and $A^2$ is SO$_2$ and L is ethylene.

In embodiment C1 the invention provides compounds of formula I wherein $X^2$ is C—$X^6$.
In embodiment C2 the invention provides compounds of formula I wherein $X^2$ is C—$X^6$, $Y^2$ and $Y^3$ are C—H.
In embodiment C3 the invention provides compounds of formula I wherein $X^2$ is C—$X^6$, $Y^2$ and $Y^3$ are C—H and each $R^4$ is hydrogen.
In embodiment C4 the invention provides compounds of formula I wherein $X^2$ is C—$X^6$, $Y^2$ and $Y^3$ are C—H, $R^3$ is hydrogen and each $R^4$ is hydrogen.

In embodiment E1 the invention provides compounds of formula I wherein $R^2$ is thietan-3-yl- and $G^1$, $R^1$, $Y^2$, $Y^3$, $X^1$, $X^2$, $X^3$ and $X^4$ are as defined for the compound of formula I.
In embodiment E2 the invention provides compounds of formula I wherein $R^2$ is 1-oxo-thietan-3-yl- and $G^1$, $R^1$, $Y^2$, $Y^3$, $X^1$, $X^2$, $X^3$ and $X^4$ are as defined for the compound of formula I.
In embodiment E3 the invention provides compounds of formula I wherein $R^2$ is 1,1-Dioxo-thietan-3-yl- and $G^1$, $R^1$, $Y^2$, $Y^3$, $X^1$, $X^2$, $X^3$ and $X^4$ are as defined for the compound of formula I.
In embodiment E4 the invention provides compounds of formula I wherein $R^2$ is 2,2-dimethylthietan-3-yl- and $G^1$, $R^1$, $Y^2$, $Y^3$, $X^1$, $X^2$, $X^3$ and $X^4$ are as defined for the compound of formula I.
In embodiment E5 the invention provides compounds of formula I wherein $R^2$ is 2,2-dimethyl-1-oxo-thietan-3-yl- and $G^1$, $R^1$, $Y^2$, $Y^3$, $X^1$, $X^2$, $X^3$ and $X^4$ are as defined for the compound of formula I.
In embodiment E6 the invention provides compounds of formula I wherein $R^2$ is 2,2-dimethyl-1,1-Dioxo-thietan-3-yl- and $G^1$, $R^1$, $Y^2$, $Y^3$, $X^1$, $X^2$, $X^3$ and $X^4$ are as defined for the compound of formula I.
In embodiment E7 the invention provides compounds of formula I wherein $R^2$ is 3-Methyl-thietan-3-yl- and $G^1$, $R^1$, $Y^2$, $Y^3$, $X^1$, $X^2$, $X^3$ and $X^4$ are as defined for the compound of formula I.
In embodiment E8 the invention provides compounds of formula I wherein $R^2$ is 3-Methyl-1-oxo-thietan-3-yl- and $G^1$, $R^1$, $Y^2$, $Y^3$, $X^1$, $X^2$, $X^3$ and $X^4$ are as defined for the compound of formula I.
In embodiment E9 the invention provides compounds of formula I wherein $R^2$ is 3-Methyl-1,1-Dioxo-thietan-3-yl- and $G^1$, $R^1$, $Y^2$, $Y^3$, $X^1$, $X^2$, $X^3$ and $X^4$ are as defined for the compound of formula I.
In embodiment E10 the invention provides compounds of formula I wherein $R^2$ is thietan-3-ylmethyl- and $G^1$, $R^1$, $Y^2$, $Y^3$, $X^1$, $X^2$, $X^3$ and $X^4$ are as defined for the compound of formula I.
In embodiment E11 the invention provides compounds of formula I wherein $R^2$ is 1-oxo-thietan-3-ylmethyl- and $G^1$, $R^1$, $Y^2$, $Y^3$, $X^1$, $X^2$, $X^3$ and $X^4$ are as defined for the compound of formula I.
In embodiment E12 the invention provides compounds of formula I wherein $R^2$ is 1,1-Dioxo-thietan-3-ylmethyl- and $G^1$, $R^1$, $Y^2$, $Y^3$, $X^1$, $X^2$, $X^3$ and $X^4$ are as defined for the compound of formula I.

In embodiment E13 the invention provides compounds of formula I wherein $R^2$ is thietan-2-ylmethyl- and $G^1$, $R^1$, $Y^2$, $Y^3$, $X^1$, $X^2$, $X^3$ and $X^4$ are as defined for the compound of formula I.

In embodiment E14 the invention provides compounds of formula I wherein $R^2$ is (1-oxothietan-2-yl)methyl- and $G^1$, $R^1$, $Y^2$, $Y^3$, $X^1$, $X^2$, $X^3$ and $X^4$ are as defined for the compound of formula I.

In embodiment E15 the invention provides compounds of formula I wherein $R^2$ is (1,1-dioxothietan-2-yl)methyl- and $G^1$, $R^1$, $Y^2$, $Y^3$, $X^1$, $X^2$, $X^3$ and $X^4$ are as defined for the compound of formula I.

In embodiment E16 the invention provides compounds of formula I wherein $R^2$ is 2-(thietan-3-yl)ethanyl and $G^1$, $R^1$, $Y^2$, $Y^3$, $X^1$, $X^2$, $X^3$ and $X^4$ are as defined for the compound of formula I.

In embodiment E17 the invention provides compounds of formula I wherein $R^2$ is 2-(1,1-dioxothietan-3-yl)ethanyl and $G^1$, $R^1$, $Y^2$, $Y^3$, $X^1$, $X^2$, $X^3$ and $X^4$ are as defined for the compound of formula I.

In embodiment E18 the invention provides compounds of formula I wherein $R^2$ is 2-(1-oxothietan-3-yl)ethanyl and $G^1$, $R^1$, $Y^2$, $Y^3$, $X^1$, $X^2$, $X^3$ and $X^4$ are as defined for the compound of formula I.

In embodiment E19 the invention provides compounds of formula I wherein $Y^2$ is CH, $Y^3$ is CH and $G^1$, $R^1$, $R^2$, $X^1$, $X^2$, $X^3$ and $X^4$ are as defined for the compound of formula I.

In embodiment E20 the invention provides compounds of formula I wherein $Y^2$ is N, $Y^3$ is CH and $G^1$, $R^1$, $R^2$, $X^1$, $X^2$, $X^3$ and $X^4$ are as defined for the compound of formula I.

In embodiment E21 the invention provides compounds of formula I wherein $Y^2$ is CH, $Y^3$ is N and $G^1$, $R^1$, $R^2$, $X^1$, $X^2$, $X^3$ and $X^4$ are as defined for the compound of formula I.

In embodiment E22 the invention provides compounds of formula I wherein $X^1$ is chloro, $X^2$ is CH, $X^3$ is chloro and $G^1$, $R^1$, $R^2$, $Y^2$, $Y^3$, $X^1$, $X^2$, $X^3$ and $X^4$ are as defined for the compound of formula I.

In embodiment E23 the invention provides compounds of formula I wherein $X^1$ is chloro, $X^2$ is C—F, $X^3$ is hydrogen and $G^1$, $R^1$, $R^2$, $Y^2$, $Y^3$ and $X^4$ are as defined for the compound of formula I.

In embodiment E24 the invention provides compounds of formula I wherein $X^1$ is fluoro, $X^2$ is C—Cl, $X^3$ is hydrogen and $G^1$, $R^1$, $R^2$, $Y^2$, $Y^3$ and $X^4$ are as defined for the compound of formula I.

In embodiment E25 the invention provides compounds of formula I wherein $X^1$ is chloro, $X^2$ is C—Cl, $X^3$ is hydrogen and $G^1$, $R^1$, $R^2$, $Y^2$, $Y^3$ and $X^4$ are as defined for the compound of formula I.

In embodiment E26 the invention provides compounds of formula I wherein $X^1$ is chloro, $X^2$ is C—Br, $X^3$ is chloro and $G^1$, $R^1$, $R^2$, $Y^2$, $Y^3$ and $X^4$ are as defined for the compound of formula I.

In embodiment E27 the invention provides compounds of formula I wherein $X^1$ is chloro, $X^2$ is C—F, $X^3$ is chloro and $G^1$, $R^1$, $R^2$, $Y^2$, $Y^3$ and $X^4$ are as defined for the compound of formula I.

In embodiment E28 the invention provides compounds of formula I wherein $X^1$ is chloro, $X^2$ is C—Cl, $X^3$ is chloro and $G^1$, $R^1$, $R^2$, $Y^2$, $Y^3$ and $X^4$ are as defined for the compound of formula I.

In embodiment E29 the invention provides compounds of formula I wherein $X^1$ is chloro, $X^2$ is C—I, $X^3$ is chloro and $G^1$, $R^1$, $R^2$, $Y^2$, $Y^3$ and $X^4$ are as defined for the compound of formula I.

In embodiment E30 the invention provides compounds of formula I wherein $X^1$ is fluoro, $X^2$ is C—F, $X^3$ is fluoro and $G^1$, $R^1$, $R^2$, $Y^2$, $Y^3$ and $X^4$ are as defined for the compound of formula I.

In embodiment E31 the invention provides compounds of formula I wherein $X^1$ is chloro, $X^2$ is CH, $X^3$ is bromo and $G^1$, $R^1$, $R^2$, $Y^2$, $Y^3$ and $X^4$ are as defined for the compound of formula I.

In embodiment E32 the invention provides compounds of formula I wherein $X^1$ is chloro, $X^2$ is CH, $X^3$ is fluoro and $G^1$, $R^1$, $R^2$, $Y^2$, $Y^3$ and $X^4$ are as defined for the compound of formula I.

In embodiment E33 the invention provides compounds of formula I wherein $X^1$ is chloro, $X^2$ is CH, $X^3$ is trifluoromethyl and $G^1$, $R^1$, $R^2$, $Y^2$, $Y^3$ and $X^4$ are as defined for the compound of formula I.

In embodiment E34 the invention provides compounds of formula I wherein $X^1$ is chloro, $X^2$ is C—Cl, $X^3$ is trifluoromethyl and $G^1$, $R^1$, $R^2$, $Y^2$, $Y^3$ and $X^4$ are as defined for the compound of formula I.

In embodiment E35 the invention provides compounds of formula I wherein $X^1$ is trifluoromethyl, $X^2$ is CH, $X^3$ is trifluoromethyl and $G^1$, $R^1$, $R^2$, $Y^2$, $Y^3$ and $X^4$ are as defined for the compound of formula I.

In embodiment E36 the invention provides compounds of formula I wherein $X^1$ is trifluoromethyl, $X^2$ is C—Cl, $X^3$ is trifluoromethyl and $G^1$, $R^1$, $R^2$, $Y^2$, $Y^3$ and $X^4$ are as defined for the compound of formula I.

In embodiment E37 the invention provides compounds of formula I wherein $X^1$ is trifluoromethyl, $X^2$ is CH, $X^3$ is hydrogen and $G^1$, $R^1$, $R^2$, $Y^2$, $Y^3$ and $X^4$ are as defined for the compound of formula I.

In embodiment E38 the invention provides compounds of formula I wherein $X^1$ is chloro, $X^2$ is N, $X^3$ is chloro and $G^1$, $R^1$, $R^2$, $Y^2$, $Y^3$ and $X^4$ are as defined for the compound of formula I.

In embodiment E39 the invention provides compounds of formula I wherein $X^1$ is trifluoromethyl, $X^2$ is N, $X^3$ is trifluoromethyl and $G^1$, $R^1$, $R^2$, $Y^2$, $Y^3$, $X^1$, $X^2$, and $X^3$ are as defined for the compound of formula I.

In embodiment E40 the invention provides compounds of formula I wherein $X^4$ is trifluoromethyl and $G^1$, $R^1$, $R^2$, $Y^2$, $Y^3$, $X^1$, $X^2$, and $X^3$ are as defined for the compound of formula I.

In embodiment E41 the invention provides compounds of formula I wherein $X^4$ is difluoromethyl and $G^1$, $R^1$, $R^2$, $Y^2$, $Y^3$, $X^1$, $X^2$, and $X^3$ are as defined for the compound of formula I.

In embodiment E42 the invention provides compounds of formula I wherein $X^4$ is chlorodifluoromethyl and $G^1$, $R^1$, $R^2$, $Y^2$, $Y^3$, $X^1$, $X^2$, and $X^3$ are as defined for the compound of formula I.

In embodiment F1 the invention provides compounds of formula I wherein $X^4$ is chlorodifluoromethyl and $R^2$ is thietan-3-yl- and $G^1$, $R^1$, $Y^2$, $Y^3$, $X^1$, $X^2$ and $X^3$ are as defined for the compound of formula I.

In embodiment F2 the invention provides compounds of formula I wherein $X^4$ is chlorodifluoromethyl and $R^2$ is 1-oxo-thietan-3-yl- and $G^1$, $R^1$, $Y^2$, $Y^3$, $X^1$, $X^2$ and $X^3$ are as defined for the compound of formula I.

In embodiment F3 the invention provides compounds of formula I wherein $X^4$ is chlorodifluoromethyl and $R^2$ is 1,1-Dioxo-thietan-3-yl- and $G^1$, $R^1$, $Y^2$, $Y^3$, $X^1$, $X^2$ and $X^3$ are as defined for the compound of formula I.

In embodiment F4 the invention provides compounds of formula I wherein $X^4$ is chlorodifluoromethyl and $R^2$ is 2,2- dimethylthietan-3-yl- and $G^1$, $R^1$, $Y^2$, $Y^3$, $X^1$, $X^2$ and $X^3$ are as defined for the compound of formula I.

In embodiment F5 the invention provides compounds of formula I wherein $X^4$ is chlorodifluoromethyl and $R^2$ is 2,2-dimethyl-1-oxo-thietan-3-yl- and $G^1$, $R^1$, $Y^2$, $Y^3$, $X^1$, $X^2$ and $X^3$ are as defined for the compound of formula I.

In embodiment F6 the invention provides compounds of formula I wherein $X^4$ is chlorodifluoromethyl and $R^2$ is 2,2-dimethyl-1,1-Dioxo-thietan-3-yl- and $G^1$, $R^1$, $Y^2$, $Y^3$, $X^1$, $X^2$ and $X^3$ are as defined for the compound of formula I.

In embodiment F7 the invention provides compounds of formula I wherein $X^4$ is chlorodifluoromethyl and $R^2$ is 3-Methyl-thietan-3-yl- and $G^1$, $R^1$, $Y^2$, $Y^3$, $X^1$, $X^2$ and $X^3$ are as defined for the compound of formula I.

In embodiment F8 the invention provides compounds of formula I wherein $X^4$ is chlorodifluoromethyl and $R^2$ is 3-Methyl-1-oxo-thietan-3-yl- and $G^1$, $R^1$, $Y^2$, $Y^3$, $X^1$, $X^2$ and $X^3$ are as defined for the compound of formula I.

In embodiment F9 the invention provides compounds of formula I wherein $X^4$ is chlorodifluoromethyl and $R^2$ is 3-Methyl-1,1-Dioxo-thietan-3-yl- and $G^1$, $R^1$, $Y^2$, $Y^3$, $X^1$, $X^2$ and $X^3$ are as defined for the compound of formula I.

In embodiment F10 the invention provides compounds of formula I wherein $X^4$ is chlorodifluoromethyl and $R^2$ is thietan-3-ylmethyl- and $G^1$, $R^1$, $Y^2$, $Y^3$, $X^1$, $X^2$ and $X^3$ are as defined for the compound of formula I.

In embodiment F11 the invention provides compounds of formula I wherein $X^4$ is chlorodifluoromethyl and $R^2$ is 1-oxo-thietan-3-ylmethyl- and $G^1$, $R^1$, $Y^2$, $Y^3$, $X^1$, $X^2$ and $X^3$ are as defined for the compound of formula I.

In embodiment F12 the invention provides compounds of formula I wherein $X^4$ is chlorodifluoromethyl and $R^2$ is 1,1-Dioxo-thietan-3-ylmethyl- and $G^1$, $R^1$, $Y^2$, $Y^3$, $X^1$, $X^2$ and $X^3$ are as defined for the compound of formula I.

In embodiment F13 the invention provides compounds of formula I wherein $X^4$ is chlorodifluoromethyl and $R^2$ is thietan-2-ylmethyl- and $G^1$, $R^1$, $Y^2$, $Y^3$, $X^1$, $X^2$ and $X^3$ are as defined for the compound of formula I.

In embodiment F14 the invention provides compounds of formula I wherein $X^4$ is chlorodifluoromethyl and $R^2$ is (1-oxothietan-2-yl)methyl- and $G^1$, $R^1$, $Y^2$, $Y^3$, $X^1$, $X^2$ and $X^3$ are as defined for the compound of formula I.

In embodiment F15 the invention provides compounds of formula I wherein $X^4$ is chlorodifluoromethyl and $R^2$ is (1,1-dioxothietan-2-yl)methyl- and $G^1$, $R^1$, $Y^2$, $Y^3$, $X^1$, $X^2$ and $X^3$ are as defined for the compound of formula I.

In embodiment F16 the invention provides compounds of formula I wherein $X^4$ is chlorodifluoromethyl and $R^2$ is 2-(thietan-3-yl)ethanyl and $G^1$, $R^1$, $Y^2$, $Y^3$, $X^1$, $X^2$ and $X^3$ are as defined for the compound of formula I.

In embodiment F17 the invention provides compounds of formula I wherein $X^4$ is chlorodifluoromethyl and $R^2$ is 2-(1,1-dioxothietan-3-yl)ethanyl and $G^1$, $R^1$, $Y^2$, $Y^3$, $X^1$, $X^2$ and $X^3$ are as defined for the compound of formula I.

In embodiment F18 the invention provides compounds of formula I wherein $X^4$ is chlorodifluoromethyl and $R^2$ is 2-(1-oxothietan-3-yl)ethanyl and $G^1$, $R^1$, $Y^2$, $Y^3$, $X^1$, $X^2$ and $X^3$ are as defined for the compound of formula I.

In embodiment F19 the invention provides compounds of formula I wherein $X^4$ is chlorodifluoromethyl and $Y^2$ is CH, $Y^3$ is CH and $G^1$, $R^1$, $R^2$, $X^1$, $X^2$ and $X^3$ are as defined for the compound of formula I.

In embodiment F20 the invention provides compounds of formula I wherein $X^4$ is chlorodifluoromethyl and, $Y^2$ is N, $Y^3$ is CH and $G^1$, $R^1$, $R^2$, $X^1$, $X^2$ and $X^3$ are as defined for the compound of formula I.

In embodiment F21 the invention provides compounds of formula I wherein $X^4$ is chlorodifluoromethyl and $Y^2$ is CH, $Y^3$ is N and $G^1$, $R^1$, $R^2$, $X^1$, $X^2$ and $X^3$ are as defined for the compound of formula I.

In embodiment F23 the invention provides compounds of formula I wherein $X^4$ is chlorodifluoromethyl and $X^1$ is chloro, $X^2$ is CH, $X^3$ is chloro and $G^1$, $R^1$, $R^2$, $Y^2$, $Y^3$, are as defined for the compound of formula I.

In embodiment F24 the invention provides compounds of formula I wherein $X^4$ is chlorodifluoromethyl and $X^1$ is chloro, $X^2$ is C—F, $X^3$ is hydrogen and $G^1$, $R^1$, $R^2$, $Y^2$, $Y^3$, are as defined for the compound of formula I.

In embodiment F25 the invention provides compounds of formula I wherein $X^4$ is chlorodifluoromethyl and $X^1$ is fluoro, $X^2$ is C—Cl, $X^3$ is hydrogen and $G^1$, $R^1$, $R^2$, $Y^2$, $Y^3$, are as defined for the compound of formula I.

In embodiment F26 the invention provides compounds of formula I wherein $X^4$ is chlorodifluoromethyl and $X^1$ is chloro, $X^2$ is C—Cl, $X^3$ is hydrogen and $G^1$, $R^1$, $R^2$, $Y^2$, $Y^3$, are as defined for the compound of formula I.

In embodiment F27 the invention provides compounds of formula I wherein $X^4$ is chlorodifluoromethyl and $X^1$ is chloro, $X^2$ is C—Br, $X^3$ is chloro and $G^1$, $R^1$, $R^2$, $Y^2$, $Y^3$, are as defined for the compound of formula I.

In embodiment F28 the invention provides compounds of formula I wherein $X^4$ is chlorodifluoromethyl and $X^1$ is chloro, $X^2$ is C—F, $X^3$ is chloro and $G^1$, $R^1$, $R^2$, $Y^2$, $Y^3$, are as defined for the compound of formula I.

In embodiment F29 the invention provides compounds of formula I wherein $X^4$ is chlorodifluoromethyl and $X^1$ is chloro, $X^2$ is C—Cl, $X^3$ is chloro and $G^1$, $R^1$, $R^2$, $Y^2$, $Y^3$, are as defined for the compound of formula I.

In embodiment F30 the invention provides compounds of formula I wherein $X^4$ is chlorodifluoromethyl and $X^1$ is chloro, $X^2$ is C—I, $X^3$ is chloro and $G^1$, $R^1$, $R^2$, $Y^2$, $Y^3$, are as defined for the compound of formula I.

In embodiment F31 the invention provides compounds of formula I wherein $X^4$ is chlorodifluoromethyl and $X^1$ is fluoro, $X^2$ is C—F, $X^3$ is fluoro and $G^1$, $R^1$, $R^2$, $Y^2$, $Y^3$, are as defined for the compound of formula I.

In embodiment F32 the invention provides compounds of formula I wherein $X^4$ is chlorodifluoromethyl and $X^1$ is chloro, $X^2$ is CH, $X^3$ is bromo and $G^1$, $R^1$, $R^2$, $Y^2$, $Y^3$, are as defined for the compound of formula I.

In embodiment F33 the invention provides compounds of formula I wherein $X^4$ is chlorodifluoromethyl and $X^1$ is chloro, $X^2$ is CH, $X^3$ is fluoro and $G^1$, $R^1$, $R^2$, $Y^2$, $Y^3$, are as defined for the compound of formula I.

In embodiment F34 the invention provides compounds of formula I wherein $X^4$ is chlorodifluoromethyl and $X^1$ is chloro, $X^2$ is CH, $X^3$ is trifluoromethyl and $G^1$, $R^1$, $R^2$, $Y^2$, $Y^3$, are as defined for the compound of formula I.

In embodiment F35 the invention provides compounds of formula I wherein $X^4$ is chlorodifluoromethyl and $X^1$ is chloro, $X^2$ is C—Cl, $X^3$ is trifluoromethyl and $G^1$, $R^1$, $R^2$, $Y^2$, $Y^3$, are as defined for the compound of formula I.

In embodiment F36 the invention provides compounds of formula I wherein $X^4$ is chlorodifluoromethyl and $X^1$ is trifluoromethyl, $X^2$ is CH, $X^3$ is trifluoromethyl and $G^1$, $R^1$, $R^2$, $Y^2$, $Y^3$, are as defined for the compound of formula I.

In embodiment F37 the invention provides compounds of formula I wherein $X^4$ is chlorodifluoromethyl and $X^1$ is trifluoromethyl, $X^2$ is C—Cl, $X^3$ is trifluoromethyl and $G^1$, $R^1$, $R^2$, $Y^2$, $Y^3$, are as defined for the compound of formula I.

In embodiment F38 the invention provides compounds of formula I wherein $X^4$ is chlorodifluoromethyl and $X^1$ is trifluoromethyl, $X^2$ is CH, $X^3$ is hydrogen and $G^1, R^1, R^2, Y^2, Y^3$, are as defined for the compound of formula I.

In embodiment F39 the invention provides compounds of formula I wherein $X^4$ is chlorodifluoromethyl and $X^1$ is chloro, $X^2$ is N, $X^3$ is chloro and $G^1, R^1, R^2, Y^2, Y^3$, are as defined for the compound of formula I.

In embodiment F40 the invention provides compounds of formula I wherein $X^4$ is chlorodifluoromethyl and $X^1$ is trifluoromethyl, $X^2$ is N, $X^3$ is trifluoromethyl and $G^1, R^1, R^2, Y^2, Y^3$ are as defined for the compound of formula I.

In embodiment G1 the invention provides compounds of formula I wherein $X^2$ is C—$X^6$, none of $X^1, X^3$ and $X^6$ are hydrogen and $R^2$ is thietan-3-yl- and $G^1, R^1, Y^2, Y^3$, and $X^4$ are as defined for the compound of formula I.

In embodiment G2 the invention provides compounds of formula I wherein $X^2$ is C—$X^6$, none of $X^1, X^3$ and $X^6$ are hydrogen and $R^2$ is 1-oxo-thietan-3-yl- and $G^1, R^1, Y^2, Y^3$, and $X^4$ are as defined for the compound of formula I.

In embodiment G3 the invention provides compounds of formula I wherein $X^2$ is C—$X^6$, none of $X^1, X^3$ and $X^6$ are hydrogen and $R^2$ is 1,1-Dioxo-thietan-3-yl- and $G^1, R^1, Y^2, Y^3$, and $X^4$ are as defined for the compound of formula I.

In embodiment G4 the invention provides compounds of formula I wherein $X^2$ is C—$X^6$, none of $X^1, X^3$ and $X^6$ are hydrogen and $R^2$ is 2,2-dimethylthietan-3-yl- and $G^1, R^1, Y^2, Y^3$, and $X^4$ are as defined for the compound of formula I.

In embodiment G5 the invention provides compounds of formula I wherein $X^2$ is C—$X^6$, none of $X^1$, $X^3$ and $X^6$ are hydrogen and $R^2$ is 2,2-dimethyl-1-oxo-thietan-3-yl- and $G^1, R^1, Y^2, Y^3$, and $X^4$ are as defined for the compound of formula I.

In embodiment G6 the invention provides compounds of formula I wherein $X^2$ is C—$X^6$, none of $X^1, X^3$ and $X^6$ are hydrogen and $R^2$ is 2,2-dimethyl-1,1-Dioxo-thietan-3-yl- and $G^1, R^1, Y^2, Y^3$, and $X^4$ are as defined for the compound of formula I.

In embodiment G7 the invention provides compounds of formula I wherein $X^2$ is C—$X^6$, none of $X^1, X^3$ and $X^6$ are hydrogen and $R^2$ is 3-Methyl-thietan-3-yl- and $G^1, R^1, Y^2, Y^3$, and $X^4$ are as defined for the compound of formula I.

In embodiment G8 the invention provides compounds of formula I wherein $X^2$ is C—$X^6$, none of $X^1, X^3$ and $X^6$ are hydrogen and $R^2$ is 3-Methyl-1-oxo-thietan-3-yl- and $G^1, R^1, Y^2, Y^3$, and $X^4$ are as defined for the compound of formula I.

In embodiment G9 the invention provides compounds of formula I wherein $X^2$ is C—$X^6$, none of $X^1, X^3$ and $X^6$ are hydrogen and $R^2$ is 3-Methyl-1,1-Dioxo-thietan-3-yl- and $G^1, R^1, Y^2, Y^3$, and $X^4$ are as defined for the compound of formula I.

In embodiment G10 the invention provides compounds of formula I wherein $X^2$ is C—$X^6$, none of $X^1, X^3$ and $X^6$ are hydrogen and $R^2$ is thietan-3-ylmethyl- and $G^1, R^1, Y^2, Y^3$, and $X^4$ are as defined for the compound of formula I.

In embodiment G11 the invention provides compounds of formula I wherein $X^2$ is C—$X^6$, none of $X^1, X^3$ and $X^6$ are hydrogen and $R^2$ is 1-oxo-thietan-3-ylmethyl- and $G^1, R^1, Y^2, Y^3$, and $X^4$ are as defined for the compound of formula I.

In embodiment G12 the invention provides compounds of formula I wherein $X^2$ is C—$X^6$, none of $X^1, X^3$ and $X^6$ are hydrogen and $R^2$ is 1,1-Dioxo-thietan-3-ylmethyl- and $G^1, R^1, Y^2, Y^3$, and $X^4$ are as defined for the compound of formula I.

In embodiment G13 the invention provides compounds of formula I wherein $X^2$ is C—$X^6$, none of $X^1, X^3$ and $X^6$ are hydrogen and $R^2$ is thietan-2-ylmethyl- and $G^1, R^1, Y^2, Y^3$, and $X^4$ are as defined for the compound of formula I.

In embodiment G14 the invention provides compounds of formula I wherein $X^2$ is C—$X^6$, none of $X^1, X^3$ and $X^6$ are hydrogen and $R^2$ is (1-oxothietan-2-yl)methyl- and $G^1, R^1, Y^2, Y^3$, and $X^4$ are as defined for the compound of formula I.

In embodiment G15 the invention provides compounds of formula I wherein $X^2$ is C—$X^6$, none of $X^1, X^3$ and $X^6$ are hydrogen and $R^2$ is (1,1-dioxothietan-2-yl)methyl- and $G^1, R^1, Y^2, Y^3$, and $X^4$ are as defined for the compound of formula I.

In embodiment G16 the invention provides compounds of formula I wherein $X^2$ is C—$X^6$, none of $X^1, X^3$ and $X^6$ are hydrogen and $R^2$ is 2-(thietan-3-yl)ethanyl and $G^1, R^1, Y^2, Y^3$, and $X^4$ are as defined for the compound of formula I.

In embodiment G17 the invention provides compounds of formula I wherein $X^2$ is C—$X^6$, none of $X^1, X^3$ and $X^6$ are hydrogen and $R^2$ is 2-(1,1-dioxothietan-3-yl)ethanyl and $G^1, R^1, Y^2, Y^3$, and $X^4$ are as defined for the compound of formula I.

In embodiment G18 the invention provides compounds of formula I wherein $X^2$ is C—$X^6$, none of $X^1, X^3$ and $X^6$ are hydrogen and $R^2$ is 2-(1-oxothietan-3-yl)ethanyl and $G^1, R^1, Y^2, Y^3$, and $X^4$ are as defined for the compound of formula I.

In embodiment G19 the invention provides compounds of formula I wherein $X^2$ is C—$X^6$, none of $X^1, X^3$ and $X^6$ are hydrogen and $Y^2$ is CH, $Y^3$ is CH and $G^1, R^1, R^2$, and $X^4$ are as defined for the compound of formula I.

In embodiment G20 the invention provides compounds of formula I wherein $X^2$ is C—$X^6$, none of $X^1, X^3$ and $X^6$ are hydrogen and $Y^2$ is N, $Y^3$ is CH and $G^1, R^1, R^2$, and $X^4$ are as defined for the compound of formula I.

In embodiment G21 the invention provides compounds of formula I wherein $X^2$ is C—$X^6$, none of $X^1, X^3$ and $X^6$ are hydrogen and $Y^2$ is CH, $Y^3$ is N and $G^1, R^1, R^2$, and $X^4$ are as defined for the compound of formula I.

In embodiment G22 the invention provides compounds of formula I wherein $X^2$ is C—$X^6$, none of $X^1, X^3$ and $X^6$ are hydrogen and $X^4$ is trifluoromethyl and $G^1, R^1, R^2, Y^2, Y^3$ are as defined for the compound of formula I.

In embodiment G23 the invention provides compounds of formula I wherein $X^2$ is C—$X^6$, none of $X^1, X^3$ and $X^6$ are hydrogen and $X^4$ is difluoromethyl and $G^1, R^1, R^2, Y^2, Y^3$ are as defined for the compound of formula I.

In embodiment G24 the invention provides compounds of formula I wherein $X^2$ is C—$X^6$, none of $X^1, X^3$ and $X^6$ are hydrogen and $X^4$ is chlorodifluoromethyl and $G^1, R^1, R^2, Y^2, Y^3$ are as defined for the compound of formula I.

In embodiment H1 the invention provides compounds of formula I wherein $X^1$ is chloro, $X^2$ is CH, $X^3$ is trifluoromethyl and $R^2$ is thietan-3-yl- and $G^1, R^1, Y^2, Y^3$, and $X^4$ are as defined for the compound of formula I.

In embodiment H2 the invention provides compounds of formula I wherein $X^1$ is chloro, $X^2$ is CH, $X^3$ is trifluoromethyl and $R^2$ is 1-oxo-thietan-3-yl- and $G^1, R^1, Y^2, Y^3$, and $X^4$ are as defined for the compound of formula I.

In embodiment H3 the invention provides compounds of formula I wherein $X^1$ is chloro, $X^2$ is CH, $X^3$ is trifluoromethyl and $R^2$ is 1,1-Dioxo-thietan-3-yl- and $G^1, R^1, Y^2, Y^3$, and $X^4$ are as defined for the compound of formula I.

In embodiment H4 the invention provides compounds of formula I wherein $X^1$ is chloro, $X^2$ is CH, $X^3$ is trifluoromethyl and $R^2$ is 2,2-dimethylthietan-3-yl- and $G^1, R^1, Y^2, Y^3$, and $X^4$ are as defined for the compound of formula I.

In embodiment H5 the invention provides compounds of formula I wherein $X^1$ is chloro, $X^2$ is CH, $X^3$ is trifluoromethyl and $R^2$ is 2,2-dimethyl-1-oxo-thietan-3-yl- and $G^1, R^1, Y^2, Y^3$, and $X^4$ are as defined for the compound of formula I.

In embodiment H6 the invention provides compounds of formula I wherein $X^1$ is chloro, $X^2$ is CH, $X^3$ is trifluoromethyl and $R^2$ is 2,2-dimethyl-1,1-Dioxo-thietan-3-yl- and $G^1$, $R^1$, $Y^2$, $Y^3$, and $X^4$ are as defined for the compound of formula I.

In embodiment H7 the invention provides compounds of formula I wherein $X^1$ is chloro, $X^2$ is CH, $X^3$ is trifluoromethyl and $R^2$ is 3-Methyl-thietan-3-yl- and $G^1$, $R^1$, $Y^2$, $Y^3$, and $X^4$ are as defined for the compound of formula I.

In embodiment H8 the invention provides compounds of formula I wherein $X^1$ is chloro, $X^2$ is CH, $X^3$ is trifluoromethyl and $R^2$ is 3-Methyl-1-oxo-thietan-3-yl- and $G^1$, $R^1$, $Y^2$, $Y^3$, and $X^4$ are as defined for the compound of formula I.

In embodiment H9 the invention provides compounds of formula I wherein $X^1$ is chloro, $X^2$ is CH, $X^3$ is trifluoromethyl and $R^2$ is 3-Methyl-1,1-Dioxo-thietan-3-yl- and $G^1$, $R^1$, $Y^2$, $Y^3$, and $X^4$ are as defined for the compound of formula I.

In embodiment H10 the invention provides compounds of formula I wherein $X^1$ is chloro, $X^2$ is CH, $X^3$ is trifluoromethyl and $R^2$ is thietan-3-ylmethyl- and $G^1$, $R^1$, $Y^2$, $Y^3$, and $X^4$ are as defined for the compound of formula I.

In embodiment H11 the invention provides compounds of formula I wherein $X^1$ is chloro, $X^2$ is CH, $X^3$ is trifluoromethyl and $R^2$ is 1-oxo-thietan-3-ylmethyl- and $G^1$, $R^1$, $Y^2$, $Y^3$, and $X^4$ are as defined for the compound of formula I.

In embodiment H12 the invention provides compounds of formula I wherein $X^1$ is chloro, $X^2$ is CH, $X^3$ is trifluoromethyl and $R^2$ is 1,1-Dioxo-thietan-3-ylmethyl- and $G^1$, $R^1$, $Y^2$, $Y^3$, and $X^4$ are as defined for the compound of formula I.

In embodiment H13 the invention provides compounds of formula I wherein $X^1$ is chloro, $X^2$ is CH, $X^3$ is trifluoromethyl and $R^2$ is thietan-2-ylmethyl- and $G^1$, $R^1$, $Y^2$, $Y^3$, and $X^4$ are as defined for the compound of formula I.

In embodiment H14 the invention provides compounds of formula I wherein $X^1$ is chloro, $X^2$ is CH, $X^3$ is trifluoromethyl and $R^2$ is (1-oxothietan-2-yl)methyl- and $G^1$, $R^1$, $Y^2$, $Y^3$, and $X^4$ are as defined for the compound of formula I.

In embodiment H15 the invention provides compounds of formula I wherein $X^1$ is chloro, $X^2$ is CH, $X^3$ is trifluoromethyl and $R^2$ is (1,1-dioxothietan-2-yl)methyl- and $G^1$, $R^1$, $Y^2$, $Y^3$, and $X^4$ are as defined for the compound of formula I.

In embodiment H16 the invention provides compounds of formula I wherein $X^1$ is chloro, $X^2$ is CH, $X^3$ is trifluoromethyl and $R^2$ is 2-(thietan-3-yl)ethanyl and $G^1$, $R^1$, $Y^2$, $Y^3$, and $X^4$ are as defined for the compound of formula I.

In embodiment H17 the invention provides compounds of formula I wherein $X^1$ is chloro, $X^2$ is CH, $X^3$ is trifluoromethyl and $R^2$ is 2-(1,1-dioxothietan-3-yl)ethanyl and $G^1$, $R^1$, $Y^2$, $Y^3$, and $X^4$ are as defined for the compound of formula I.

In embodiment H18 the invention provides compounds of formula I wherein $X^1$ is chloro, $X^2$ is CH, $X^3$ is trifluoromethyl and $R^2$ is 2-(1-oxothietan-3-yl)ethanyl and $G^1$, $R^1$, $Y^2$, $Y^3$, and $X^4$ are as defined for the compound of formula I.

In embodiment H19 the invention provides compounds of formula I wherein $X^1$ is chloro, $X^2$ is CH, $X^3$ is trifluoromethyl and $Y^2$ is CH, $Y^3$ is CH and $G^1$, $R^1$, $R^2$, and $X^4$ are as defined for the compound of formula I.

In embodiment H20 the invention provides compounds of formula I wherein $X^1$ is chloro, $X^2$ is CH, $X^3$ is trifluoromethyl and $Y^2$ is N, $Y^3$ is CH and $G^1$, $R^1$, $R^2$, and $X^4$ are as defined for the compound of formula I.

In embodiment H21 the invention provides compounds of formula I wherein $X^1$ is chloro, $X^2$ is CH, $X^3$ is trifluoromethyl and $Y^2$ is CH, $Y^3$ is N and $G^1$, $R^1$, $R^2$, and $X^4$ are as defined for the compound of formula I.

In embodiment H22 the invention provides compounds of formula I wherein $X^1$ is chloro, $X^2$ is CH, $X^3$ is trifluoromethyl and $X^4$ is trifluoromethyl and $G^1$, $R^1$, $R^2$, $Y^2$ and $Y^3$ are as defined for the compound of formula I.

In embodiment H23 the invention provides compounds of formula I wherein $X^1$ is chloro, $X^2$ is CH, $X^3$ is trifluoromethyl and $X^4$ is difluoromethyl and $G^1$, $R^1$, $R^2$, $Y^2$ and $Y^3$ are as defined for the compound of formula I.

In embodiment H24 the invention provides compounds of formula I wherein $X^1$ is chloro, $X^2$ is CH, $X^3$ is trifluoromethyl and $X^4$ is chlorodifluoromethyl and $G^1$, $R^1$, $R^2$, $Y^2$ and $Y^3$ are as defined for the compound of formula I.

In embodiment J1 the invention provides compounds of formula I wherein $X^1$ is chloro, $X^2$ is CH, $X^3$ is bromo and $R^2$ is thietan-3-yl- and $G^1$, $R^1$, $Y^2$, $Y^3$ and $X^4$ are as defined for the compound of formula I.

In embodiment J2 the invention provides compounds of formula I wherein $X^1$ is chloro, $X^2$ is CH, $X^3$ is bromo and $R^2$ is 1-oxo-thietan-3-yl- and $G^1$, $R^1$, $Y^2$, $Y^3$ and $X^4$ are as defined for the compound of formula I.

In embodiment J3 the invention provides compounds of formula I wherein $X^1$ is chloro, $X^2$ is CH, $X^3$ is bromo and $R^2$ is 1,1-Dioxo-thietan-3-yl- and $G^1$, $R^1$, $Y^2$, $Y^3$ and $X^4$ are as defined for the compound of formula I.

In embodiment J4 the invention provides compounds of formula I wherein $X^1$ is chloro, $X^2$ is CH, $X^3$ is bromo and $R^2$ is 2,2-dimethylthietan-3-yl- and $G^1$, $R^1$, $Y^2$, $Y^3$ and $X^4$ are as defined for the compound of formula I.

In embodiment J5 the invention provides compounds of formula I wherein $X^1$ is chloro, $X^2$ is CH, $X^3$ is bromo and $R^2$ is 2,2-dimethyl-1-oxo-thietan-3-yl- and $G^1$, $R^1$, $Y^2$, $Y^3$ and $X^4$ are as defined for the compound of formula I.

In embodiment J6 the invention provides compounds of formula I wherein $X^1$ is chloro, $X^2$ is CH, $X^3$ is bromo and $R^2$ is 2,2-dimethyl-1,1-Dioxo-thietan-3-yl- and $G^1$, $R^1$, $Y^2$, $Y^3$ and $X^4$ are as defined for the compound of formula I.

In embodiment J7 the invention provides compounds of formula I wherein $X^1$ is chloro, $X^2$ is CH, $X^3$ is bromo and $R^2$ is 3-Methyl-thietan-3-yl- and $G^1$, $R^1$, $Y^2$, $Y^3$ and $X^4$ are as defined for the compound of formula I.

In embodiment J8 the invention provides compounds of formula I wherein $X^1$ is chloro, $X^2$ is CH, $X^3$ is bromo and $R^2$ is 3-Methyl-1-oxo-thietan-3-yl- and $G^1$, $R^1$, $Y^2$, $Y^3$ and $X^4$ are as defined for the compound of formula I.

In embodiment J9 the invention provides compounds of formula I wherein $X^1$ is chloro, $X^2$ is CH, $X^3$ is bromo and $R^2$ is 3-Methyl-1,1-Dioxo-thietan-3-yl- and $G^1$, $R^1$, $Y^2$, $Y^3$ and $X^4$ are as defined for the compound of formula I.

In embodiment J10 the invention provides compounds of formula I wherein $X^1$ is chloro, $X^2$ is CH, $X^3$ is bromo and $R^2$ is thietan-3-ylmethyl- and $G^1$, $R^1$, $Y^2$, $Y^3$ and $X^4$ are as defined for the compound of formula I.

In embodiment J11 the invention provides compounds of formula I wherein $X^1$ is chloro, $X^2$ is CH, $X^3$ is bromo and $R^2$ is 1-oxo-thietan-3-ylmethyl- and $G^1$, $R^1$, $Y^2$, $Y^3$ and $X^4$ are as defined for the compound of formula I.

In embodiment J12 the invention provides compounds of formula I wherein $X^1$ is chloro, $X^2$ is CH, $X^3$ is bromo and $R^2$ is 1,1-Dioxo-thietan-3-ylmethyl- and $G^1$, $R^1$, $Y^2$, $Y^3$ and $X^4$ are as defined for the compound of formula I.

In embodiment J13 the invention provides compounds of formula I wherein $X^1$ is chloro, $X^2$ is CH, $X^3$ is bromo and $R^2$ is thietan-2-ylmethyl- and $G^1$, $R^1$, $Y^2$, $Y^3$ and $X^4$ are as defined for the compound of formula I.

In embodiment J14 the invention provides compounds of formula I wherein $X^1$ is chloro, $X^2$ is CH, $X^3$ is bromo and $R^2$ is (1-oxothietan-2-yl)methyl- and $G^1$, $R^1$, $Y^2$, $Y^3$ and $X^4$ are as defined for the compound of formula I.

In embodiment J15 the invention provides compounds of formula I wherein $X^1$ is chloro, $X^2$ is CH, $X^3$ is bromo and $R^2$ is (1,1-dioxothietan-2-yl)methyl- and $G^1$, $R^1$, $Y^2$, $Y^3$ and $X^4$ are as defined for the compound of formula I.

In embodiment J16 the invention provides compounds of formula I wherein $X^1$ is chloro, $X^2$ is CH, $X^3$ is bromo and $R^2$ is 2-(thietan-3-yl)ethanyl and $G^1$, $R^1$, $Y^2$, $Y^3$ and $X^4$ are as defined for the compound of formula I.

In embodiment J17 the invention provides compounds of formula I wherein $X^1$ is chloro, $X^2$ is CH, $X^3$ is bromo and $R^2$ is 2-(1,1-dioxothietan-3-yl)ethanyl and $G^1$, $R^1$, $Y^2$, $Y^3$ and $X^4$ are as defined for the compound of formula I.

In embodiment J18 the invention provides compounds of formula I wherein $X^1$ is chloro, $X^2$ is CH, $X^3$ is bromo and $R^2$ is 2-(1-oxothietan-3-yl)ethanyl and $G^1$, $R^1$, $Y^2$, $Y^3$ and $X^4$ are as defined for the compound of formula I.

In embodiment J19 the invention provides compounds of formula I wherein $X^1$ is chloro, $X^2$ is CH, $X^3$ is bromo and $Y^2$ is CH, $Y^3$ is CH and $G^1$, $R^1$, $R^2$, and $X^4$ are as defined for the compound of formula I.

In embodiment J20 the invention provides compounds of formula I wherein $X^1$ is chloro, $X^2$ is CH, $X^3$ is bromo and $Y^2$ is N, $Y^3$ is CH and $G^1$, $R^1$, $R^2$, and $X^4$ are as defined for the compound of formula I.

In embodiment J21 the invention provides compounds of formula I wherein $X^1$ is chloro, $X^2$ is CH, $X^3$ is bromo and $Y^2$ is CH, $Y^3$ is N and $G^1$, $R^1$, $R^2$, and $X^4$ are as defined for the compound of formula I.

In embodiment J22 the invention provides compounds of formula I wherein $X^1$ is chloro, $X^2$ is CH, $X^3$ is bromo and $X^4$ is trifluoromethyl and $G^1$, $R^1$, $R^2$, $Y^2$ and $Y^3$ are as defined for the compound of formula I.

In embodiment J23 the invention provides compounds of formula I wherein $X^1$ is chloro, $X^2$ is CH, $X^3$ is bromo and $X^4$ is difluoromethyl and $G^1$, $R^1$, $R^2$, $Y^2$ and $Y^3$ are as defined for the compound of formula I.

In embodiment J24 the invention provides compounds of formula I wherein $X^1$ is chloro, $X^2$ is CH, $X^3$ is bromo and $X^4$ is chlorodifluoromethyl and $G^1$, $R^1$, $R^2$, $Y^2$ and $Y^3$ are as defined for the compound of formula I.

In embodiment K1 the invention provides compounds of formula I wherein $X^1$ is trifluoromethyl, $X^2$ is CH, $X^3$ is trifluoromethyl and $R^2$ is thietan-3-yl- and $G^1$, $R^1$, $Y^2$, $Y^3$ and $X^4$ are as defined for the compound of formula I.

In embodiment K2 the invention provides compounds of formula I wherein $X^1$ is trifluoromethyl, $X^2$ is CH, $X^3$ is trifluoromethyl and $R^2$ is 1-oxo-thietan-3-yl- and $G^1$, $R^1$, $Y^2$, $Y^3$ and $X^4$ are as defined for the compound of formula I.

In embodiment K3 the invention provides compounds of formula I wherein $X^1$ is trifluoromethyl, $X^2$ is CH, $X^3$ is trifluoromethyl and $R^2$ is 1,1-Dioxo-thietan-3-yl- and $G^1$, $R^1$, $Y^2$, $Y^3$ and $X^4$ are as defined for the compound of formula I.

In embodiment K4 the invention provides compounds of formula I wherein $X^1$ is trifluoromethyl, $X^2$ is CH, $X^3$ is trifluoromethyl and $R^2$ is 2,2-dimethylthietan-3-yl- and $G^1$, $R^1$, $Y^2$, $Y^3$ and $X^4$ are as defined for the compound of formula I.

In embodiment K5 the invention provides compounds of formula I wherein $X^1$ is trifluoromethyl, $X^2$ is CH, $X^3$ is trifluoromethyl and $R^2$ is 2,2-dimethyl-1-oxo-thietan-3-yl- and $G^1$, $R^1$, $Y^2$, $Y^3$ and $X^4$ are as defined for the compound of formula I.

In embodiment K6 the invention provides compounds of formula I wherein $X^1$ is trifluoromethyl, $X^2$ is CH, $X^3$ is trifluoromethyl and $R^2$ is 2,2-dimethyl-1,1-Dioxo-thietan-3-yl- and $G^1$, $R^1$, $Y^2$, $Y^3$ and $X^4$ are as defined for the compound of formula I.

In embodiment K7 the invention provides compounds of formula I wherein $X^1$ is trifluoromethyl, $X^2$ is CH, $X^3$ is trifluoromethyl and $R^2$ is 3-Methyl-thietan-3-yl- and $G^1$, $R^1$, $Y^2$, $Y^3$ and $X^4$ are as defined for the compound of formula I.

In embodiment K8 the invention provides compounds of formula I wherein $X^1$ is trifluoromethyl, $X^2$ is CH, $X^3$ is trifluoromethyl and $R^2$ is 3-Methyl-1-oxo-thietan-3-yl- and $G^1$, $R^1$, $Y^2$, $Y^3$ and $X^4$ are as defined for the compound of formula I.

In embodiment K9 the invention provides compounds of formula I wherein $X^1$ is trifluoromethyl, $X^2$ is CH, $X^3$ is trifluoromethyl and $R^2$ is 3-Methyl-1,1-Dioxo-thietan-3-yl- and $G^1$, $R^1$, $Y^2$, $Y^3$ and $X^4$ are as defined for the compound of formula I.

In embodiment K10 the invention provides compounds of formula I wherein $X^1$ is trifluoromethyl, $X^2$ is CH, $X^3$ is trifluoromethyl and $R^2$ is thietan-3-ylmethyl- and $G^1$, $R^1$, $Y^2$, $Y^3$ and $X^4$ are as defined for the compound of formula I.

In embodiment K11 the invention provides compounds of formula I wherein $X^1$ is trifluoromethyl, $X^2$ is CH, $X^3$ is trifluoromethyl and $R^2$ is 1-oxo-thietan-3-ylmethyl- and $G^1$, $R^1$, $Y^2$, $Y^3$ and $X^4$ are as defined for the compound of formula I.

In embodiment K12 the invention provides compounds of formula I wherein $X^1$ is trifluoromethyl, $X^2$ is CH, $X^3$ is trifluoromethyl and $R^2$ is 1,1-Dioxo-thietan-3-ylmethyl- and $G^1$, $R^1$, $Y^2$, $Y^3$ and $X^4$ are as defined for the compound of formula I.

In embodiment K13 the invention provides compounds of formula I wherein $X^1$ is trifluoromethyl, $X^2$ is CH, $X^3$ is trifluoromethyl and $R^2$ is thietan-2-ylmethyl- and $G^1$, $R^1$, $Y^2$, $Y^3$ and $X^4$ are as defined for the compound of formula I.

In embodiment K14 the invention provides compounds of formula I wherein $X^1$ is trifluoromethyl, $X^2$ is CH, $X^3$ is trifluoromethyl and $R^2$ is (1-oxothietan-2-yl)methyl- and $G^1$, $R^1$, $Y^2$, $Y^3$ and $X^4$ are as defined for the compound of formula I.

In embodiment K15 the invention provides compounds of formula I wherein $X^1$ is trifluoromethyl, $X^2$ is CH, $X^3$ is trifluoromethyl and $R^2$ is (1,1-dioxothietan-2-yl)methyl- and $G^1$, $R^1$, $Y^2$, $Y^3$ and $X^4$ are as defined for the compound of formula I.

In embodiment K16 the invention provides compounds of formula I wherein $X^1$ is trifluoromethyl, $X^2$ is CH, $X^3$ is trifluoromethyl and $R^2$ is 2-(thietan-3-yl)ethanyl and $G^1$, $R^1$, $Y^2$, $Y^3$ and $X^4$ are as defined for the compound of formula I.

In embodiment K17 the invention provides compounds of formula I wherein $X^1$ is trifluoromethyl, $X^2$ is CH, $X^3$ is trifluoromethyl and $R^2$ is 2-(1,1-dioxothietan-3-yl)ethanyl and $G^1$, $R^1$, $Y^2$, $Y^3$ and $X^4$ are as defined for the compound of formula I.

In embodiment K18 the invention provides compounds of formula I wherein $X^1$ is trifluoromethyl, $X^2$ is CH, $X^3$ is trifluoromethyl and $R^2$ is 2-(1-oxothietan-3-yl)ethanyl and $G^1$, $R^1$, $Y^2$, $Y^3$ and $X^4$ are as defined for the compound of formula I.

In embodiment K19 the invention provides compounds of formula I wherein $X^1$ is trifluoromethyl, $X^2$ is CH, $X^3$ is trifluoromethyl and $Y^2$ is CH, $Y^3$ is CH and $G^1$, $R^1$, $R^2$, and $X^4$ are as defined for the compound of formula I.

In embodiment K20 the invention provides compounds of formula I wherein $X^1$ is trifluoromethyl, $X^2$ is CH, $X^3$ is trifluoromethyl and $Y^2$ is N, $Y^3$ is CH and $G^1$, $R^1$, $R^2$, and $X^4$ are as defined for the compound of formula I.

In embodiment K21 the invention provides compounds of formula I wherein $X^1$ is trifluoromethyl, $X^2$ is CH, $X^3$ is trifluoromethyl and $Y^2$ is CH, $Y^3$ is N and $G^1$, $R^1$, $R^2$, and $X^4$ are as defined for the compound of formula I.

In embodiment K22 the invention provides compounds of formula I wherein $X^1$ is trifluoromethyl, $X^2$ is CH, $X^3$ is trifluoromethyl and $X^4$ is trifluoromethyl and $G^1$, $R^1$, $R^2$, $Y^2$ and $Y^3$ are as defined for the compound of formula I.

In embodiment K23 the invention provides compounds of formula I wherein $X^1$ is trifluoromethyl, $X^2$ is CH, $X^3$ is trifluoromethyl and $X^4$ is difluoromethyl and $G^1$, $R^1$, $R^2$, $Y^2$ and $Y^3$ are as defined for the compound of formula I.

In embodiment K24 the invention provides compounds of formula I wherein $X^1$ is trifluoromethyl, $X^2$ is CH, $X^3$ is trifluoromethyl and $X^4$ is chlorodifluoromethyl and $G^1$, $R^1$, $R^2$, $Y^2$ and $Y^3$ are as defined for the compound of formula I.

In embodiment L1 the invention provides compounds of formula I wherein $X^1$ is chloro, $X^2$ is CH, $X^3$ is chloro, $Y^2$ is CH, $Y^3$ is CH and $G^1$, $R^1$, $R^2$, and $X^4$ are as defined for the compound of formula I.

In embodiment L2 the invention provides compounds of formula I wherein $X^1$ is chloro, $X^2$ is CH, $X^3$ is chloro, $Y^2$ is N, $Y^3$ is CH and $G^1$, $R^1$, $R^2$, and $X^4$ are as defined for the compound of formula I.

In embodiment L3 the invention provides compounds of formula I wherein $X^1$ is chloro, $X^2$ is CH, $X^3$ is chloro, $Y^2$ is CH, $Y^3$ is N and $G^1$, $R^1$, $R^2$, and $X^4$ are as defined for the compound of formula I.

In embodiment L4 the invention provides compounds of formula I wherein $X^1$ is chloro, $X^2$ is C—F, $X^3$ is hydrogen, $Y^2$ is CH, $Y^3$ is CH and $G^1$, $R^1$, $R^2$, and $X^4$ are as defined for the compound of formula I.

In embodiment L5 the invention provides compounds of formula I wherein $X^1$ is chloro, $X^2$ is C—F, $X^3$ is hydrogen, $Y^2$ is N, $Y^3$ is CH and $G^1$, $R^1$, $R^2$, and $X^4$ are as defined for the compound of formula I.

In embodiment L6 the invention provides compounds of formula I wherein $X^1$ is chloro, $X^2$ is C—F, $X^3$ is hydrogen, $Y^2$ is CH, $Y^3$ is N and $G^1$, $R^1$, $R^2$, and $X^4$ are as defined for the compound of formula I.

In embodiment L7 the invention provides compounds of formula I wherein $X^1$ is fluoro, $X^2$ is C—Cl, $X^3$ is hydrogen, $Y^2$ is CH, $Y^3$ is CH and $G^1$, $R^1$, $R^2$, and $X^4$ are as defined for the compound of formula I.

In embodiment L8 the invention provides compounds of formula I wherein $X^1$ is fluoro, $X^2$ is C—Cl, $X^3$ is hydrogen, $Y^2$ is N, $Y^3$ is CH and $G^1$, $R^1$, $R^2$, and $X^4$ are as defined for the compound of formula I.

In embodiment L9 the invention provides compounds of formula I wherein $X^1$ is fluoro, $X^2$ is C—Cl, $X^3$ is hydrogen, $Y^2$ is CH, $Y^3$ is N and $G^1$, $R^1$, $R^2$, and $X^4$ are as defined for the compound of formula I.

In embodiment L10 the invention provides compounds of formula I wherein $X^1$ is chloro, $X^2$ is C—Cl, $X^3$ is hydrogen, $Y^2$ is CH, $Y^3$ is CH and $G^1$, $R^1$, $R^2$, and $X^4$ are as defined for the compound of formula I.

In embodiment L11 the invention provides compounds of formula I wherein $X^1$ is chloro, $X^2$ is C—Cl, $X^3$ is hydrogen, $Y^2$ is N, $Y^3$ is CH and $G^1$, $R^1$, $R^2$, and $X^4$ are as defined for the compound of formula I.

In embodiment L12 the invention provides compounds of formula I wherein $X^1$ is chloro, $X^2$ is C—Cl, $X^3$ is hydrogen, $Y^2$ is CH, $Y^3$ is N and $G^1$, $R^1$, $R^2$, and $X^4$ are as defined for the compound of formula I.

In embodiment L13 the invention provides compounds of formula I wherein $X^1$ is chloro, $X^2$ is C—F, $X^3$ is chloro, $Y^2$ is CH, $Y^3$ is CH and $G^1$, $R^1$, $R^2$, and $X^4$ are as defined for the compound of formula I.

In embodiment L14 the invention provides compounds of formula I wherein $X^1$ is chloro, $X^2$ is C—F, $X^3$ is chloro, $Y^2$ is N, $Y^3$ is CH and $G^1$, $R^1$, $R^2$, and $X^4$ are as defined for the compound of formula I.

In embodiment L15 the invention provides compounds of formula I wherein $X^1$ is chloro, $X^2$ is C—F, $X^3$ is chloro, is CH, $Y^3$ is N and $G^1$, $R^1$, $R^2$, and $X^4$ are as defined for the compound of formula I.

In embodiment L16 the invention provides compounds of formula I wherein $X^1$ is chloro, $X^2$ is C—Cl, $X^3$ is chloro, $Y^2$ is CH, $Y^3$ is CH and $G^1$, $R^1$, $R^2$, and $X^4$ are as defined for the compound of formula I.

In embodiment L17 the invention provides compounds of formula I wherein $X^1$ is chloro, $X^2$ is C—Cl, $X^3$ is chloro, $Y^2$ is N, $Y^3$ is CH and $G^1$, $R^1$, $R^2$, and $X^4$ are as defined for the compound of formula I.

In embodiment L18 the invention provides compounds of formula I wherein $X^1$ is chloro, $X^2$ is C—Cl, $X^3$ is chloro, $Y^2$ is CH, $Y^3$ is N and $G^1$, $R^1$, $R^2$, and $X^4$ are as defined for the compound of formula I.

In embodiment L19 the invention provides compounds of formula I wherein $X^1$ is chloro, $X^2$ is C—Br, $X^3$ is chloro, $Y^2$ is CH, $Y^3$ is CH and $G^1$, $R^1$, $R^2$, and $X^4$ are as defined for the compound of formula I.

In embodiment L20 the invention provides compounds of formula I wherein $X^1$ is chloro, $X^2$ is C—Br, $X^3$ is chloro, $Y^2$ is N, $Y^3$ is CH and $G^1$, $R^1$, $R^2$, and $X^4$ are as defined for the compound of formula I.

In embodiment L21 the invention provides compounds of formula I wherein $X^1$ is chloro, $X^2$ is C—Br, $X^3$ is chloro, $Y^2$ is CH, $Y^3$ is N and $G^1$, $R^1$, $R^2$, and $X^4$ are as defined for the compound of formula I.

In embodiment L22 the invention provides compounds of formula I wherein $X^1$ is chloro, $X^2$ is C—I, $X^3$ is chloro, $Y^2$ is CH, $Y^3$ is CH and $G^1$, $R^1$, $R^2$, and $X^4$ are as defined for the compound of formula I.

In embodiment L23 the invention provides compounds of formula I wherein $X^1$ is chloro, $X^2$ is C—I, $X^3$ is chloro, $Y^2$ is N, $Y^3$ is CH and $G^1$, $R^1$, $R^2$, and $X^4$ are as defined for the compound of formula I.

In embodiment L24 the invention provides compounds of formula I wherein $X^1$ is chloro, $X^2$ is C—I, $X^3$ is chloro, $Y^2$ is CH, $Y^3$ is N and $G^1$, $R^1$, $R^2$, and $X^4$ are as defined for the compound of formula I.

In embodiment L25 the invention provides compounds of formula I wherein $X^1$ is fluoro, $X^2$ is C—F, $X^3$ is fluoro, $Y^2$ is CH, $Y^3$ is CH and $G^1$, $R^1$, $R^2$, and $X^4$ are as defined for the compound of formula I.

In embodiment L26 the invention provides compounds of formula I wherein $X^1$ is fluoro, $X^2$ is C—F, $X^3$ is fluoro, $Y^2$ is N, $Y^3$ is CH and $G^1$, $R^1$, $R^2$, and $X^4$ are as defined for the compound of formula I.

In embodiment L27 the invention provides compounds of formula I wherein $X^1$ is fluoro, $X^2$ is C—F, $X^3$ is fluoro, $Y^2$ is CH, $Y^3$ is N and $G^1$, $R^1$, $R^2$, and $X^4$ are as defined for the compound of formula I.

In embodiment L28 the invention provides compounds of formula I wherein $X^1$ is chloro, $X^2$ is CH, $X^3$ is bromo, $Y^2$ is CH, $Y^3$ is CH and $G^1$, $R^1$, $R^2$, and $X^4$ are as defined for the compound of formula I.

In embodiment L29 the invention provides compounds of formula I wherein $X^1$ is chloro, $X^2$ is CH, $X^3$ is bromo, $Y^2$ is N, $Y^3$ is CH and $G^1$, $R^1$, $R^2$, and $X^4$ are as defined for the compound of formula I.

In embodiment L30 the invention provides compounds of formula I wherein $X^1$ is chloro, $X^2$ is CH, $X^3$ is bromo, $Y^2$ is CH, $Y^3$ is N and $G^1$, $R^1$, $R^2$, and $X^4$ are as defined for the compound of formula I.

In embodiment L31 the invention provides compounds of formula I wherein $X^1$ is chloro, $X^2$ is CH, $X^3$ is fluoro, $Y^2$ is CH, $Y^3$ is CH and $G^1$, $R^1$, $R^2$, and $X^4$ are as defined for the compound of formula I.

In embodiment L32 the invention provides compounds of formula I wherein $X^1$ is chloro, $X^2$ is CH, $X^3$ is fluoro, $Y^2$ is N, $Y^3$ is CH and $G^1$, $R^1$, $R^2$, and $X^4$ are as defined for the compound of formula I.

In embodiment L33 the invention provides compounds of formula I wherein $X^1$ is chloro, $X^2$ is CH, $X^3$ is fluoro, $Y^2$ is CH, $Y^3$ is N and $G^1$, $R^1$, $R^2$, and $X^4$ are as defined for the compound of formula I.

In embodiment L34 the invention provides compounds of formula I wherein $X^1$ is chloro, $X^2$ is CH, $X^3$ is trifluoromethyl, $Y^2$ is CH, $Y^3$ is CH and $G^1$, $R^1$, $R^2$, and $X^4$ are as defined for the compound of formula I.

In embodiment L35 the invention provides compounds of formula I wherein $X^1$ is chloro, $X^2$ is CH, $X^3$ is trifluoromethyl, $Y^2$ is N, $Y^3$ is CH and $G^1$, $R^1$, $R^2$, and $X^4$ are as defined for the compound of formula I.

In embodiment L36 the invention provides compounds of formula I wherein $X^1$ is chloro, $X^2$ is CH, $X^3$ is trifluoromethyl, $Y^2$ is CH, $Y^3$ is N and $G^1$, $R^1$, $R^2$, and $X^4$ are as defined for the compound of formula I.

In embodiment L37 the invention provides compounds of formula I wherein $X^1$ is chloro, $X^2$ is C—Cl, $X^3$ is trifluoromethyl, $Y^2$ is CH, $Y^3$ is CH and $G^1$, $R^1$, $R^2$, and $X^4$ are as defined for the compound of formula I.

In embodiment L38 the invention provides compounds of formula I wherein $X^1$ is chloro, $X^2$ is C—Cl, $X^3$ is trifluoromethyl, $Y^2$ is N, $Y^3$ is CH and $G^1$, $R^1$, $R^2$, and $X^4$ are as defined for the compound of formula I.

In embodiment L39 the invention provides compounds of formula I wherein $X^1$ is chloro, $X^2$ is C—Cl, $X^3$ is trifluoromethyl, $Y^2$ is N, $Y^3$ is CH and $G^1$, $R^1$, $R^2$, and $X^4$ are as defined for the compound of formula I.

In embodiment L40 the invention provides compounds of formula I wherein $X^1$ is trifluoromethyl, $X^2$ is CH, $X^3$ is trifluoromethyl, $Y^2$ is CH, $Y^3$ is CH and $G^1$, $R^1$, $R^2$, and $X^4$ are as defined for the compound of formula I.

In embodiment L41 the invention provides compounds of formula I wherein $X^1$ is trifluoromethyl, $X^2$ is CH, $X^3$ is trifluoromethyl, $Y^2$ is N, $Y^3$ is CH and $G^1$, $R^1$, $R^2$, and $X^4$ are as defined for the compound of formula I.

In embodiment L42 the invention provides compounds of formula I wherein $X^1$ is trifluoromethyl, $X^2$ is CH, $X^3$ is trifluoromethyl, $Y^2$ is CH, $Y^3$ is N and $G^1$, $R^1$, $R^2$, and $X^4$ are as defined for the compound of formula I.

In embodiment L43 the invention provides compounds of formula I wherein $X^1$ is trifluoromethyl, $X^2$ is C—Cl, $X^3$ is trifluoromethyl, $Y^2$ is CH, $Y^3$ is CH and $G^1$, $R^1$, $R^2$, and $X^4$ are as defined for the compound of formula I.

In embodiment L44 the invention provides compounds of formula I wherein $X^1$ is trifluoromethyl, $X^2$ is C—Cl, $X^3$ is trifluoromethyl, $Y^2$ is N, $Y^3$ is CH and $G^1$, $R^1$, $R^2$, and $X^4$ are as defined for the compound of formula I.

In embodiment L45 the invention provides compounds of formula I wherein $X^1$ is trifluoromethyl, $X^2$ is C—Cl, $X^3$ is trifluoromethyl, $Y^2$ is CH, $Y^3$ is N and $G^1$, $R^1$, $R^2$, and $X^4$ are as defined for the compound of formula I.

In embodiment L46 the invention provides compounds of formula I wherein $X^1$ is trifluoromethyl, $X^2$ is CH, $X^3$ is hydrogen, $Y^2$ is CH, $Y^3$ is CH and $G^1$, $R^1$, $R^2$, and $X^4$ are as defined for the compound of formula I.

In embodiment L47 the invention provides compounds of formula I wherein $X^1$ is trifluoromethyl, $X^2$ is CH, $X^3$ is hydrogen, $Y^2$ is N, $Y^3$ is CH and $G^1$, $R^1$, $R^2$, and $X^4$ are as defined for the compound of formula I.

In embodiment L48 the invention provides compounds of formula I wherein $X^1$ is trifluoromethyl, $X^2$ is CH, $X^3$ is hydrogen, $Y^2$ is CH, $Y^3$ is N and $G^1$, $R^1$, $R^2$, and $X^4$ are as defined for the compound of formula I.

In embodiment L49 the invention provides compounds of formula I wherein $X^1$ is chloro, $X^2$ is N, $X^3$ is chloro, $Y^2$ is CH, $Y^3$ is CH and $G^1$, $R^1$, $R^2$, and $X^4$ are as defined for the compound of formula I.

In embodiment L50 the invention provides compounds of formula I wherein $X^1$ is chloro, $X^2$ is N, $X^3$ is chloro, $Y^2$ is N, $Y^3$ is CH and $G^1$, $R^1$, $R^2$, and $X^4$ are as defined for the compound of formula I.

In embodiment L51 the invention provides compounds of formula I wherein $X^1$ is chloro, $X^2$ is N, $X^3$ is chloro, $Y^2$ is CH, $Y^3$ is N and $G^1$, $R^1$, $R^2$, and $X^4$ are as defined for the compound of formula I.

In embodiment L52 the invention provides compounds of formula I wherein $X^1$ is trifluoromethyl, $X^2$ is N, $X^3$ is trifluoromethyl, $Y^2$ is CH, $Y^3$ is CH and $G^1$, $R^1$, $R^2$, and $X^4$ are as defined for the compound of formula I.

In embodiment L53 the invention provides compounds of formula I wherein $X^1$ is trifluoromethyl, $X^2$ is N, $X^3$ is trifluoromethyl, $Y^2$ is N, $Y^3$ is CH and $G^1$, $R^1$, $R^2$, and $X^4$ are as defined for the compound of formula I.

In embodiment L54 the invention provides compounds of formula I wherein $X^1$ is trifluoromethyl, $X^2$ is N, $X^3$ is trifluoromethyl, $Y^2$ is CH, $Y^3$ is N and $G^1$, $R^1$, $R^2$, and $X^4$ are as defined for the compound of formula I.

In a further aspect the invention provides a method of controlling insects, acarines, nematodes or molluscs, preferably those described below, and preferably in a crop of useful plants, which comprises applying to a pest, to a locus of a pest, or to a plant susceptible to attack by a pest an insecticidally, acaricidally, nematicidally or molluscicidally effective amount of a compound of formula IA

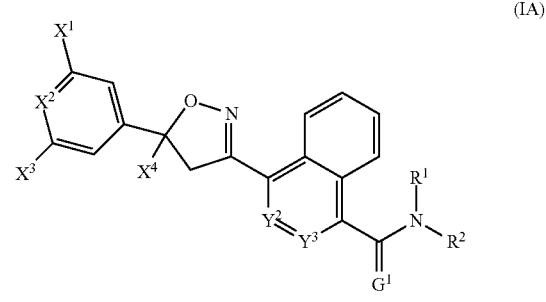
(IA)

wherein
$G^1$ is oxygen;
$R^1$ is hydrogen;
$R^2$ is thietan-3-yl-, 1-oxo-thietan-3-yl-, 1,1-dioxo-thietan-3-yl-, thietan-3-ylmethyl-, 1-oxo-thietan-3-ylmethyl-, or 1,1-dioxo-thietan-3-ylmethyl-;
$Y^1$, $Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;
$X^2$ is C—$X^6$;
$X^1$, $X^3$ and $X^6$ are independently halogen or trihalomethyl;

$X^4$ is trifluoromethyl, difluoromethyl or chlorodifluoromethyl.

preferably with the provisos that:

when the compound is a compound wherein $Y^1$, $Y^2$ and $Y^3$ are CH; $R^5$ is methyl; $X^1$ is chloro, $X^2$ is C—Cl, $X^3$ is chloro, or $X^1$ is chloro, $X^2$ is C—F, $X^3$ is chloro, or $X^1$ is chloro, $X^2$ is C—Br, $X^3$ is chloro, or $X^1$ is chloro, $X^2$ is C—Cl, $X^3$ is trifluoromethyl, or $X^1$ is trifluoromethyl, $X^2$ is C—Cl, $X^3$ is trifluoromethyl, or $X^1$ is fluoro, $X^2$ is C—F, $X^3$ is fluoro, and $X^4$ is $CF_3$, then the method does not comprise applying the compound of formula I to a crop of soybean plants, the locus thereof, or propagation material thereof, and the method is not for control of stinkbugs; and/or wherein the compound is not a compound wherein $R^2$ is thietan-3-yl-, 1-oxo-thietan-3-yl-, 1,1-Dioxo-thietan-3-yl-; $Y^1$, $Y^2$ and $Y^3$ are CH; $R^5$ is methyl; $X^2$ is bromo, $X^2$ is C—Cl, $X^3$ is bromo and $X^4$ is $CF_3$.

In a further aspect the invention provides a method of protecting useful plants from insects, acarines, nematodes or molluscs, preferably those described below, comprising applying to said plant, to the locus thereof, or to plant propagation material thereof, an insecticidally, acaricidally, nematicidally or molluscicidally effective amount of a compound of formula IA as defined above, including preferences thereof.

Optionally, said methods do not comprise applying the compound of formula IA to a crop of soybean plants, the locus thereof, or propagation material thereof, and the method is not for control of stinkbugs.

Preferred values of $R^2$, $R^5$, $Y^1$, $Y^2$, $Y^3$, $X^1$, $X^2$, $X^3$, $X^4$, $X^5$ and $X^6$ for the compound of formula IA are, in any combination, as set out below.

Preferably $R^2$ is thietan-3-yl-, 1-oxo-thietan-3-yl-, or 1,1-dioxo-thietan-3-yl-.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, even more preferably $R^5$ is chloro, bromo, fluoro, methyl, trifluoromethyl. Most preferably $R^5$ is chloro or methyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. More preferably $Y^1$ is CH, $Y^2$ is CH, $Y^3$ is CH.

Preferably $X^1$ is chloro, $X^2$ is C—Br, $X^3$ is chloro, or $X^1$ is chloro, $X^2$ is C—F, $X^3$ is chloro, or $X^1$ is chloro, $X^2$ is C—Cl, $X^3$ is chloro, or $X^1$ is chloro, $X^2$ is C—I, $X^3$ is chloro, or $X^1$ is fluoro, $X^2$ is C—F, $X^3$ is fluoro, or $X^1$ is chloro, $X^2$ is C—Cl, $X^3$ is trifluoromethyl, or $X^1$ is trifluoromethyl, $X^2$ is C—Cl, $X^3$ is trifluoromethyl. More preferably $X^1$ is chloro, $X^2$ is C—Cl, $X^3$ is chloro, or $X^1$ is chloro, $X^2$ is C—F, $X^3$ is chloro.

Preferably $X^4$ is trifluoromethyl.

In one embodiment the invention provides compounds of formula IA wherein $G^1$ is oxygen;

$R^1$ is hydrogen;

$R^2$ is thietan-3-yl-, 1-oxo-thietan-3-yl-, 1,1-Dioxo-thietan-3-yl-, thietan-3-ylmethyl-, 1-oxo-thietan-3-ylmethyl-, or 1,1-Dioxo-thietan-3-ylmethyl-;

$Y^1$ is CH, $Y^2$ is CH, $Y^3$ is CH;

$X^1$ is chloro, $X^2$ is C—Cl, $X^3$ is chloro, or $X^1$ is chloro, $X^2$ is C—F, $X^3$ is chloro; and $X^4$ is trifluoromethyl.

In another embodiment the invention provides compounds of formula I wherein $G^1$ is oxygen;

$R^1$ is hydrogen;

$R^2$ is thietan-3-yl-, 1-oxo-thietan-3-yl-, 1,1-Dioxo-thietan-3-yl-;

$Y^1$ is CH, $Y^2$ is CH, $Y^3$ is CH;

$X^1$ is chloro, $X^2$ is C—Cl, $X^3$ is chloro, or $X^1$ is chloro, $X^2$ is C—F, $X^3$ is chloro; and $X^4$ is trifluoromethyl.

In embodiment the invention provides compounds of formula IA wherein $X^1$ is chloro, $X^2$ is C—Br, $X^3$ is chloro and $G^1$, $R^1$, $R^2$, $Y^1$, $Y^2$, $Y^3$ and $X^4$ are as defined for the compound of formula IA.

In embodiment the invention provides compounds of formula IA wherein $X^1$ is chloro, $X^2$ is C—F, $X^3$ is chloro and $G^1$, $R^1$, $R^2$, $Y^1$, $Y^2$, $Y^3$ and $X^4$ are as defined for the compound of formula IA.

In embodiment the invention provides compounds of formula IA wherein $X^1$ is chloro, $X^2$ is C—Cl, $X^3$ is chloro and $G^1$, $R^1$, $R^2$, $Y^1$, $Y^2$, $Y^3$ and $X^4$ are as defined for the compound of formula IA.

In embodiment the invention provides compounds of formula IA wherein $X^1$ is chloro, $X^2$ is C—I, $X^3$ is chloro and $G^1$, $R^1$, $R^2$, $Y^1$, $Y^2$, $Y^3$ and $X^4$ are as defined for the compound of formula IA.

In embodiment the invention provides compounds of formula IA wherein $X^1$ is fluoro, $X^2$ is C—F, $X^3$ is fluoro and $G^1$, $R^1$, $R^2$, $Y^1$, $Y^2$, $Y^3$ and $X^4$ are as defined for the compound of formula IA.

In embodiment the invention provides compounds of formula IA wherein $X^1$ is chloro, $X^2$ is C—Cl, $X^3$ is trifluoromethyl and $G^1$, $R^1$, $R^2$, $Y^1$, $Y^2$, $Y^3$ and $X^4$ are as defined for the compound of formula IA.

In embodiment the invention provides compounds of formula IA wherein $X^1$ is trifluoromethyl, $X^2$ is C—Cl, $X^3$ is trifluoromethyl and $G^1$, $R^1$, $R^2$, $Y^1$, $Y^2$, $Y^3$ and $X^4$ are as defined for the compound of formula IA.

In one embodiment the invention provides a compound of formula IA for use in controlling and/or preventing insects of the family Curculionidae, preferably in for use in controlling and/or preventing *Anthonomus grandis*.

Additional examples of insects from the family of Curculionidae are *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasclBtus*, and *Anthonomus tenebrosus*.

In one embodiment the invention provides a compound of formula IA for use against *Anthonomus grandis* in cotton.

In one embodiment the invention provides a compound of formula IA for use in controlling and/or preventing soil pests.

In one embodiment the invention provides a compound of formula IA for use in controlling and/or preventing corn rootworm, in particular for use against corn root worm from the genus *DlBbrotica*.

In one embodiment the invention provides a compound of formula IA for use in controlling and/or preventing *Diabrotica virgifera*.

In one embodiment the invention provides a compound of formula IA for use in controlling and/or preventing *Diabrotica barberi*.

In one embodiment the invention provides a compound of formula IA for use in controlling and/or preventing *Diabrotica undecimpunctata howardi*.

In one embodiment the invention provides a compound of formula IA for use in controlling and/or preventing wireworms, in particular *Agriotes* spp.

In one embodiment the invention provides a compound of formula IA for use in controlling and/or preventing *Agriotes* spp. in cereals, potato or corn.

Additional examples of *Agriotes* spp. include *Agriotes lineatus, Agriotes obscurus, Agriotes brevis, Agriotes gurgistanus, Agriotes sputator, Agriotes ustulatus, Ctenicera destructor*, and *Limonius californicus*.

In one embodiment the invention provides a compound of formula IA for use in controlling and/or preventing grubs, in particular white grubs.

In one embodiment the invention provides a compound of formula IA for use in controlling and/or preventing *Phyllophaga* spp., particularly on corn, soybean or cotton.

In one embodiment the invention provides a compound of formula IA for use in controlling and/or preventing *Diloboderus* spp. particularly on corn, soybean or cotton.

In one embodiment the invention provides a compound of formula IA for use in controlling and/or preventing *Popillia japonica*, particularly on corn, soybean or cotton.

Additional examples of white grubs include *Phyllophaga anxia, Phyllophaga crinite, Phyllophaga subnitida, Diloboderus abderus*.

In one embodiment the invention provides a compound of formula IA for use in controlling and/or preventing termites, e.g. on sugarcane.

Examples of termites include *Reticulitermes, Coptotermes, Macrotermes, Microtermes, Globitermes*. Specific of subterranean termites include *Reticulitermes flavipes, Reticulitermes hesperus, Reticulitermes verginicus, Reticulitermes hageni, Reticulitermes speratus, Reticulitermes lucifugus, Heterotermes aureus, Coptotermes formosanus, Coptotermes acinaciformis, Coptotermes curvignathus, Nasutitermes exitiosus, Nasutitermes walkeri, Mastotermes darwiniensis, Schedorhinotermes* spp, *Macrotermes bellicosus, Macrotermes* spp., *Globitermes sulphureus, Odontotermes* spp. Specific examples of dry wood termites include *Incisitermes minor, Marginitermes hubbardi, Cryptotermes brevis, Kalotermes flavicollis*. Additional examples of termites include *procornitermes* spp. and *procornitermes araujoi*

In one embodiment the invention provides a compound of formula IA for use in controlling and/or preventing subterraneous stinkbugs, e.g. *Scaptocoris* spp.

In one embodiment the invention provides a compound of formula IA for use in controlling and/or preventing *Scaptocoris castaneus*, in particular on cereals, soybean or corn.

In one embodiment the invention provides a compound of formula IA for use in controlling and/or preventing cutworms, e.g. *agrotis* spp.

In one embodiment the invention provides a compound of formula IA for use in controlling and/or preventing *Agrotis ipsilon*, particularly on cereals, canola, soybean or corn.

In one embodiment the invention provides a compound of formula IA for use in controlling and/or preventing millipedes, e.g. *Julus* spp.

In one embodiment the invention provides a compound of formula IA for use in controlling and/or preventing *Julus* spp., particularly on cereals, canola, soybean & corn.

In one embodiment the invention provides a compound of formula IA for use in controlling and/or preventing broca gigante, e.g. *Telchin licus*, particularly on sugarcane.

In one embodiment the invention provides a compound of formula IA for use in controlling and/or preventing whitefly.

In one embodiment the invention provides a compound of formula IA for use in controlling and/or preventing *Bemisia tabaci*, particularly on vegetables, cotton, soybean, or potatoes.

In one embodiment the invention provides a compound of formula IA for use in controlling and/or preventing *Trialeurodes vaporariorum*, particularly on vegetables, cotton, soybean, or potatoes.

In one embodiment the invention provides a compound of formula IA for use in controlling and/or preventing stinkbugs, in particular *Euschistus* spp.

In one embodiment the invention provides a compound of formula IA for use in controlling and/or preventing *Euschistus* spp., particularly in soybean.

Examples of stinkbugs include *Nezara* spp. (e.g. *Nezara viridula, Nezara antennata, Nezara hilare*), *Piezodorus* spp. (e.g. *Piezodorus guildinii*), *Acrosternum* spp. *Euschistus* spp. (e.g. *Euschistus heros, Euschistus servus*), *Halyomorpha halys, Plautia crossota, Riptortus clavatus, Rhopalus msculatus, Antestiopsis orbitalus, Dichelops* spp. (e.g. *Dichelops furcatus, Dichelops melacanthus*), *Eurygaster* spp. (e.g. *Eurygaster intergriceps, Eurygaster maura*), *Oebalus* spp. (e.g. *Oebalus mexicana, Oebalus poecilus, Oebalus pugnase, Scotinophara* spp. (e.g. *Scotinophara lurida, Scotinophara coarctata*). Preferred targets include *Antestiopsis orbitalus, Dichelops furcatus, Dichelops melacanthus, Euchistus heros, Euschistus servus, Nezara viridula, Nezara hilare, Piezodorus guildinii, Halyomorpha halys*. In one embodiment the stinkbug target is *Nezara viridula, Piezodorus* spp., *Acrosternum* spp, *Euchistus heros*.

In one embodiment the invention provides a compound of formula IA for use against rice pests.

In one embodiment the invention provides a compound of formula IA for use against stemborer, particularly in rice.

Examples of stemborers include *Chilo* sp, *Chilo suppressalis, Chilo polychrysus, Chilo auricilius, Scirpophaga* spp., *Scirpophaga incertulas, Scirpophaga innotata, Scirpophaga nivella Sesamia* sp, *Sesamia inferens*.

In one embodiment the invention provides a compound of formula IA for use against leaffolder, particularly in rice.

Examples of leaffolders include *Cnaphalocrocis* spp., *Cnaphalocrocis medinalis, Marasmia* spp., *Marasmia patnalis, Marasmia exigua*.

In one embodiment the invention provides a compound of formula IA for use against hoppers, particularly in rice.

Examples of Hoppers include *Nephotettix* spp., *Nephotettix virescens, Nephotettix nigropictus, Nephotettix malayanus, Nephotettix cincticeps, Nilaparvata lugens, Sogatella furcifera*.

In one embodiment the invention provides a compound of formula IA for use against gallmidge, particularly in rice.

Examples of Gall midge include *Orseolia* sp, *Orseolia oryzae*.

In one embodiment the invention provides a compound of formula IA for use against whorl maggot, particularly in rice.

Examples of whorl maggots include *Hydrellia* sp, *Hydrellia philippina*.

In one embodiment the invention provides a compound of formula IA for use against Rice bugs, particularly in rice.

Examples of rice bugs include *Leptocorisa* sp, *Leptocorisa oratorius, Leptocorisa chinensis, Leptocorisa acuta*.

In one embodiment the invention provides a compound of formula IA for use against Black bugs, particularly in rice.

Examples of Black bugs include *Scotinophara* sp, *Scotinophara coarctata*, *Scotinophara lurida*, *Scotinophara latiuscula*.

In one embodiment the invention provides a compound of formula IA for use against *plutella* spp.

In one embodiment the invention provides a compound of formula IA for use against *Plutella xylostella*, particularly in *brassica* crops.

In a further aspect the invention provides a method of controlling insects, acarines, nematodes or molluscs, preferably in a crop of useful plants, which comprises applying to a pest, to a locus of a pest, or to a plant susceptible to attack by a pest an insecticidally, acaricidally, nematicidally or molluscicidally effective amount of a compound of formula (IB)

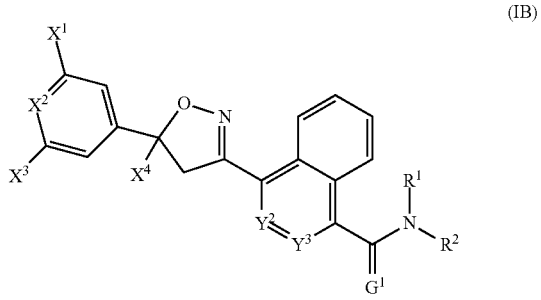

(IB)

wherein
$G^1$ is oxygen;
$R^1$ is hydrogen;
$R^2$ is thietan-3-ylmethyl-, 1-oxo-thietan-3-ylmethyl-, 1,1-dioxo-thietan-3-ylmethyl-;
$Y^1$, $Y^2$ and $Y^3$ are independently CH or nitrogen;
wherein no more than two of $Y^1$, $Y^2$ and $Y^3$ are nitrogen and wherein $Y^2$ and $Y^3$ are not both nitrogen;
$X^2$ is C—$X^6$ or nitrogen;
$X^1$, $X^3$ and $X^6$ are independently hydrogen, halogen or trihalomethyl, wherein at least two of $X^1$, $X^3$ and $X^6$ are not hydrogen;
$X^4$ is trifluoromethyl, difluoromethyl or chlorodifluoromethyl; preferably with the proviso that:
when the compound is a compound wherein $Y^1$, $Y^2$ and $Y^3$ are CH; $R^5$ is methyl; $X^1$ is chloro, $X^2$ is CH, $X^3$ is chloro, or $X^1$ is chloro, $X^2$ is C—F, $X^3$ is hydrogen, or $X^1$ is fluoro, $X^2$ is C—Cl, $X^3$ is hydrogen, or $X^1$ is chloro, $X^2$ is C—Cl, $X^3$ is hydrogen, or $X^1$ is chloro, $X^2$ is CH, $X^3$ is bromo, or $X^1$ is chloro, $X^2$ is CH, $X^3$ is fluoro, or $X^1$ is chloro, $X^2$ is CH, $X^3$ is trifluoromethyl, or $X^1$ is trifluoromethyl, $X^2$ is C—H, $X^3$ is trifluoromethyl, or $X^1$ is trifluoromethyl, $X^2$ is CH, $X^3$ is hydrogen, or $X^1$ is chloro, $X^2$ is C—Cl, $X^3$ is chloro, or $X^1$ is chloro, $X^2$ is C—F, $X^3$ is chloro, or $X^1$ is chloro, $X^2$ is C—Br, $X^3$ is chloro, or $X^1$ is fluoro, $X^2$ is C—F, $X^3$ is fluoro; or $X^1$ is chloro, $X^2$ is C—Cl, $X^3$ is trifluoromethyl, or $X^1$ is trifluoromethyl, $X^2$ is C—Cl, $X^3$ is trifluoromethyl, and $X^4$ is $CF_3$, then the method does not comprise applying the compound of formula I to a crop of soybean plants, the locus thereof, or propagation material thereof, and the method is not for control of stinkbugs.

Optionally when the compound of formula IB is a compound wherein $Y^1$, $Y^2$ and $Y^3$ are CH; $R^5$ is chloro, $X^1$ is chloro, $X^2$ is CH, $X^3$ is chloro, and $X^4$ is trifluoromethyl, then the method does not comprise applying the compound of formula IB to a crop of soybean plants, the locus thereof, or propagation material thereof, and the method is not for control of stinkbugs.

In a further aspect the invention provides a method of protecting useful plants from insects, acarines, nematodes or molluscs, comprising applying to said plant, to the locus thereof, or to plant propagation material thereof, an insecticidally, acaricidally, nematicidally or molluscicidally effective amount of a compound of formula IB as defined above, including preferences thereof.

Optionally, said methods do not comprise applying the compound of formula IB to a crop of soybean plants, the locus thereof, or propagation material thereof, and the method is not for control of stinkbugs.

Preferred values of $R^2$, $Y^1$, $Y^2$, $Y^3$, $X^1$, $X^2$, $X^3$, $X^4$, $X^5$ and $X^6$ for compounds of formula IB are, in any combination, as set out below.

Preferably $R^5$ is hydrogen, chloro, bromo, fluoro, trifluoromethyl, methyl, ethyl, methoxy, nitro, trifluoromethoxy, cyano, cyclopropyl, more preferably $R^5$ is hydrogen, chloro, bromo, fluoro, trifluoromethyl, methyl, ethyl, nitro, cyano, cyclopropyl, even more preferably $R^5$ is chloro, bromo, fluoro, methyl, trifluoromethyl. Most preferably $R^5$ is chloro or methyl.

Preferably $Y^1$ is CH, $Y^2$ is CH, $Y^3$ is CH, or $Y^1$ is N, $Y^2$ is CH, $Y^3$ is CH, or $Y^1$ is N, $Y^2$ is N, $Y^3$ is CH, or $Y^1$ is CH, $Y^2$ is N, $Y^3$ is CH, or $Y^1$ is CH, $Y^2$ is CH, $Y^3$ is N. More preferably $Y^1$ is CH, $Y^2$ is CH, $Y^3$ is CH.

Preferably $X^1$ is chloro, $X^2$ is CH, $X^3$ is chloro, or $X^1$ is chloro, $X^2$ is C—F, $X^3$ is hydrogen, or $X^1$ is fluoro, $X^2$ is C—Cl, $X^3$ is hydrogen, or $X^1$ is chloro, $X^2$ is C—Cl, $X^3$ is hydrogen, or $X^1$ is chloro, $X^2$ is C—Br, $X^3$ is chloro, or $X^1$ is chloro, $X^2$ is C—F, $X^3$ is chloro, or $X^1$ is chloro, $X^2$ is C—Cl, $X^3$ is chloro, or $X^1$ is chloro, $X^2$ is C—I, $X^3$ is chloro, or $X^1$ is fluoro, $X^2$ is C—F, $X^3$ is fluoro, or $X^1$ is chloro, $X^2$ is CH, $X^3$ is bromo, or $X^1$ is chloro, $X^2$ is CH, $X^3$ is fluoro, or $X^1$ is chloro, $X^2$ is CH, $X^3$ is trifluoromethyl, or $X^1$ is chloro, $X^2$ is C—Cl, $X^3$ is trifluoromethyl, or $X^1$ is trifluoromethyl, $X^2$ is CH, $X^3$ is trifluoromethyl, or $X^1$ is trifluoromethyl, $X^2$ is C—Cl, $X^3$ is trifluoromethyl, or $X^1$ is trifluoromethyl, $X^2$ is CH, $X^3$ is hydrogen, or $X^1$ is chloro, $X^2$ is N, $X^3$ is chloro, or $X^1$ is trifluoromethyl, $X^2$ is N, $X^3$ is trifluoromethyl. Preferably $X^1$ is chloro, $X^2$ is CH, $X^3$ is chloro, or $X^1$ is chloro, $X^2$ is C—Cl, $X^3$ is chloro, or $X^1$ is chloro, $X^2$ is C—F, $X^3$ is chloro, or $X^1$ is trifluoromethyl, $X^2$ is CH, $X^3$ is trifluoromethyl. Most preferably $X^1$ is chloro, $X^2$ is CH, $X^3$ is chloro.

Preferably $X^4$ is trifluoromethyl.

In one embodiment the invention provides compounds of formula IB wherein
$G^1$ is oxygen;
$R^1$ is hydrogen;
$R^2$ is thietan-3-ylmethyl-, 1-oxo-thietan-3-ylmethyl-, or 1,1-Dioxo-thietan-3-ylmethyl-;
$Y^1$ is CH, $Y^2$ is CH, $Y^3$ is CH;
$R^5$ is chloro, bromo, fluoro, methyl, trifluoromethyl;
$X^1$ is chloro, $X^2$ is CH, $X^3$ is chloro, $X^1$ is chloro, $X^2$ is C—Cl, $X^3$ is chloro, $X^1$ is chloro, $X^2$ is C—F, $X^3$ is chloro, or $X^1$ is trifluoromethyl, $X^2$ is CH, $X^3$ is trifluoromethyl; and
$X^4$ is trifluoromethyl.

In embodiment the invention provides compounds of formula IB wherein $R^2$ is thietan-3-ylmethyl- and $G^1$, $R^1$, $Y^1$, $Y^2$, $Y^3$, $X^1$, $X^2$, $X^3$ and $X^4$ are as defined for the compound of formula IB.

In embodiment the invention provides compounds of formula IB wherein $R^2$ is 1-oxo-thietan-3-ylmethyl- and $G^1$, $R^1$, $Y^1$, $Y^2$, $Y^3$, $X^1$, $X^2$, $X^3$ and $X^4$ are as defined for the compound of formula IB.

In embodiment the invention provides compounds of formula IB wherein $R^2$ is 1,1-Dioxo-thietan-3-ylmethyl- and $G^1$, $R^1$, $Y^1$, $Y^2$, $Y^3$, $X^1$, $X^2$, $X^3$ and $X^4$ are as defined for the compound of formula IB.

In one embodiment the invention provides a compound of formula IB for use in controlling and/or preventing insects of the family Curculionidae, preferably in for use in controlling and/or preventing *Anthonomus grandis*.

Additional examples of insects from the family of Curculionidae are *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasclBtus*, and *Anthonomus tenebrosus*.

In one embodiment the invention provides a compound of formula IB for use against *Anthonomus grandis* in cotton.

In one embodiment the invention provides a compound of formula IB for use in controlling and/or preventing soil pests.

In one embodiment the invention provides a compound of formula IB for use in controlling and/or preventing corn rootworm, in particular for use against corn root worm from the genus *DlBbrotica*.

In one embodiment the invention provides a compound of formula IB for use in controlling and/or preventing *Diabrotica virgifera*.

In one embodiment the invention provides a compound of formula IB for use in controlling and/or preventing *Diabrotica barberi*.

In one embodiment the invention provides a compound of formula IB for use in controlling and/or preventing *Diabrotica undecimpunctata* howardi.

In one embodiment the invention provides a compound of formula IB for use in controlling and/or preventing wireworms, in particular *Agriotes* spp.

In one embodiment the invention provides a compound of formula IB for use in controlling and/or preventing *Agriotes* spp. in cereals, potato or corn.

Additional examples of *Agriotes* spp. include *Agriotes lineatus, Agriotes obscurus, Agriotes brevis, Agriotes gurgistanus, Agriotes sputator, Agriotes ustulatus, Ctenicera destructor*, and *Limonius californicus*.

In one embodiment the invention provides a compound of formula IB for use in controlling and/or preventing grubs, in particular white grubs.

In one embodiment the invention provides a compound of formula IB for use in controlling and/or preventing *Phyllophaga* spp., particularly on corn, soybean or cotton.

In one embodiment the invention provides a compound of formula IB for use in controlling and/or preventing *Diloboderus* spp. particularly on corn, soybean or cotton.

In one embodiment the invention provides a compound of formula IB for use in controlling and/or preventing *Popillia japonica*, particularly on corn, soybean or cotton.

Additional examples of white grubs include *Phyllophaga anxia, Phyllophaga crinite, Phyllophaga subnitida, Diloboderus abderus*.

In one embodiment the invention provides a compound of formula IB for use in controlling and/or preventing termites, e.g. on sugarcane.

Examples of termites include *Reticulitermes, Coptotermes, Macrotermes, Microtermes, Globitermes*. Specific of subterranean termites include *Reticulitermes flavipes, Reticulitermes hesperus, Reticulitermes verginicus, Reticulitermes hageni, Reticulitermes speratus, Reticulitermes lucifugus, Heterotermes aureus, Coptotermes formosanus, Coptotermes acinaciformis, Coptotermes curvignathus, Nasutitermes exitiosus, Nasutitermes walkeri, Mastotermes darwiniensis, Schedorhinotermes* spp, *Macrotermes bellicosus, Macrotermes* spp., *Globitermes sulphureus, Odontotermes* spp. Specific examples of dry wood termites include *Incisitermes minor, Marginitermes hubbardi, Cryptotermes brevis, Kalotermes flavicollis*. Additional examples of termites include *procornitermes* spp. and *procornitermes araujoi*

In one embodiment the invention provides a compound of formula IB for use in controlling and/or preventing subterraneous stinkbugs, e.g. *Scaptocoris* spp.

In one embodiment the invention provides a compound of formula IB for use in controlling and/or preventing *Scaptocoris castaneus*, in particular on cereals, soybean or corn.

In one embodiment the invention provides a compound of formula IB for use in controlling and/or preventing cutworms, e.g. *agrotis* spp.

In one embodiment the invention provides a compound of formula IB for use in controlling and/or preventing *Agrotis ipsilon*, particularly on cereals, canola, soybean or corn.

In one embodiment the invention provides a compound of formula IB for use in controlling and/or preventing millipedes, e.g. *Julus* spp.

In one embodiment the invention provides a compound of formula IB for use in controlling and/or preventing *Julus* spp., particularly on cereals, canola, soybean & corn.

In one embodiment the invention provides a compound of formula IB for use in controlling and/or preventing broca gigante, e.g. *Telchin licus*, particularly on sugarcane.

In one embodiment the invention provides a compound of formula IB for use in controlling and/or preventing whitefly.

In one embodiment the invention provides a compound of formula IB for use in controlling and/or preventing *Bemisia tabaci*, particularly on vegetables, cotton, soybean, or potatoes.

In one embodiment the invention provides a compound of formula IB for use in controlling and/or preventing *Trialeurodes vaporariorum*, particularly on vegetables, cotton, soybean, or potatoes.

In one embodiment the invention provides a compound of formula IB for use in controlling and/or preventing stinkbugs, in particular *Euschistus* spp.

In one embodiment the invention provides a compound of formula IB for use in controlling and/or preventing *Euschistus* spp., particularly in soybean.

Examples of stinkbugs include *Nezara* spp. (e.g. *Nezara viridula, Nezara antennata, Nezara hilare*), *Piezodorus* spp. (e.g. *Piezodorus guildinii*), *Acrosternum* spp. *Euchistus* spp. (e.g. *Euschistus heros, Euschistus servus*), *Halyomorpha halys, Plautia crossota, Riptortus clavatus, Rhopalus msculatus, Antestiopsis orbitalus, Dichelops* spp. (e.g. *Dichelops furcatus, Dichelops melacanthus*), *Eurygaster* spp. (e.g. *Eurygaster intergriceps, Eurygaster maura*), *Oebalus* spp. (e.g. *Oebalus mexicana, Oebalus poecilus, Oebalus pugnase, Scotinophara* spp. (e.g. *Scotinophara lurida, Scotinophara coarctata*). Preferred targets include *Antestiopsis orbitalus, Dichelops furcatus, Dichelops melacanthus, Euschistus heros, Euschistus servus, Nezara viridula, Nezara hilare, Piezodorus guildinii, Halyomorpha halys*. In one embodiment the stinkbug target is *Nezara viridula, Piezodorus* spp., *Acrosternum* spp, *Euschistus heros*.

In one embodiment the invention provides a compound of formula IB for use against rice pests.

In one embodiment the invention provides a compound of formula IB for use against stemborer, particularly in rice.

Examples of stemborers include *Chilo* sp, *Chilo suppressalis*, *Chilo polychrysus*, *Chilo auricilius*, *Scirpophaga* spp., *Scirpophaga incertulas*, *Scirpophaga innotata*, *Scirpophaga nivella Sesamia* sp, *Sesamia inferens*.

In one embodiment the invention provides a compound of formula IB for use against leaffolder, particularly in rice.

Examples of leaffolders include *Cnaphalocrocis* spp., *Cnaphalocrocis medinalis*, *Marasmia* spp., *Marasmia patnalis*, *Marasmia exigua*.

In one embodiment the invention provides a compound of formula IB for use against hoppers, particularly in rice.

Examples of Hoppers include *Nephotettix* spp., *Nephotettix virescens*, *Nephotettix nigropictus*, *Nephotettix malayanus*, *Nephotettix cincticeps*, *Nilaparvata lugens*, *Sogatella furcifera*.

In one embodiment the invention provides a compound of formula IB for use against gallmidge, particularly in rice.

Examples of Gall midge include *Orseolia* sp, *Orseolia oryzae*.

In one embodiment the invention provides a compound of formula IB for use against whorl maggot, particularly in rice.

Examples of whorl maggots include *Hydrellia* sp, *Hydrellia philippina*.

In one embodiment the invention provides a compound of formula IB for use against Rice bugs, particularly in rice.

Examples of rice bugs include *Leptocorisa* sp, *Leptocorisa oratorius*, *Leptocorisa chinensis*, *Leptocorisa acuta*.

In one embodiment the invention provides a compound of formula IB for use against Black bugs, particularly in rice.

Examples of Black bugs include *Scotinophara* sp, *Scotinophara coarctata*, *Scotinophara lurida*, *Scotinophara latiuscula*.

In one embodiment the invention provides a compound of formula IB for use against *plutella* spp.

In one embodiment the invention provides a compound of formula IB for use against *Plutella xylostella*, particularly in *brassica* crops.

The compounds in the Tables below illustrate the compounds of the invention.

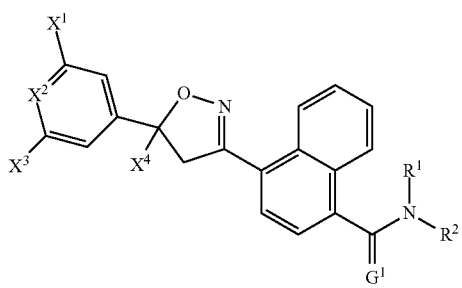

(I-B)

TABLE P

| | $X^4$ | $R^2$ |
|---|---|---|
| P.001 | chlorodifluoromethyl | (1,1-dioxothietan-2-yl)methyl- |
| P.002 | chlorodifluoromethyl | (1-oxothietan-2-yl)methyl- |
| P.003 | chlorodifluoromethyl | 1,1-Dioxo-thietan-3-yl- |
| P.004 | chlorodifluoromethyl | 1,1-Dioxo-thietan-3-ylmethyl- |
| P.005 | chlorodifluoromethyl | trans-1-oxo-thietan-3-yl- |

TABLE P-continued

| | $X^4$ | $R^2$ |
|---|---|---|
| P.006 | chlorodifluoromethyl | trans-1-oxo-thietan-3-ylmethyl- |
| P.007 | chlorodifluoromethyl | 2-(1,1-dioxothietan-3-yl)ethanyl |
| P.008 | chlorodifluoromethyl | 2-(1-oxothietan-3-yl)ethanyl |
| P.009 | chlorodifluoromethyl | 2-(thietan-3-yl)ethanyl |
| P.010 | chlorodifluoromethyl | 2,2-dimethyl-1,1-Dioxo-thietan-3-yl- |
| P.011 | chlorodifluoromethyl | 2,2-dimethyl-1-oxo-thietan-3-yl- |
| P.012 | chlorodifluoromethyl | 2,2-dimethylthietan-3-yl- |
| P.013 | chlorodifluoromethyl | 3-Methyl-1,1-Dioxo-thietan-3-yl- |
| P.014 | chlorodifluoromethyl | 3-Methyl-1-oxo-thietan-3-yl- |
| P.015 | chlorodifluoromethyl | 3-Methyl-thietan-3-yl- |
| P.016 | chlorodifluoromethyl | thietan-2-ylmethyl- |
| P.017 | chlorodifluoromethyl | thietan-3-yl- |
| P.018 | chlorodifluoromethyl | thietan-3-ylmethyl- |
| P.019 | difluoromethyl | (1,1-dioxothietan-2-yl)methyl- |
| P.020 | difluoromethyl | (1-oxothietan-2-yl)methyl- |
| P.021 | difluoromethyl | 1,1-Dioxo-thietan-3-yl- |
| P.022 | difluoromethyl | 1,1-Dioxo-thietan-3-ylmethyl- |
| P.023 | difluoromethyl | trans-1-oxo-thietan-3-yl- |
| P.024 | difluoromethyl | trans-1-oxo-thietan-3-ylmethyl- |
| P.025 | difluoromethyl | 2-(1,1-dioxothietan-3-yl)ethanyl |
| P.026 | difluoromethyl | 2-(1-oxothietan-3-yl)ethanyl |
| P.027 | difluoromethyl | 2-(thietan-3-yl)ethanyl |
| P.028 | difluoromethyl | 2,2-dimethyl-1,1-Dioxo-thietan-3-yl- |
| P.029 | difluoromethyl | 2,2-dimethyl-1-oxo-thietan-3-yl- |
| P.030 | difluoromethyl | 2,2-dimethylthietan-3-yl- |
| P.031 | difluoromethyl | 3-Methyl-1,1-Dioxo-thietan-3-yl- |
| P.032 | difluoromethyl | 3-Methyl-1-oxo-thietan-3-yl- |
| P.033 | difluoromethyl | 3-Methyl-thietan-3-yl- |
| P.034 | difluoromethyl | thietan-2-ylmethyl- |
| P.035 | difluoromethyl | thietan-3-yl- |
| P.036 | difluoromethyl | thietan-3-ylmethyl- |
| P.037 | trifluoromethyl | (1,1-dioxothietan-2-yl)methyl- |
| P.038 | trifluoromethyl | (1-oxothietan-2-yl)methyl- |
| P.039 | trifluoromethyl | 1,1-Dioxo-thietan-3-yl- |
| P.040 | trifluoromethyl | 1,1-Dioxo-thietan-3-ylmethyl- |
| P.041 | trifluoromethyl | trans-1-oxo-thietan-3-yl- |
| P.042 | trifluoromethyl | trans-1-oxo-thietan-3-ylmethyl- |
| P.043 | trifluoromethyl | 2-(1,1-dioxothietan-3-yl)ethanyl |
| P.044 | trifluoromethyl | 2-(1-oxothietan-3-yl)ethanyl |
| P.045 | trifluoromethyl | 2-(thietan-3-yl)ethanyl |
| P.046 | trifluoromethyl | 2,2-dimethyl-1,1-Dioxo-thietan-3-yl- |
| P.047 | trifluoromethyl | 2,2-dimethyl-1-oxo-thietan-3-yl- |
| P.048 | trifluoromethyl | 2,2-dimethylthietan-3-yl- |
| P.049 | trifluoromethyl | 3-Methyl-1,1-Dioxo-thietan-3-yl- |
| P.050 | trifluoromethyl | 3-Methyl-1-oxo-thietan-3-yl- |
| P.051 | trifluoromethyl | 3-Methyl-thietan-3-yl- |
| P.052 | trifluoromethyl | thietan-2-ylmethyl- |
| P.053 | trifluoromethyl | thietan-3-yl- |
| P.054 | trifluoromethyl | thietan-3-ylmethyl- |
| P.055 | chlorodifluoromethyl | cis-1-oxo-thietan-3-yl- |
| P.056 | chlorodifluoromethyl | cis-1-oxo-thietan-3-ylmethyl- |
| P.057 | difluoromethyl | cis-1-oxo-thietan-3-yl- |
| P.058 | difluoromethyl | cis-1-oxo-thietan-3-ylmethyl- |
| P.059 | trifluoromethyl | cis-1-oxo-thietan-3-yl- |
| P.060 | trifluoromethyl | cis-1-oxo-thietan-3-ylmethyl- |

Table 1

Table 1 provides 60 compounds of formula (I-B) wherein $G^1$ is oxygen, $R^1$ is hydrogen, $X^1$ is chloro, $X^2$ is CH, $X^3$ is chloro, $X^4$ and $R^2$ have the values listed in the table P.

Table 2

Table 2 provides 60 compounds of formula (I-B) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 3

Table 3 provides 60 compounds of formula (I-B) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 4

Table 4 provides 60 compounds of formula (I-B) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 5

Table 5 provides 60 compounds of formula (I-B) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 6

Table 6 provides 60 compounds of formula (I-B) wherein $G^1$ is oxygen, $R^1$ is hydrogen, $X^1$ is chloro, $X^2$ is C—F, $X^3$ is chloro, $X^4$ and $R^2$ have the values listed in the table P.

Table 7

Table 7 provides 60 compounds of formula (I-B) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 8

Table 8 provides 60 compounds of formula (I-B) wherein $G^1$ is oxygen, $R^1$ is hydrogen, $X^1$ is chloro, $X^2$ is C—I, $X^3$ is chloro, $X^4$ and $R^2$ have the values listed in the table P.

Table 9

Table 9 provides 60 compounds of formula (I-B) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 10

Table 10 provides 60 compounds of formula (I-B) wherein $G^1$ is oxygen, $R^1$ is hydrogen, $X^1$ is chloro, $X^2$ is CH, $X^3$ is bromo, $X^4$ and $R^2$ have the values listed in the table P.

Table 11

Table 11 provides 60 compounds of formula (I-B) wherein $G^1$ is oxygen, $R^1$ is hydrogen, $X^1$ is chloro, $X^2$ is CH, $X^3$ is fluoro, $X^4$ and $R^2$ have the values listed in the table P.

Table 12

Table 12 provides 60 compounds of formula (I-B) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 13

Table 13 provides 60 compounds of formula (I-B) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 14

Table 14 provides 60 compounds of formula (I-B) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 15

Table 15 provides 60 compounds of formula (I-B) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 16

Table 16 provides 60 compounds of formula (I-B) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 17

Table 17 provides 60 compounds of formula (I-B) wherein $G^1$ is oxygen, $R^1$ is hydrogen, $X^1$ is chloro, $X^2$ is N, $X^3$ is chloro, $X^4$ and $R^2$ have the values listed in the table P.

Table 18

Table 18 provides 60 compounds of formula (I-B) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

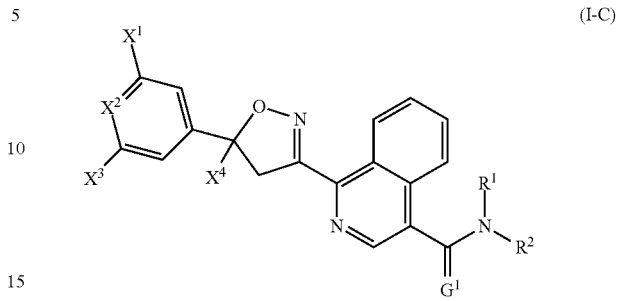

(I-C)

Table 19

Table 19 provides 60 compounds of formula (I—C) wherein $G^1$ is oxygen, $R^1$ is hydrogen, $X^1$ is chloro, $X^2$ is CH, $X^3$ is chloro, $X^4$ and $R^2$ have the values listed in the table P.

Table 20

Table 20 provides 60 compounds of formula (I—C) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 21

Table 21 provides 60 compounds of formula (I—C) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 22

Table 22 provides 60 compounds of formula (I—C) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 23

Table 23 provides 60 compounds of formula (I—C) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 24

Table 24 provides 60 compounds of formula (I—C) wherein $G^1$ is oxygen, $R^1$ is hydrogen, $X^1$ is chloro, $X^2$ is C—F, $X^3$ is chloro, $X^4$ and $R^2$ have the values listed in the table P.

Table 25

Table 25 provides 60 compounds of formula (I—C) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 26

Table 26 provides 60 compounds of formula (I—C) wherein $G^1$ is oxygen, $R^1$ is hydrogen, $X^1$ is chloro, $X^2$ is C—I, $X^3$ is chloro, $X^4$ and $R^2$ have the values listed in the table P.

Table 27

Table 27 provides 60 compounds of formula (I—C) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 28

Table 28 provides 60 compounds of formula (I—C) wherein $G^1$ is oxygen, $R^1$ is hydrogen, $X^1$ is chloro, $X^2$ is CH, $X^3$ is bromo, $X^4$ and $R^2$ have the values listed in the table P.

Table 29

Table 29 provides 60 compounds of formula (I—C) wherein $G^1$ is oxygen, $R^1$ is hydrogen, $X^1$ is chloro, $X^2$ is CH, $X^3$ is fluoro, $X^4$ and $R^2$ have the values listed in the table P.

Table 30

Table 30 provides 60 compounds of formula (I—C) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 31

Table 31 provides 60 compounds of formula (I—C) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 32

Table 32 provides 60 compounds of formula (I—C) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 33

Table 33 provides 60 compounds of formula (I—C) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 34

Table 34 provides 60 compounds of formula (I—C) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 35

Table 35 provides 60 compounds of formula (I—C) wherein $G^1$ is oxygen, $R^1$ is hydrogen, $X^1$ is chloro, $X^2$ is N, $X^3$ is chloro, $X^4$ and $R^2$ have the values listed in the table P.

Table 36

Table 36 provides 60 compounds of formula (I—C) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

(X1-B)

Table 37

Table 37 provides 60 compounds of formula (X1-B) wherein $G^1$ is oxygen, $R^1$ is hydrogen, $X^1$ is chloro, $X^2$ is CH, $X^3$ is chloro, $X^4$ and $R^2$ have the values listed in the table P.

Table 38

Table 38 provides 60 compounds of formula (X1-B) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 39

Table 39 provides 60 compounds of formula (X1-B) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 40

Table 40 provides 60 compounds of formula (X1-B) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 41

Table 41 provides 60 compounds of formula (X1-B) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 42

Table 42 provides 60 compounds of formula (X1-B) wherein $G^1$ is oxygen, $R^1$ is hydrogen, $X^1$ is chloro, $X^2$ is C—F, $X^3$ is chloro, $X^4$ and $R^2$ have the values listed in the table P.

Table 43

Table 43 provides 60 compounds of formula (X1-B) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 44

Table 44 provides 60 compounds of formula (X1-B) wherein $G^1$ is oxygen, $R^1$ is hydrogen, $X^1$ is chloro, $X^2$ is C—I, $X^3$ is chloro, $X^4$ and $R^2$ have the values listed in the table P.

Table 45

Table 45 provides 60 compounds of formula (X1-B) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 46

Table 46 provides 60 compounds of formula (X1-B) wherein $G^1$ is oxygen, $R^1$ is hydrogen, $X^1$ is chloro, $X^2$ is CH, $X^3$ is bromo, $X^4$ and $R^2$ have the values listed in the table P.

Table 47

Table 47 provides 60 compounds of formula (X1-B) wherein $G^1$ is oxygen, $R^1$ is hydrogen, $X^1$ is chloro, $X^2$ is CH, $X^3$ is fluoro, $X^4$ and $R^2$ have the values listed in the table P.

Table 48

Table 48 provides 60 compounds of formula (X1-B) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 49

Table 49 provides 60 compounds of formula (X1-B) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 50

Table 50 provides 60 compounds of formula (X1-B) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 51

Table 51 provides 60 compounds of formula (X1-B) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 52

Table 52 provides 60 compounds of formula (X1-B) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 53

Table 53 provides 60 compounds of formula (X1-B) wherein $G^1$ is oxygen, $R^1$ is hydrogen, $X^1$ is chloro, $X^2$ is N, $X^3$ is chloro, $X^4$ and $R^2$ have the values listed in the table P.

Table 54
Table 54 provides 60 compounds of formula (X1-B) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

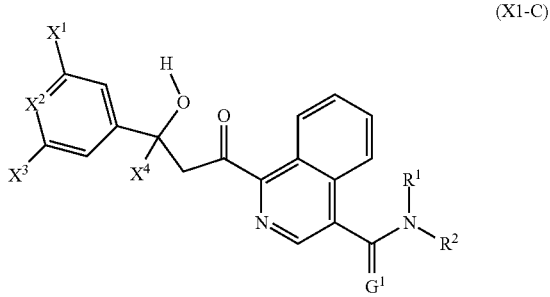

Table 55
Table 55 provides 60 compounds of formula (X1-C) wherein $G^1$ is oxygen, $R^1$ is hydrogen, $X^1$ is chloro, $X^2$ is CH, $X^3$ is chloro, $X^4$ and $R^2$ have the values listed in the table P.

Table 56
Table 56 provides 60 compounds of formula (X1-C) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 57
Table 57 provides 60 compounds of formula (X1-C) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 58
Table 58 provides 60 compounds of formula (X1-C) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 59
Table 59 provides 60 compounds of formula (X1-C) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 60
Table 60 provides 60 compounds of formula (X1-C) wherein $G^1$ is oxygen, $R^1$ is hydrogen, $X^1$ is chloro, $X^2$ is C—F, $X^3$ is chloro, $X^4$ and $R^2$ have the values listed in the table P.

Table 61
Table 61 provides 60 compounds of formula (X1-C) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 62
Table 62 provides 60 compounds of formula (X1-C) wherein $G^1$ is oxygen, $R^1$ is hydrogen, $X^1$ is chloro, $X^2$ is C—I, $X^3$ is chloro, $X^4$ and $R^2$ have the values listed in the table P.

Table 63
Table 63 provides 60 compounds of formula (X1-C) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 64
Table 64 provides 60 compounds of formula (X1-C) wherein $G^1$ is oxygen, $R^1$ is hydrogen, $X^1$ is chloro, $X^2$ is CH, $X^3$ is bromo, $X^4$ and $R^2$ have the values listed in the table P.

Table 65
Table 65 provides 60 compounds of formula (X1-C) wherein $G^1$ is oxygen, $R^1$ is hydrogen, $X^1$ is chloro, $X^2$ is CH, $X^3$ is fluoro, $X^4$ and $R^2$ have the values listed in the table P.

Table 66
Table 66 provides 60 compounds of formula (X1-C) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 67
Table 67 provides 60 compounds of formula (X1-C) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 68
Table 68 provides 60 compounds of formula (X1-C) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 69
Table 69 provides 60 compounds of formula (X1-C) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 70
Table 70 provides 60 compounds of formula (X1-C) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 71
Table 71 provides 60 compounds of formula (X1-C) wherein $G^1$ is oxygen, $R^1$ is hydrogen, $X^1$ is chloro, $X^2$ is N, $X^3$ is chloro, $X^4$ and $R^2$ have the values listed in the table P.

Table 72
Table 72 provides 60 compounds of formula (X1-C) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

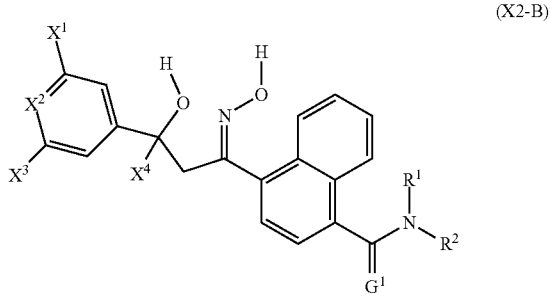

Table 73
Table 73 provides 60 compounds of formula (X2-B) wherein $G^1$ is oxygen, $R^1$ is hydrogen, $X^1$ is chloro, $X^2$ is CH, $X^3$ is chloro, $X^4$ and $R^2$ have the values listed in the table P.

Table 74
Table 74 provides 60 compounds of formula (X2-B) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 75

Table 75 provides 60 compounds of formula (X2-B) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 76

Table 76 provides 60 compounds of formula (X2-B) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 77

Table 77 provides 60 compounds of formula (X2-B) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 78

Table 78 provides 60 compounds of formula (X2-B) wherein $G^1$ is oxygen, $R^1$ is hydrogen, $X^1$ is chloro, $X^2$ is C—F, $X^3$ is chloro, $X^4$ and $R^2$ have the values listed in the table P.

Table 79

Table 79 provides 60 compounds of formula (X2-B) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 80

Table 80 provides 60 compounds of formula (X2-B) wherein $G^1$ is oxygen, $R^1$ is hydrogen, $X^1$ is chloro, $X^2$ is C—I, $X^3$ is chloro, $X^4$ and $R^2$ have the values listed in the table P.

Table 81

Table 81 provides 60 compounds of formula (X2-B) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 82

Table 82 provides 60 compounds of formula (X2-B) wherein $G^1$ is oxygen, $R^1$ is hydrogen, $X^1$ is chloro, $X^2$ is CH, $X^3$ is bromo, $X^4$ and $R^2$ have the values listed in the table P.

Table 83

Table 83 provides 60 compounds of formula (X2-B) wherein $G^1$ is oxygen, $R^1$ is hydrogen, $X^1$ is chloro, $X^2$ is CH, $X^3$ is fluoro, $X^4$ and $R^2$ have the values listed in the table P.

Table 84

Table 84 provides 60 compounds of formula (X2-B) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 85

Table 85 provides 60 compounds of formula (X2-B) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 86

Table 86 provides 60 compounds of formula (X2-B) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 87

Table 87 provides 60 compounds of formula (X2-B) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 88

Table 88 provides 60 compounds of formula (X2-B) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 89

Table 89 provides 60 compounds of formula (X2-B) wherein $G^1$ is oxygen, $R^1$ is hydrogen, $X^1$ is chloro, $X^2$ is N, $X^3$ is chloro, $X^4$ and $R^2$ have the values listed in the table P.

Table 90

Table 90 provides 60 compounds of formula (X2-B) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

(X2-C)

[Chemical structure]

Table 91

Table 91 provides 60 compounds of formula (X2-C) wherein $G^1$ is oxygen, $R^1$ is hydrogen, $X^1$ is chloro, $X^2$ is CH, $X^3$ is chloro, $X^4$ and $R^2$ have the values listed in the table P.

Table 92:

Table 92 provides 60 compounds of formula (X2-C) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 93:

Table 93 provides 60 compounds of formula (X2-C) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 94:

Table 94 provides 60 compounds of formula (X2-C) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 95:

Table 95 provides 60 compounds of formula (X2-C) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 96:

Table 96 provides 60 compounds of formula (X2-C) wherein $G^1$ is oxygen, $R^1$ is hydrogen, $X^1$ is chloro, $X^2$ is C—F, $X^3$ is chloro, $X^4$ and $R^2$ have the values listed in the table P.

Table 97:

Table 97 provides 60 compounds of formula (X2-C) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 98:

Table 98 provides 60 compounds of formula (X2-C) wherein $G^1$ is oxygen, $R^1$ is hydrogen, $X^1$ is chloro, $X^2$ is C—I, $X^3$ is chloro, $X^4$ and $R^2$ have the values listed in the table P.

Table 99:

Table 99 provides 60 compounds of formula (X2-C) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 100:

Table 100 provides 60 compounds of formula (X2-C) wherein $G^1$ is oxygen, $R^1$ is hydrogen, $X^1$ is chloro, $X^2$ is CH, $X^3$ is bromo, $X^4$ and $R^2$ have the values listed in the table P.

Table 101:

Table 101 provides 60 compounds of formula (X2-C) wherein $G^1$ is oxygen, $R^1$ is hydrogen, $X^1$ is chloro, $X^2$ is CH, $X^3$ is fluoro, $X^4$ and $R^2$ have the values listed in the table P.

Table 102:

Table 102 provides 60 compounds of formula (X2-C) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 103:

Table 103 provides 60 compounds of formula (X2-C) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 104:

Table 104 provides 60 compounds of formula (X2-C) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 105:

Table 105 provides 60 compounds of formula (X2-C) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 106:

Table 106 provides 60 compounds of formula (X2-C) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 107:

Table 107 provides 60 compounds of formula (X2-C) wherein $G^1$ is oxygen, $R^1$ is hydrogen, $X^1$ is chloro, $X^2$ is N, $X^3$ is chloro, $X^4$ and $R^2$ have the values listed in the table P.

Table 108:

Table 108 provides 60 compounds of formula (X2-C) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

(X3-B)

Table 109

Table 109 provides 60 compounds of formula (X3-B) wherein $G^1$ is oxygen, $R^1$ is hydrogen, $X^1$ is chloro, $X^2$ is CH, $X^3$ is chloro, $X^4$ and $R^2$ have the values listed in the table P.

Table 110

Table 110 provides 60 compounds of formula (X3-B) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 111

Table 111 provides 60 compounds of formula (X3-B) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 112

Table 112 provides 60 compounds of formula (X3-B) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 113

Table 113 provides 60 compounds of formula (X3-B) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 114

Table 114 provides 60 compounds of formula (X3-B) wherein $G^1$ is oxygen, $R^1$ is hydrogen, $X^1$ is chloro, $X^2$ is C—F, $X^3$ is chloro, $X^4$ and $R^2$ have the values listed in the table P.

Table 115

Table 115 provides 60 compounds of formula (X3-B) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 116

Table 116 provides 60 compounds of formula (X3-B) wherein $G^1$ is oxygen, $R^1$ is hydrogen, $X^1$ is chloro, $X^2$ is C—I, $X^3$ is chloro, $X^4$ and $R^2$ have the values listed in the table P.

Table 117

Table 117 provides 60 compounds of formula (X3-B) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 118

Table 118 provides 60 compounds of formula (X3-B) wherein $G^1$ is oxygen, $R^1$ is hydrogen, $X^1$ is chloro, $X^2$ is CH, $X^3$ is bromo, $X^4$ and $R^2$ have the values listed in the table P.

Table 119

Table 119 provides 60 compounds of formula (X3-B) wherein $G^1$ is oxygen, $R^1$ is hydrogen, $X^1$ is chloro, $X^2$ is CH, $X^3$ is fluoro, $X^4$ and $R^2$ have the values listed in the table P.

Table 120

Table 120 provides 60 compounds of formula (X3-B) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 121

Table 121 provides 60 compounds of formula (X3-B) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 122

Table 122 provides 60 compounds of formula (X3-B) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 123

Table 123 provides 60 compounds of formula (X3-B) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 124

Table 124 provides 60 compounds of formula (X3-B) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 125

Table 125 provides 60 compounds of formula (X3-B) wherein $G^1$ is oxygen, $R^1$ is hydrogen, $X^1$ is chloro, $X^2$ is N, $X^3$ is chloro, $X^4$ and $R^2$ have the values listed in the table P.

Table 126

Table 126 provides 60 compounds of formula (X3-B) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

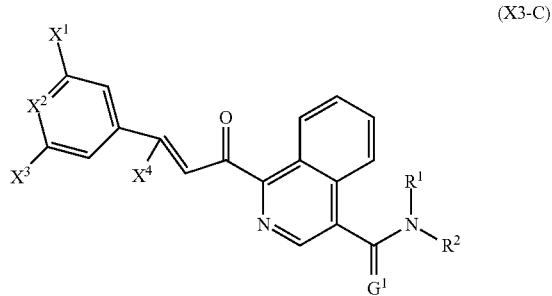

(X3-C)

Table 127

Table 127 provides 60 compounds of formula (X3-C) wherein $G^1$ is oxygen, $R^1$ is hydrogen, $X^1$ is chloro, $X^2$ is CH, $X^3$ is chloro, $X^4$ and $R^2$ have the values listed in the table P.

Table 128

Table 128 provides 60 compounds of formula (X3-C) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 129

Table 129 provides 60 compounds of formula (X3-C) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 130

Table 130 provides 60 compounds of formula (X3-C) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 131

Table 131 provides 60 compounds of formula (X3-C) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 132

Table 132 provides 60 compounds of formula (X3-C) wherein $G^1$ is oxygen, $R^1$ is hydrogen, $X^1$ is chloro, $X^2$ is C—F, $X^3$ is chloro, $X^4$ and $R^2$ have the values listed in the table P.

Table 133

Table 133 provides 60 compounds of formula (X3-C) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 134

Table 134 provides 60 compounds of formula (X3-C) wherein $G^1$ is oxygen, $R^1$ is hydrogen, $X^1$ is chloro, $X^2$ is C—I, $X^3$ is chloro, $X^4$ and $R^2$ have the values listed in the table P.

Table 135

Table 135 provides 60 compounds of formula (X3-C) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 136

Table 136 provides 60 compounds of formula (X3-C) wherein $G^1$ is oxygen, $R^1$ is hydrogen, $X^1$ is chloro, $X^2$ is CH, $X^3$ is bromo, $X^4$ and $R^2$ have the values listed in the table P.

Table 137

Table 137 provides 60 compounds of formula (X3-C) wherein $G^1$ is oxygen, $R^1$ is hydrogen, $X^1$ is chloro, $X^2$ is CH, $X^3$ is fluoro, $X^4$ and $R^2$ have the values listed in the table P.

Table 138

Table 138 provides 60 compounds of formula (X3-C) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 139

Table 139 provides 60 compounds of formula (X3-C) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 140

Table 140 provides 60 compounds of formula (X3-C) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 141

Table 141 provides 60 compounds of formula (X3-C) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 142

Table 142 provides 60 compounds of formula (X3-C) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 143

Table 143 provides 60 compounds of formula (X3-C) wherein $G^1$ is oxygen, $R^1$ is hydrogen, $X^1$ is chloro, $X^2$ is N, $X^3$ is chloro, $X^4$ and $R^2$ have the values listed in the table P.

Table 144

Table 144 provides 60 compounds of formula (X3-C) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

(X4-B)

Table 145
Table 145 provides 60 compounds of formula (X4-B) wherein $G^1$ is oxygen, $R^1$ is hydrogen, $X^1$ is chloro, $X^2$ is CH, $X^3$ is chloro, $X^4$ and $R^2$ have the values listed in the table P.

Table 146
Table 146 provides 60 compounds of formula (X4-B) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 147
Table 147 provides 60 compounds of formula (X4-B) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 148
Table 148 provides 60 compounds of formula (X4-B) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 149
Table 149 provides 60 compounds of formula (X4-B) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 150
Table 150 provides 60 compounds of formula (X4-B) wherein $G^1$ is oxygen, $R^1$ is hydrogen, $X^1$ is chloro, $X^2$ is C—F, $X^3$ is chloro, $X^4$ and $R^2$ have the values listed in the table P.

Table 151
Table 151 provides 60 compounds of formula (X4-B) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 152
Table 152 provides 60 compounds of formula (X4-B) wherein $G^1$ is oxygen, $R^1$ is hydrogen, $X^1$ is chloro, $X^2$ is C—I, $X^3$ is chloro, $X^4$ and $R^2$ have the values listed in the table P.

Table 153
Table 153 provides 60 compounds of formula (X4-B) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 154
Table 154 provides 60 compounds of formula (X4-B) wherein $G^1$ is oxygen, $R^1$ is hydrogen, $X^1$ is chloro, $X^2$ is CH, $X^3$ is bromo, $X^4$ and $R^2$ have the values listed in the table P.

Table 155
Table 155 provides 60 compounds of formula (X4-B) wherein $G^1$ is oxygen, $R^1$ is hydrogen, $X^1$ is chloro, $X^2$ is CH, $X^3$ is fluoro, $X^4$ and $R^2$ have the values listed in the table P.

Table 156
Table 156 provides 60 compounds of formula (X4-B) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 157
Table 157 provides 60 compounds of formula (X4-B) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 158
Table 158 provides 60 compounds of formula (X4-B) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 159
Table 159 provides 60 compounds of formula (X4-B) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 160
Table 160 provides 60 compounds of formula (X4-B) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 161
Table 161 provides 60 compounds of formula (X4-B) wherein $G^1$ is oxygen, $R^1$ is hydrogen, $X^1$ is chloro, $X^2$ is N, $X^3$ is chloro, $X^4$ and $R^2$ have the values listed in the table P.

Table 162
Table 162 provides 60 compounds of formula (X4-B) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

(X4-C)

Table 163
Table 163 provides 60 compounds of formula (X4-C) wherein $G^1$ is oxygen, $R^1$ is hydrogen, $X^1$ is chloro, $X^2$ is CH, $X^3$ is chloro, $X^4$ and $R^2$ have the values listed in the table P.

Table 164
Table 164 provides 60 compounds of formula (X4-C) wherein $G^1$ is oxygen, $R^1$ is hydrogen, $X^1$ is chloro, $X^2$ is C—F, $X^3$ is hydrogen, $X^4$ and $R^2$ have the values listed in the table P.

Table 165
Table 165 provides 60 compounds of formula (X4-C) wherein $G^1$ is oxygen, $R^1$ is hydrogen, $X^1$ is fluoro, $X^2$ is C—Cl, $X^3$ is hydrogen, $X^4$ and $R^2$ have the values listed in the table P.

Table 166
Table 166 provides 60 compounds of formula (X4-C) wherein $G^1$ is oxygen, $R^1$ is hydrogen, $X^1$ is chloro, $X^2$ is C—Cl, $X^3$ is hydrogen, $X^4$ and $R^2$ have the values listed in the table P.

Table 167
Table 167 provides 60 compounds of formula (X4-C) wherein $G^1$ is oxygen, $R^1$ is hydrogen, $X^1$ is chloro, $X^2$ is C—Br, $X^3$ is chloro, $X^4$ and $R^2$ have the values listed in the table P.

Table 168
Table 168 provides 60 compounds of formula (X4-C) wherein $G^1$ is oxygen, $R^1$ is hydrogen, $X^1$ is chloro, $X^2$ is C—F, $X^3$ is chloro, $X^4$ and $R^2$ have the values listed in the table P.

Table 169
Table 169 provides 60 compounds of formula (X4-C) wherein $G^1$ is oxygen, $R^1$ is hydrogen, $X^1$ is chloro, $X^2$ is C—Cl, $X^3$ is chloro, $X^4$ and $R^2$ have the values listed in the table P.

Table 170
Table 170 provides 60 compounds of formula (X4-C) wherein $G^1$ is oxygen, $R^1$ is hydrogen, $X^1$ is chloro, $X^2$ is C—I, $X^3$ is chloro, $X^4$ and $R^2$ have the values listed in the table P.

Table 171
Table 171 provides 60 compounds of formula (X4-C) wherein $G^1$ is oxygen, $R^1$ is hydrogen, $X^1$ is fluoro, $X^2$ is C—F, $X^3$ is fluoro, $X^4$ and $R^2$ have the values listed in the table P.

Table 172
Table 172 provides 60 compounds of formula (X4-C) wherein $G^1$ is oxygen, $R^1$ is hydrogen, $X^1$ is chloro, $X^2$ is CH, $X^3$ is bromo, $X^4$ and $R^2$ have the values listed in the table P.

Table 173
Table 173 provides 60 compounds of formula (X4-C) wherein $G^1$ is oxygen, $R^1$ is hydrogen, $X^1$ is chloro, $X^2$ is CH, $X^3$ is fluoro, $X^4$ and $R^2$ have the values listed in the table P.

Table 174
Table 174 provides 60 compounds of formula (X4-C) wherein $G^1$ is oxygen, $R^1$ is hydrogen, $X^1$ is chloro, $X^2$ is CH, $X^3$ is trifluoromethyl, $X^4$ and $R^2$ have the values listed in the table P.

Table 175
Table 175 provides 60 compounds of formula (X4-C) wherein $G^1$ is oxygen, $R^1$ is hydrogen, $X^1$ is chloro, $X^2$ is C—Cl, $X^3$ is trifluoromethyl, $X^4$ and $R^2$ have the values listed in the table P.

Table 176
Table 176 provides 60 compounds of formula (X4-C) wherein $G^1$ is oxygen, $R^1$ is hydrogen, $X^1$ is trifluoromethyl, $X^2$ is CH, $X^3$ is trifluoromethyl, $X^4$ and $R^2$ have the values listed in the table P.

Table 177
Table 177 provides 60 compounds of formula (X4-C) wherein $G^1$ is oxygen, $R^1$ is hydrogen, $X^1$ is trifluoromethyl, $X^2$ is C—Cl, $X^3$ is trifluoromethyl, $X^4$ and $R^2$ have the values listed in the table P.

Table 178
Table 178 provides 60 compounds of formula (X4-C) wherein $G^1$ is oxygen, $R^1$ is hydrogen, $X^1$ is trifluoromethyl, $X^2$ is CH, $X^3$ is hydrogen, $X^4$ and $R^2$ have the values listed in the table P.

Table 179
Table 179 provides 60 compounds of formula (X4-C) wherein $G^1$ is oxygen, $R^1$ is hydrogen, $X^1$ is chloro, $X^2$ is N, $X^3$ is chloro, $X^4$ and $R^2$ have the values listed in the table P.

Table 180
Table 180 provides 60 compounds of formula (X4-C) wherein $G^1$ is oxygen, $R^1$ is hydrogen, $X^1$ is trifluoromethyl, $X^2$ is N, $X^3$ is trifluoromethyl, $X^4$ and $R^2$ have the values listed in the table P.

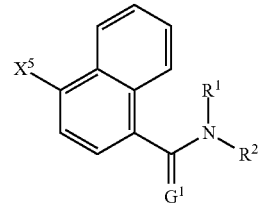

(X5-B)

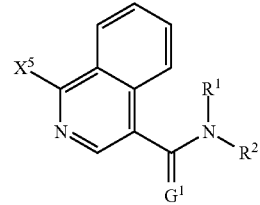

(X5-C)

Table 181
Table 181 provides 300 compounds of formula (X5-B) wherein $G^1$ is oxygen, $R^1$ is hydrogen, $X^5$ and $R^2$ have the values listed in the table I.

Table 182
Table 182 provides 300 compounds of formula (X5-C) wherein $G^1$ is oxygen, $R^1$ is hydrogen, $X^5$ and $R^2$ have the values listed in the table I.

TABLE I

| | X5 | R2 |
|---|---|---|
| I.001 | chloro | (1,1-dioxothietan-2-yl)methyl- |
| I.002 | chloro | (1-oxothietan-2-yl)methyl- |
| I.003 | chloro | 1,1-Dioxo-thietan-3-yl- |
| I.004 | chloro | 1,1-Dioxo-thietan-3-ylmethyl- |
| I.005 | chloro | trans-1-oxo-thietan-3-yl- |
| I.006 | bromo | trans-1-oxo-thietan-3-yl- |
| I.007 | chloro | 2-(1,1-dioxothietan-3-yl)ethanyl |
| I.008 | chloro | 2-(1-oxothietan-3-yl)ethanyl |
| I.009 | chloro | 2-(thietan-3-yl)ethanyl |
| I.010 | chloro | 2,2-dimethyl-1,1-Dioxo-thietan-3-yl- |
| I.011 | chloro | 2,2-dimethyl-1-oxo-thietan-3-yl- |
| I.012 | chloro | 2,2-dimethylthietan-3-yl- |
| I.013 | chloro | 3-Methyl-1,1-Dioxo-thietan-3-yl- |
| I.014 | chloro | 3-Methyl-1-oxo-thietan-3-yl- |
| I.015 | chloro | 3-Methyl-thietan-3-yl- |
| I.016 | chloro | thietan-2-ylmethyl- |
| I.017 | chloro | thietan-3-yl- |
| I.018 | chloro | thietan-3-ylmethyl- |
| I.019 | bromo | (1,1-dioxothietan-2-yl)methyl- |
| I.020 | bromo | (1-oxothietan-2-yl)methyl- |
| I.021 | bromo | 1,1-Dioxo-thietan-3-yl- |
| I.022 | bromo | 1,1-Dioxo-thietan-3-ylmethyl- |
| I.023 | iodo | trans-1-oxo-thietan-3-yl- |
| I.024 | amino | trans-1-oxo-thietan-3-yl- |
| I.025 | bromo | 2-(1,1-dioxothietan-3-yl)ethanyl |
| I.026 | bromo | 2-(1-oxothietan-3-yl)ethanyl |
| I.027 | bromo | 2-(thietan-3-yl)ethanyl |
| I.028 | bromo | 2,2-dimethyl-1,1-Dioxo-thietan-3-yl- |
| I.029 | bromo | 2,2-dimethyl-1-oxo-thietan-3-yl- |
| I.030 | bromo | 2,2-dimethylthietan-3-yl- |
| I.031 | bromo | 3-Methyl-1,1-Dioxo-thietan-3-yl- |
| I.032 | bromo | 3-Methyl-1-oxo-thietan-3-yl- |
| I.033 | bromo | 3-Methyl-thietan-3-yl- |
| I.034 | bromo | thietan-2-ylmethyl- |
| I.035 | bromo | thietan-3-yl- |
| I.036 | bromo | thietan-3-ylmethyl- |
| I.037 | iodo | (1,1-dioxothietan-2-yl)methyl- |
| I.038 | iodo | (1-oxothietan-2-yl)methyl- |
| I.039 | iodo | 1,1-Dioxo-thietan-3-yl- |
| I.040 | iodo | 1,1-Dioxo-thietan-3-ylmethyl- |
| I.041 | CHO | trans-1-oxo-thietan-3-yl- |
| I.042 | CN | trans-1-oxo-thietan-3-yl- |

TABLE I-continued

| | X5 | R2 |
|---|---|---|
| I.043 | iodo | 2-(1,1-dioxothietan-3-yl)ethanyl |
| I.044 | iodo | 2-(1-oxothietan-3-yl)ethanyl |
| I.045 | iodo | 2-(thietan-3-yl)ethanyl |
| I.046 | iodo | 2,2-dimethyl-1,1-Dioxo-thietan-3-yl- |
| I.047 | iodo | 2,2-dimethyl-1-oxo-thietan-3-yl- |
| I.048 | iodo | 2,2-dimethylthietan-3-yl- |
| I.049 | iodo | 3-Methyl-1,1-Dioxo-thietan-3-yl- |
| I.050 | iodo | 3-Methyl-1-oxo-thietan-3-yl- |
| I.051 | iodo | 3-Methyl-thietan-3-yl- |
| I.052 | iodo | thietan-2-ylmethyl- |
| I.053 | iodo | thietan-3-yl- |
| I.054 | iodo | thietan-3-ylmethyl- |
| I.055 | amino | (1,1-dioxothietan-2-yl)methyl- |
| I.056 | amino | (1-oxothietan-2-yl)methyl- |
| I.057 | amino | 1,1-Dioxo-thietan-3-yl- |
| I.058 | amino | 1,1-Dioxo-thietan-3-ylmethyl- |
| I.059 | OH | trans-1-oxo-thietan-3-yl- |
| I.060 | C(=O)OH | trans-1-oxo-thietan-3-yl- |
| I.061 | amino | 2-(1,1-dioxothietan-3-yl)ethanyl |
| I.062 | amino | 2-(1-oxothietan-3-yl)ethanyl |
| I.063 | amino | 2-(thietan-3-yl)ethanyl |
| I.064 | amino | 2,2-dimethyl-1,1-Dioxo-thietan-3-yl- |
| I.065 | amino | 2,2-dimethyl-1-oxo-thietan-3-yl- |
| I.066 | amino | 2,2-dimethylthietan-3-yl- |
| I.067 | amino | 3-Methyl-1,1-Dioxo-thietan-3-yl- |
| I.068 | amino | 3-Methyl-1-oxo-thietan-3-yl- |
| I.069 | amino | 3-Methyl-thietan-3-yl- |
| I.070 | amino | thietan-2-ylmethyl- |
| I.071 | amino | thietan-3-yl- |
| I.072 | amino | thietan-3-ylmethyl- |
| I.073 | CHO | (1,1-dioxothietan-2-yl)methyl- |
| I.074 | CHO | (1-oxothietan-2-yl)methyl- |
| I.075 | CHO | 1,1-Dioxo-thietan-3-yl- |
| I.076 | CHO | 1,1-Dioxo-thietan-3-ylmethyl- |
| I.077 | C(=NOH)H | trans-1-oxo-thietan-3-yl- |
| I.078 | C(=NOH)Cl | trans-1-oxo-thietan-3-yl- |
| I.079 | CHO | 2-(1,1-dioxothietan-3-yl)ethanyl |
| I.080 | CHO | 2-(1-oxothietan-3-yl)ethanyl |
| I.081 | CHO | 2-(thietan-3-yl)ethanyl |
| I.082 | CHO | 2,2-dimethyl-1,1-Dioxo-thietan-3-yl- |
| I.083 | CHO | 2,2-dimethyl-1-oxo-thietan-3-yl- |
| I.084 | CHO | 2,2-dimethylthietan-3-yl- |
| I.085 | CHO | 3-Methyl-1,1-Dioxo-thietan-3-yl- |
| I.086 | CHO | 3-Methyl-1-oxo-thietan-3-yl- |
| I.087 | CHO | 3-Methyl-thietan-3-yl- |
| I.088 | CHO | thietan-2-ylmethyl- |
| I.089 | CHO | thietan-3-yl- |
| I.090 | CHO | thietan-3-ylmethyl- |
| I.091 | CN | (1,1-dioxothietan-2-yl)methyl- |
| I.092 | CN | (1-oxothietan-2-yl)methyl- |
| I.093 | CN | 1,1-Dioxo-thietan-3-yl- |
| I.094 | CN | 1,1-Dioxo-thietan-3-ylmethyl- |
| I.095 | C(=NOH)NH$_2$ | trans-1-oxo-thietan-3-yl- |
| I.096 | C(=O)CH$_3$ | trans-1-oxo-thietan-3-yl- |
| I.097 | CN | 2-(1,1-dioxothietan-3-yl)ethanyl |
| I.098 | CN | 2-(1-oxothietan-3-yl)ethanyl |
| I.099 | CN | 2-(thietan-3-yl)ethanyl |
| I.100 | CN | 2,2-dimethyl-1,1-Dioxo-thietan-3-yl- |
| I.101 | CN | 2,2-dimethyl-1-oxo-thietan-3-yl- |
| I.102 | CN | 2,2-dimethylthietan-3-yl- |
| I.103 | CN | 3-Methyl-1,1-Dioxo-thietan-3-yl- |
| I.104 | CN | 3-Methyl-1-oxo-thietan-3-yl- |
| I.105 | CN | 3-Methyl-thietan-3-yl- |
| I.106 | CN | thietan-2-ylmethyl- |
| I.107 | CN | thietan-3-yl- |
| I.108 | CN | thietan-3-ylmethyl- |
| I.109 | OH | (1,1-dioxothietan-2-yl)methyl- |
| I.110 | OH | (1-oxothietan-2-yl)methyl- |
| I.111 | OH | 1,1-Dioxo-thietan-3-yl- |
| I.112 | OH | 1,1-Dioxo-thietan-3-ylmethyl- |
| I.113 | C(=NOH)CH$_3$ | trans-1-oxo-thietan-3-yl- |
| I.114 | C(=O)CH$_2$Cl | trans-1-oxo-thietan-3-yl- |
| I.115 | OH | 2-(1,1-dioxothietan-3-yl)ethanyl |
| I.116 | OH | 2-(1-oxothietan-3-yl)ethanyl |
| I.117 | OH | 2-(thietan-3-yl)ethanyl |
| I.118 | OH | 2,2-dimethyl-1,1-Dioxo-thietan-3-yl- |
| I.119 | OH | 2,2-dimethyl-1-oxo-thietan-3-yl- |
| I.120 | OH | 2,2-dimethylthietan-3-yl- |
| I.121 | OH | 3-Methyl-1,1-Dioxo-thietan-3-yl- |
| I.122 | OH | 3-Methyl-1-oxo-thietan-3-yl- |
| I.123 | OH | 3-Methyl-thietan-3-yl- |
| I.124 | OH | thietan-2-ylmethyl- |
| I.125 | OH | thietan-3-yl- |
| I.126 | OH | thietan-3-ylmethyl- |
| I.127 | C(=O)OH | (1,1-dioxothietan-2-yl)methyl- |
| I.128 | C(=O)OH | (1-oxothietan-2-yl)methyl- |
| I.129 | C(=O)OH | 1,1-Dioxo-thietan-3-yl- |
| I.130 | C(=O)OH | 1,1-Dioxo-thietan-3-ylmethyl- |
| I.131 | C(=O)CH$_2$Br | trans-1-oxo-thietan-3-yl- |
| I.132 | chloro | cis-1-oxo-thietan-3-ylmethyl- |
| I.133 | C(=O)OH | 2-(1,1-dioxothietan-3-yl)ethanyl |
| I.134 | C(=O)OH | 2-(1-oxothietan-3-yl)ethanyl |
| I.135 | C(=O)OH | 2-(thietan-3-yl)ethanyl |
| I.136 | C(=O)OH | 2,2-dimethyl-1,1-Dioxo-thietan-3-yl- |
| I.137 | C(=O)OH | 2,2-dimethyl-1-oxo-thietan-3-yl- |
| I.138 | C(=O)OH | 2,2-dimethylthietan-3-yl- |
| I.139 | C(=O)OH | 3-Methyl-1,1-Dioxo-thietan-3-yl- |
| I.140 | C(=O)OH | 3-Methyl-1-oxo-thietan-3-yl- |
| I.141 | C(=O)OH | 3-Methyl-thietan-3-yl- |
| I.142 | C(=O)OH | thietan-2-ylmethyl- |
| I.143 | C(=O)OH | thietan-3-yl- |
| I.144 | C(=O)OH | thietan-3-ylmethyl- |
| I.145 | C(=NOH)H | (1,1-dioxothietan-2-yl)methyl- |
| I.146 | C(=NOH)H | (1-oxothietan-2-yl)methyl- |
| I.147 | C(=NOH)H | 1,1-Dioxo-thietan-3-yl- |
| I.148 | C(=NOH)H | 1,1-Dioxo-thietan-3-ylmethyl- |
| I.149 | bromo | cis-1-oxo-thietan-3-ylmethyl- |
| I.150 | iodo | cis-1-oxo-thietan-3-ylmethyl- |
| I.151 | C(=NOH)H | 2-(1,1-dioxothietan-3-yl)ethanyl |
| I.152 | C(=NOH)H | 2-(1-oxothietan-3-yl)ethanyl |
| I.153 | C(=NOH)H | 2-(thietan-3-yl)ethanyl |
| I.154 | C(=NOH)H | 2,2-dimethyl-1,1-Dioxo-thietan-3-yl- |
| I.155 | C(=NOH)H | 2,2-dimethyl-1-oxo-thietan-3-yl- |
| I.156 | C(=NOH)H | 2,2-dimethylthietan-3-yl- |
| I.157 | C(=NOH)H | 3-Methyl-1,1-Dioxo-thietan-3-yl- |
| I.158 | C(=NOH)H | 3-Methyl-1-oxo-thietan-3-yl- |
| I.159 | C(=NOH)H | 3-Methyl-thietan-3-yl- |
| I.160 | C(=NOH)H | thietan-2-ylmethyl- |
| I.161 | C(=NOH)H | thietan-3-yl- |
| I.162 | C(=NOH)H | thietan-3-ylmethyl- |
| I.163 | C(=NOH)Cl | (1,1-dioxothietan-2-yl)methyl- |
| I.164 | C(=NOH)Cl | (1-oxothietan-2-yl)methyl- |
| I.165 | C(=NOH)Cl | 1,1-Dioxo-thietan-3-yl- |
| I.166 | C(=NOH)Cl | 1,1-Dioxo-thietan-3-ylmethyl- |
| I.167 | amino | cis-1-oxo-thietan-3-ylmethyl- |
| I.168 | CHO | cis-1-oxo-thietan-3-ylmethyl- |
| I.169 | C(=NOH)Cl | 2-(1,1-dioxothietan-3-yl)ethanyl |
| I.170 | C(=NOH)Cl | 2-(1-oxothietan-3-yl)ethanyl |
| I.171 | C(=NOH)Cl | 2-(thietan-3-yl)ethanyl |
| I.172 | C(=NOH)Cl | 2,2-dimethyl-1,1-Dioxo-thietan-3-yl- |
| I.173 | C(=NOH)Cl | 2,2-dimethyl-1-oxo-thietan-3-yl- |
| I.174 | C(=NOH)Cl | 2,2-dimethylthietan-3-yl- |
| I.175 | C(=NOH)Cl | 3-Methyl-1,1-Dioxo-thietan-3-yl- |
| I.176 | C(=NOH)Cl | 3-Methyl-1-oxo-thietan-3-yl- |
| I.177 | C(=NOH)Cl | 3-Methyl-thietan-3-yl- |
| I.178 | C(=NOH)Cl | thietan-2-ylmethyl- |
| I.179 | C(=NOH)Cl | thietan-3-yl- |
| I.180 | C(=NOH)Cl | thietan-3-ylmethyl- |
| I.181 | C(=NOH)NH$_2$ | (1,1-dioxothietan-2-yl)methyl- |
| I.182 | C(=NOH)NH$_2$ | (1-oxothietan-2-yl)methyl- |
| I.183 | C(=NOH)NH$_2$ | 1,1-Dioxo-thietan-3-yl- |
| I.184 | C(=NOH)NH$_2$ | 1,1-Dioxo-thietan-3-ylmethyl- |
| I.185 | CN | cis-1-oxo-thietan-3-ylmethyl- |
| I.186 | OH | cis-1-oxo-thietan-3-ylmethyl- |
| I.187 | C(=NOH)NH$_2$ | 2-(1,1-dioxothietan-3-yl)ethanyl |
| I.188 | C(=NOH)NH$_2$ | 2-(1-oxothietan-3-yl)ethanyl |
| I.189 | C(=NOH)NH$_2$ | 2-(thietan-3-yl)ethanyl |
| I.190 | C(=NOH)NH$_2$ | 2,2-dimethyl-1,1-Dioxo-thietan-3-yl- |
| I.191 | C(=NOH)NH$_2$ | 2,2-dimethyl-1-oxo-thietan-3-yl- |
| I.192 | C(=NOH)NH$_2$ | 2,2-dimethylthietan-3-yl- |
| I.193 | C(=NOH)NH$_2$ | 3-Methyl-1,1-Dioxo-thietan-3-yl- |
| I.194 | C(=NOH)NH$_2$ | 3-Methyl-1-oxo-thietan-3-yl- |
| I.195 | C(=NOH)NH$_2$ | 3-Methyl-thietan-3-yl- |
| I.196 | C(=NOH)NH$_2$ | thietan-2-ylmethyl- |
| I.197 | C(=NOH)NH$_2$ | thietan-3-yl- |
| I.198 | C(=NOH)NH$_2$ | thietan-3-ylmethyl- |

TABLE I-continued

| | X5 | R2 |
|---|---|---|
| I.199 | C(=O)CH₃ | (1,1-dioxothietan-2-yl)methyl- |
| I.200 | C(=O)CH₃ | (1-oxothietan-2-yl)methyl- |
| I.201 | C(=O)CH₃ | 1,1-Dioxo-thietan-3-yl- |
| I.202 | C(=O)CH₃ | 1,1-Dioxo-thietan-3-ylmethyl- |
| I.203 | C(=O)OH | cis-1-oxo-thietan-3-ylmethyl- |
| I.204 | C(=NOH)H | cis-1-oxo-thietan-3-ylmethyl- |
| I.205 | C(=O)CH₃ | 2-(1,1-dioxothietan-3-yl)ethanyl |
| I.206 | C(=O)CH₃ | 2-(1-oxothietan-3-yl)ethanyl |
| I.207 | C(=O)CH₃ | 2-(thietan-3-yl)ethanyl |
| I.208 | C(=O)CH₃ | 2,2-dimethyl-1,1-Dioxo-thietan-3-yl- |
| I.209 | C(=O)CH₃ | 2,2-dimethyl-1-oxo-thietan-3-yl- |
| I.210 | C(=O)CH₃ | 2,2-dimethylthietan-3-yl- |
| I.211 | C(=O)CH₃ | 3-Methyl-1,1-Dioxo-thietan-3-yl- |
| I.212 | C(=O)CH₃ | 3-Methyl-1-oxo-thietan-3-yl- |
| I.213 | C(=O)CH₃ | 3-Methyl-thietan-3-yl- |
| I.214 | C(=O)CH₃ | thietan-2-ylmethyl- |
| I.215 | C(=O)CH₃ | thietan-3-yl- |
| I.216 | C(=O)CH₃ | thietan-3-ylmethyl- |
| I.217 | C(=NOH)CH₃ | (1,1-dioxothietan-2-yl)methyl- |
| I.218 | C(=NOH)CH₃ | (1-oxothietan-2-yl)methyl- |
| I.219 | C(=NOH)CH₃ | 1,1-Dioxo-thietan-3-yl- |
| I.220 | C(=NOH)CH₃ | 1,1-Dioxo-thietan-3-ylmethyl- |
| I.221 | C(=NOH)Cl | cis-1-oxo-thietan-3-ylmethyl- |
| I.222 | C(=NOH)NH₂ | cis-1-oxo-thietan-3-ylmethyl- |
| I.223 | C(=NOH)CH₃ | 2-(1,1-dioxothietan-3-yl)ethanyl |
| I.224 | C(=NOH)CH₃ | 2-(1-oxothietan-3-yl)ethanyl |
| I.225 | C(=NOH)CH₃ | 2-(thietan-3-yl)ethanyl |
| I.226 | C(=NOH)CH₃ | 2,2-dimethyl-1,1-Dioxo-thietan-3-yl- |
| I.227 | C(=NOH)CH₃ | 2,2-dimethyl-1-oxo-thietan-3-yl- |
| I.228 | C(=NOH)CH₃ | 2,2-dimethylthietan-3-yl- |
| I.229 | C(=NOH)CH₃ | 3-Methyl-1,1-Dioxo-thietan-3-yl- |
| I.230 | C(=NOH)CH₃ | 3-Methyl-1-oxo-thietan-3-yl- |
| I.231 | C(=NOH)CH₃ | 3-Methyl-thietan-3-yl- |
| I.232 | C(=NOH)CH₃ | thietan-2-ylmethyl- |
| I.233 | C(=NOH)CH₃ | thietan-3-yl- |
| I.234 | C(=NOH)CH₃ | thietan-3-ylmethyl- |
| I.235 | C(=O)CH₂Cl | (1,1-dioxothietan-2-yl)methyl- |
| I.236 | C(=O)CH₂Cl | (1-oxothietan-2-yl)methyl- |
| I.237 | C(=O)CH₂Cl | 1,1-Dioxo-thietan-3-yl- |
| I.238 | C(=O)CH₂Cl | 1,1-Dioxo-thietan-3-ylmethyl- |
| I.239 | C(=O)CH₃ | cis-1-oxo-thietan-3-ylmethyl- |
| I.240 | C(=NOH)CH₃ | cis-1-oxo-thietan-3-ylmethyl- |
| I.241 | C(=O)CH₂Cl | 2-(1,1-dioxothietan-3-yl)ethanyl |
| I.242 | C(=O)CH₂Cl | 2-(1-oxothietan-3-yl)ethanyl |
| I.243 | C(=O)CH₂Cl | 2-(thietan-3-yl)ethanyl |
| I.244 | C(=O)CH₂Cl | 2,2-dimethyl-1,1-Dioxo-thietan-3-yl- |
| I.245 | C(=O)CH₂Cl | 2,2-dimethyl-1-oxo-thietan-3-yl- |
| I.246 | C(=O)CH₂Cl | 2,2-dimethylthietan-3-yl- |
| I.247 | C(=O)CH₂Cl | 3-Methyl-1,1-Dioxo-thietan-3-yl- |
| I.248 | C(=O)CH₂Cl | 3-Methyl-1-oxo-thietan-3-yl- |
| I.249 | C(=O)CH₂Cl | 3-Methyl-thietan-3-yl- |
| I.250 | C(=O)CH₂Cl | thietan-2-ylmethyl- |
| I.251 | C(=O)CH₂Cl | thietan-3-yl- |
| I.252 | C(=O)CH₂Cl | thietan-3-ylmethyl- |
| I.253 | C(=O)CH₂Br | (1,1-dioxothietan-2-yl)methyl- |
| I.254 | C(=O)CH₂Br | (1-oxothietan-2-yl)methyl- |
| I.255 | C(=O)CH₂Br | 1,1-Dioxo-thietan-3-yl- |
| I.256 | C(=O)CH₂Br | 1,1-Dioxo-thietan-3-ylmethyl- |
| I.257 | C(=O)CH₂Cl | cis-1-oxo-thietan-3-ylmethyl- |
| I.258 | C(=O)CH₂Br | cis-1-oxo-thietan-3-ylmethyl- |
| I.259 | C(=O)CH₂Br | 2-(1,1-dioxothietan-3-yl)ethanyl |
| I.260 | C(=O)CH₂Br | 2-(1-oxothietan-3-yl)ethanyl |
| I.261 | C(=O)CH₂Br | 2-(thietan-3-yl)ethanyl |
| I.262 | C(=O)CH₂Br | 2,2-dimethyl-1,1-Dioxo-thietan-3-yl- |
| I.263 | C(=O)CH₂Br | 2,2-dimethyl-1-oxo-thietan-3-yl- |
| I.264 | C(=O)CH₂Br | 2,2-dimethylthietan-3-yl- |
| I.265 | C(=O)CH₂Br | 3-Methyl-1,1-Dioxo-thietan-3-yl- |
| I.266 | C(=O)CH₂Br | 3-Methyl-1-oxo-thietan-3-yl- |
| I.267 | C(=O)CH₂Br | 3-Methyl-thietan-3-yl- |
| I.268 | C(=O)CH₂Br | thietan-2-ylmethyl- |
| I.269 | C(=O)CH₂Br | thietan-3-yl- |
| I.270 | C(=O)CH₂Br | thietan-3-ylmethyl- |
| I.271 | chloro | cis-1-oxo-thietan-3-yl- |
| I.272 | bromo | cis-1-oxo-thietan-3-yl- |
| I.273 | iodo | cis-1-oxo-thietan-3-yl- |
| I.274 | amino | cis-1-oxo-thietan-3-yl- |
| I.275 | CHO | cis-1-oxo-thietan-3-yl- |
| I.276 | CN | cis-1-oxo-thietan-3-yl- |
| I.277 | OH | cis-1-oxo-thietan-3-yl- |
| I.278 | C(=O)OH | cis-1-oxo-thietan-3-yl- |
| I.279 | C(=NOH)H | cis-1-oxo-thietan-3-yl- |
| I.280 | C(=NOH)Cl | cis-1-oxo-thietan-3-yl- |
| I.281 | C(=NOH)NH₂ | cis-1-oxo-thietan-3-yl- |
| I.282 | C(=O)CH₃ | cis-1-oxo-thietan-3-yl- |
| I.283 | C(=NOH)CH₃ | cis-1-oxo-thietan-3-yl- |
| I.284 | C(=O)CH₂Cl | cis-1-oxo-thietan-3-yl- |
| I.285 | C(=O)CH₂Br | cis-1-oxo-thietan-3-yl- |
| I.286 | chloro | trans-1-oxo-thietan-3-ylmethyl- |
| I.287 | bromo | trans-1-oxo-thietan-3-ylmethyl- |
| I.288 | iodo | trans-1-oxo-thietan-3-ylmethyl- |
| I.289 | amino | trans-1-oxo-thietan-3-ylmethyl- |
| I.290 | CHO | trans-1-oxo-thietan-3-ylmethyl- |
| I.291 | CN | trans-1-oxo-thietan-3-ylmethyl- |
| I.292 | OH | trans-1-oxo-thietan-3-ylmethyl- |
| I.293 | C(=O)OH | trans-1-oxo-thietan-3-ylmethyl- |
| I.294 | C(=NOH)H | trans-1-oxo-thietan-3-ylmethyl- |
| I.295 | C(=NOH)Cl | trans-1-oxo-thietan-3-ylmethyl- |
| I.296 | C(=NOH)NH₂ | trans-1-oxo-thietan-3-ylmethyl- |
| I.297 | C(=O)CH₃ | trans-1-oxo-thietan-3-ylmethyl- |
| I.298 | C(=NOH)CH₃ | trans-1-oxo-thietan-3-ylmethyl- |
| I.299 | C(=O)CH₂Cl | trans-1-oxo-thietan-3-ylmethyl- |
| I.300 | C(=O)CH₂Br | trans-1-oxo-thietan-3-ylmethyl- |

The structures of R² indicated in Tables 1 to 182 is indicated in the table below:

| R² | structure |
|---|---|
| (1,1-dioxothietan-2-yl)methyl- | 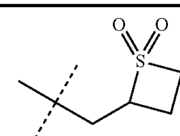 |
| (1-oxothietan-2-yl)methyl- | 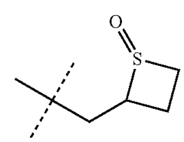 |
| 1,1-Dioxo-thietan-3-yl- | 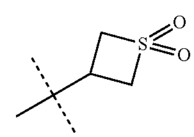 |
| 1,1-Dioxo-thietan-3-ylmethyl- | 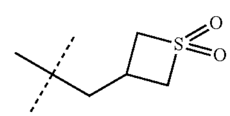 |
| cis-1-oxo-thietan-3-yl- | 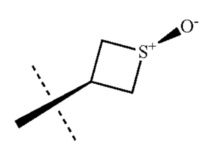 |
| cis-1-oxo-thietan-3-ylmethyl- | 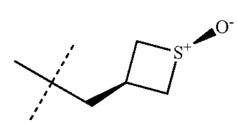 |
| 2-(1,1-dioxothietan-3-yl)ethanyl | 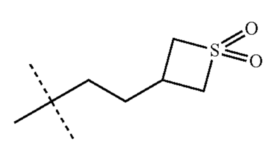 |

| R² | structure |
|---|---|
| 2-(1-oxothietan-3-yl)ethanyl | 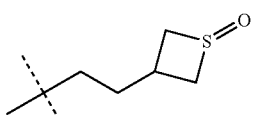 |
| 2-(thietan-3-yl)ethanyl | 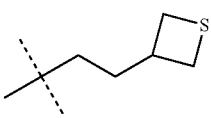 |
| 2,2-dimethyl-1,1-Dioxo-thietan-3-yl- | 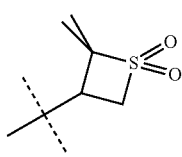 |
| 2,2-dimethyl-1-oxo-thietan-3-yl- | 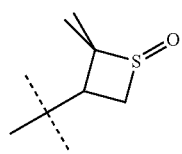 |
| 2,2-dimethylthietan-3-yl- | 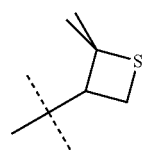 |
| 3-Methyl-1,1-Dioxo-thietan-3-yl- | 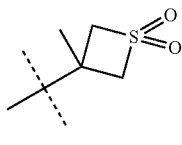 |
| 3-Methyl-1-oxo-thietan-3-yl- | 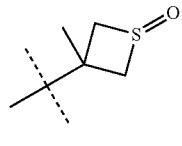 |
| 3-Methyl-thietan-3-yl- | 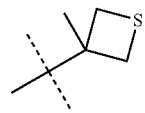 |
| thietan-2-ylmethyl- | 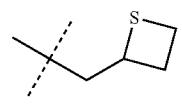 |
| thietan-3-yl- | 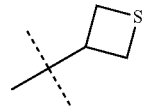 |
| thietan-3-ylmethyl- | 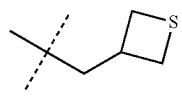 |

| R² | structure |
|---|---|
| trans-1-oxo-thietan-3-yl- | 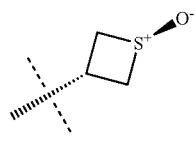 |
| trans-1-oxo-thietan-3-ylmethyl- | 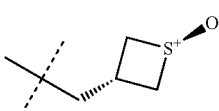 |

In one embodiment the invention provides a compound selected from Tables 1 to 36 for use in controlling and/or preventing insects of the family Curculionidae, preferably in for use in controlling and/or preventing *Anthonomus grandis*.

Additional examples of insects from the family of Curculionidae are *Anthonomus corvulus, Anthonomus elutus, Anthonomus elongatus, Anthonomus eugenii, Anthonomus consors, Anthonomus haematopus, Anthonomus lecontei, Anthonomus molochinus, Anthonomus morticinus, Anthonomus musculus, Anthonomus nigrinus, Anthonomus phyllocola, Anthonomus pictus, Anthonomus pomorum, Anthonomus quadrigibbus, Anthonomus rectirostris, Anthonomus rubi, Anthonomus santacruzi, Anthonomus signatus, Anthonomus subfasciatus*, and *Anthonomus tenebrosus*.

In one embodiment the invention provides a compound selected from Tables 1 to 36 for use against *Anthonomus grandis* in cotton.

In one embodiment the invention provides a compound selected from Tables 1 to 36 for use in controlling and/or preventing soil pests.

In one embodiment the invention provides a compound selected from Tables 1 to 36 for use in controlling and/or preventing corn rootworm, in particular for use against corn root worm from the genus *Diabrotica*.

In one embodiment the invention provides a compound selected from Tables 1 to 36 for use in controlling and/or preventing *Diabrotica virgifera*.

In one embodiment the invention provides a compound selected from Tables 1 to 36 for use in controlling and/or preventing *Diabrotica barberi*.

In one embodiment the invention provides a compound selected from Tables 1 to 36 for use in controlling and/or preventing *Diabrotica undecimpunctata howardi*.

In one embodiment the invention provides a compound selected from Tables 1 to 36 for use in controlling and/or preventing wireworms, in particular *Agriotes* spp.

In one embodiment the invention provides a compound selected from Tables 1 to 36 for use in controlling and/or preventing *Agriotes* spp. in cereals, potato or corn.

Additional examples of *Agriotes* spp. include *Agriotes lineatus, Agriotes obscurus, Agriotes brevis, Agriotes gurgistanus, Agriotes sputator, Agriotes ustulatus, Ctenicera destructor*, and *Limonius californicus*.

In one embodiment the invention provides a compound selected from Tables 1 to 36 for use in controlling and/or preventing grubs, in particular white grubs.

In one embodiment the invention provides a compound selected from Tables 1 to 36 for use in controlling and/or preventing *Phyllophaga* spp., particularly on corn, soybean or cotton.

In one embodiment the invention provides a compound selected from Tables 1 to 36 for use in controlling and/or preventing *Diloboderus* spp. particularly on corn, soybean or cotton.

In one embodiment the invention provides a compound selected from Tables 1 to 36 for use in controlling and/or preventing *Popillia japonica*, particularly on corn, soybean or cotton.

Additional examples of white grubs include *Phyllophaga anxia, Phyllophaga crinite, Phyllophaga subnitida, Diloboderus abderus*.

In one embodiment the invention provides a compound selected from Tables 1 to 36 for use in controlling and/or preventing termites, e.g. on sugarcane.

Examples of termites include *Reticulitermes, Coptotermes, Macrotermes, Microtermes, Globitermes*. Specific of subterranean termites include *Reticulitermes jlavipes, Reticulitermes hesperus, Reticulitermes verginicus, Reticulitermes hageni, Reticulitermes speratus, Reticulitermes lucifugus, Heterotermes aureus, Coptotermes formosanus, Coptotermes acinaciformis, Coptotermes curvignathus, Nasutitermes exitiosus, Nasutitermes walkeri, Mastotermes darwiniensis, Schedorhinotermes* spp, *Macrotermes bellicosus, Macrotermes* spp., *Globitermes sulphureus, Odontotermes* spp. Specific examples of dry wood termites include *Incisitermes minor, Marginitermes hubbardi, Cryptotermes brevis, Kalotermes jlavicollis*. Additional examples of termites include *procornitermes* spp. and *procornitermes araujoi*

In one embodiment the invention provides a compound selected from Tables 1 to 36 for use in controlling and/or preventing subterraneous stinkbugs, e.g. *Scaptocoris* spp.

In one embodiment the invention provides a compound selected from Tables 1 to 36 for use in controlling and/or preventing *Scaptocoris castaneus*, in particular on cereals, soybean or corn.

In one embodiment the invention provides a compound selected from Tables 1 to 36 for use in controlling and/or preventing cutworms, e.g. *agrotis* spp.

In one embodiment the invention provides a compound selected from Tables 1 to 36 for use in controlling and/or preventing *Agrotis ipsilon*, particularly on cereals, canola, soybean or corn.

In one embodiment the invention provides a compound selected from Tables 1 to 36 for use in controlling and/or preventing millipedes, e.g. *Julus* spp.

In one embodiment the invention provides a compound selected from Tables 1 to 36 for use in controlling and/or preventing *Julus* spp., particularly on cereals, canola, soybean & corn.

In one embodiment the invention provides a compound selected from Tables 1 to 36 for use in controlling and/or preventing broca gigante, e.g. *Telchin licus*, particularly on sugarcane.

In one embodiment the invention provides a compound selected from Tables 1 to 36 for use in controlling and/or preventing whitefly.

In one embodiment the invention provides a compound selected from Tables 1 to 36 for use in controlling and/or preventing *Bemisia tabaci*, particularly on vegetables, cotton, soybean, or potatoes.

In one embodiment the invention provides a compound selected from Tables 1 to 36 for use in controlling and/or preventing *Trialeurodes vaporariorum*, particularly on vegetables, cotton, soybean, or potatoes.

In one embodiment the invention provides a compound selected from Tables 1 to 36 for use in controlling and/or preventing stinkbugs, in particular *Euschistus* spp.

In one embodiment the invention provides a compound selected from Tables 1 to 36 for use in controlling and/or preventing *Euschistus* spp., particularly in soybean.

Examples of stinkbugs include *Nezara* spp. (e.g. *Nezara viridula, Nezara antennata, Nezara hilare*), *Piezodorus* spp. (e.g. *Piezodorus guildinii*), *Acrosternum* spp. *Euchistus* spp. (e.g. *Euchistus heros, Euschistus servus*), *Halyomorpha halys, Plautia crossota, Riptortus clavatus, Rhopalus msculatus, Antestiopsis orbitalus, Dichelops* spp. (e.g. *Dichelops furcatus, Dichelops melacanthus*), *Eurygaster* spp. (e.g. *Eurygaster intergriceps, Eurygaster maura*), *Oebalus* spp. (e.g. *Oebalus mexicana, Oebalus poecilus, Oebalus pugnase, Scotinophara* spp. (e.g. *Scotinophara lurida, Scotinophara coarctata*). Preferred targets include *Antestiopsis orbitalus, Dichelops furcatus, Dichelops melacanthus, Euchistus heros, Euschistus servus, Nezara viridula, Nezara hilare, Piezodorus guildinii, Halyomorpha halys*. In one embodiment the stinkbug target is *Nezara viridula, Piezodorus* spp., *Acrosternum* spp, *Euchistus heros*.

In one embodiment the invention provides a compound selected from Tables 1 to 36 for use against rice pests.

In one embodiment the invention provides a compound selected from Tables 1 to 36 for use against stemborer, particularly in rice.

Examples of stemborers include *Chilo* sp, *Chilo suppressalis, Chilo polychrysus, Chilo auricilius, Scirpophaga* spp., *Scirpophaga incertulas, Scirpophaga innotata, Scirpophaga nivella Sesamia* sp, *Sesamia inferens*.

In one embodiment the invention provides a compound selected from Tables 1 to 36 for use against leaffolder, particularly in rice.

Examples of leaffolders include *Cnaphalocrocis* spp., *Cnaphalocrocis medinalis, Marasmia* spp., *Marasmia patnalis, Marasmia exigua*.

In one embodiment the invention provides a compound selected from Tables 1 to 36 for use against hoppers, particularly in rice.

Examples of Hoppers include *Nephotettix* spp., *Nephotettix virescens, Nephotettix nigropictus, Nephotettix malayanus, Nephotettix cincticeps, Nilaparvata lugens, Sogatella furcifera*.

In one embodiment the invention provides a compound selected from Tables 1 to 36 for use against gallmidge, particularly in rice.

Examples of Gall midge include *Orseolia* sp, *Orseolia oryzae*.

In one embodiment the invention provides a compound selected from Tables 1 to 36 for use against whorl maggot, particularly in rice.

Examples of whorl maggots include *Hydrellia* sp, *Hydrellia philippina*.

In one embodiment the invention provides a compound selected from Tables 1 to 36 for use against Rice bugs, particularly in rice.

Examples of rice bugs include *Leptocorisa* sp, *Leptocorisa oratorius, Leptocorisa chinensis, Leptocorisa acuta*.

In one embodiment the invention provides a compound selected from Tables 1 to 36 for use against Black bugs, particularly in rice.

Examples of Black bugs include *Scotinophara* sp, *Scotinophara coarctata, Scotinophara lurida, Scotinophara latiuscula*.

In one embodiment the invention provides a compound selected from Tables 1 to 36 for use against *plutella* spp.

In one embodiment the invention provides a compound selected from Tables 1 to 36 for use against *Plutella xylostella*, particularly in *brassica* crops.

Compounds of formula I include at least one chiral centre and may exist as compounds of formula I* or compounds of formula I**. Compounds I* and I** are enantiomers if there is no other chiral center or epimers otherwise.

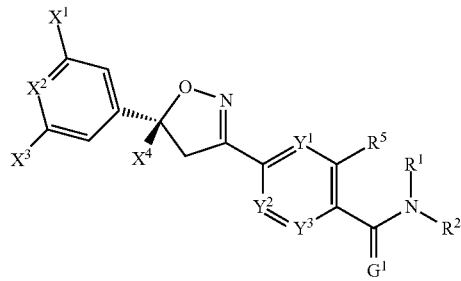

(I*)

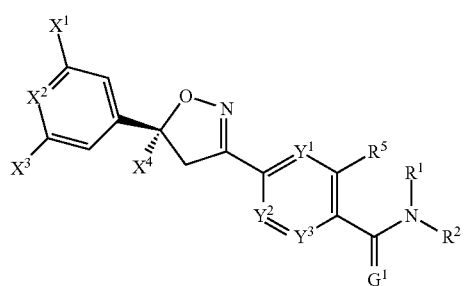

(I**)

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimerically) is for example greater than 50%, e.g. at least 55, 60, 65, 70, 75, 80, 85, 90, 95, 96, 97, 98, or at least 99%. Enantiomerically (or epimerically) enriched mixtures of formula I are preferred. Where compounds of formula I contain an SO group, cis SO groups are preferred. When compounds of formula I contain an SO group, cis SO groups are preferred. Each of the compounds disclosed in the above Tables, namely Tables 1 to 108 represents a specific disclosure of a compound with the R configuration (i.e. at the corresponding position indicated for compounds I* and I**) and a specific disclosure of a compound having the S configuration (i.e. at the corresponding position indicated for compounds I* and I**).

Compounds of formula I can be prepared according to the schemes illustrated in WO2010/025998 and WO2009/08050 which are incorporated herein by reference. Further details regarding possible routes to the compounds of the invention are given below.

Scheme 1

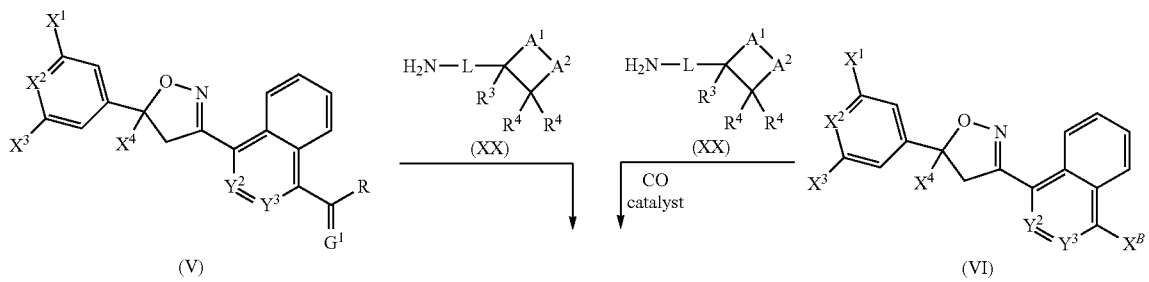

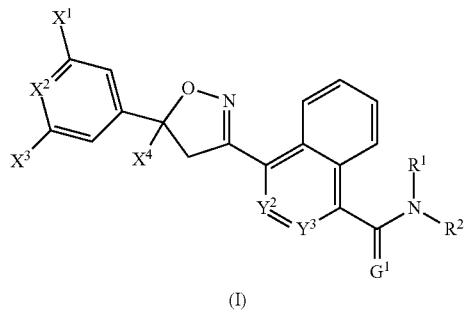

(I)

1) Compounds of formula (I) can be prepared by reacting a compound of formula (V) wherein R is OH, $C_1$-$C_6$alkoxy or Cl, F or Br, with an amine of formula (XX), wherein L is methylene or ethylene, as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. It is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature from 0° C. to 100° C., preferably from 15° C. to 30° C., in particular at ambient temperature Amines of formula (XX) are either known in the literature or can be prepared using methods known to a person skilled in the art. Some of these methods are described in the preparation examples.

2) Acid halides of formula (V), wherein R is Cl, F or Br, may be made from carboxylic acids of formula (V), wherein R is OH, under standard conditions, as described for example in WO2008/128711.

3) Carboxylic acids of formula (V), wherein R is OH, may be formed from esters of formula (V), wherein R is $C_1$-$C_6$alkoxy as described for example in WO2009/072621.

4) Compounds of formula (I) can be prepared by reacting a compound of formula (VI) wherein $X^B$ is a leaving group, for example a halogen, such as bromo, with carbon monoxide and an amine of formula (XX), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature from 50° C. to 200° C., preferably from 100° C. to 150° C. The reaction is carried out at a pressure of from 50 to 200 bar, preferably from 100 to 150 bar.

5) Compounds of formula (VI) wherein $X^B$ is a leaving group, e.g. halogen, $C_1$-$C_8$alkoxy, $C_1$-$C_8$alkylsulfonyloxy, $C_1$-$C_8$haloalkylsulfonyloxy, $C_1$-$C_8$ arylsulfonyloxy, optionally substituted $C_1$-$C_8$arylsulfonyloxy (aryl is preferably phenyl), diazonium salts (e.g. $X^B$ is $-N_2^+Cl^-$, $-N_2^+BF_4^-$, $-N_2^+Br^-$, $-N_2^+PF_6^-$), phosphonate esters (e.g. $-OP(O)(OR^x)_2$, wherein Rx is methyl or ethyl), preferably bromo, iodo, chloro, trifluoromethylsulfoxy, p-toluenesulfoxy, diazonium chloride, preferably halogen, more preferably bromo, can be made by a various of methods, for example as described in WO2009/080250 and WO2010/025998.

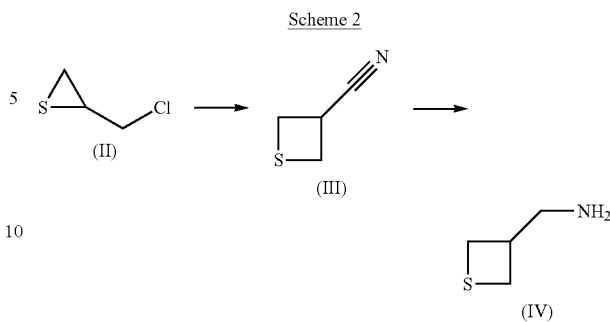

Scheme 2

6) Thietan-3-nitrile (III) can be obtained by reaction of epithiochlorhydrin (II) with a cyanide M-CN, such as sodium cyanide or potassium cyanide in the presence of water, preferably as a co-solvent with an organic solvent such as benzene or tetrahydrofuran, at a temperature of 20° C. to 100° C., preferably 40-60° C. preferably around 50° C.

Water is preferably used as a solvent, more preferably as a co-solvent with an organic solvent, preferably a water-immiscible organic solvent, e.g. such that the reaction then takes place in a biphasic system. The organic co-solvent is preferred to be aprotic, and is more preferably chosen from pentane, hexane, heptane, cyclohexane, benzene, toluene, xylene, tetrahydrofuran, ethyl acetate, diethyl ether, or methyl-tert-butyl ether. The reaction can be performed with an excess of epithiochlorhydrin or with an excess of M-CN, preferably in stoechiometric ratio or slight excess of one or the other reagent.

7) Compounds of formula (IV) can be prepared by reaction of compounds of formula (III) with a suitable reducing reagent. The most suitable, but not exclusive, method is the use of metal hydride reagents, such as lithium aluminum hydride or borane, in the presence or not of cocatalysts. Other methods that can be carried out involve the hydrogenation in the presence of Raney Ni, or palladium for instance. The most common solvents for this reaction are alcohols such as methanol or ethanol, tetrahydrofuran, toluene, ethers, such as diethyl ether or methyl tert-butyl ether. In most cases it is advantageous to conduct the reaction at dilution between 0.1 M to 1 M, preferably 0.3 M to 0.5 M, at a temperature of 0° C. to 100° C., preferably 0-80° C. preferably around 20° C., and the reaction time in most cases is between 30 minutes and 12 hours.

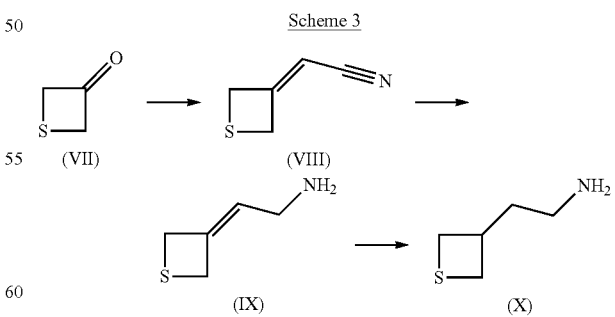

Scheme 3

8) Compounds of formula (VIII) can be obtained by various methods from the thietanone (VII). For example, they can be prepared by performing a wittig reaction or a related reaction, using (triphenylphosphoranylidene)acetonitrile or (Cyanomethyl)diethoxyphosphine oxide as a reagent or following a procedure in analogy to the one described in Organic Letters 2010, 12(9), 1944-1947 and Journal of the American Chemical Society 2009, 131(8), 2786-2787. Such reactions are usually performed in a solvent, such as toluene or dichloromethane, at a temperature of from 0° C. to 150° C., preferably from 0° C. to 50° C. Thietan-3-one (VII) can be prepared according to known methods, for example described in Synlett, (11), 783-4; 1991 or in WO 2007046548.

9) Compounds of formula (IX) can be prepared by reaction of compounds of formula (VIII) with a suitable reducing reagent. The most suitable, but not exclusive, method is the use of metal hydride reagents, such as sodium borohydride. Other methods that can be carried out involve the hydrogenation under a hydrogen atmosphere in the presence of palladium for instance. The most common solvents for this reaction are alcohols such as methanol or ethanol. In most cases it is advantageous to conduct the reaction at dilution between 0.1 M to 1 M, preferably 0.3 M to 0.5 M, at a temperature of 0° C. to 100° C., preferably 0-80° C. preferably around 20° C., and the reaction time in most cases is between 30 minutes and 12 hours.

10) Compounds of formula (X) can be prepared by reaction of compounds of formula (IX) with a suitable reducing reagent. The most suitable, but not exclusive, method is the use of metal hydride reagents, such as lithium aluminum hydride or borane, in the presence or not of cocatalysts. Other methods that can be carried out involve the hydrogenation in the presence of Raney Ni, or palladium for instance. The most common solvents for this reaction are alcohols such as methanol or ethanol, tetrahydrofuran, toluene, ethers, such as diethyl ether or methyl tert-butyl ether. In most cases it is advantageous to conduct the reaction at dilution between 0.1 M to 1 M, preferably 0.3 M to 0.5 M, at a temperature of 0° C. to 100° C., preferably 0-80° C. preferably around 20° C., and the reaction time in most cases is between 30 minutes and 12 hours.

11) Alternatively, compounds of formula (X) may be obtained directly by reduction of compounds of formula (VIII), for example under hydrogenation conditions, e.g. using hydrogen and a metal hydrogenation catalyst, e.g. Palladium, Rhodium, or Plattinum.

For the preparation of the amines, a few other routes can be followed, some of which are represented in schemes 4, 5, 6 and 7.

Scheme 4

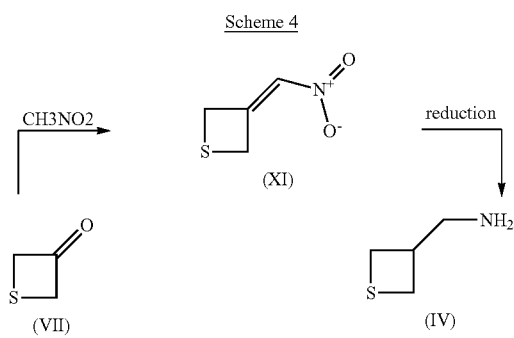

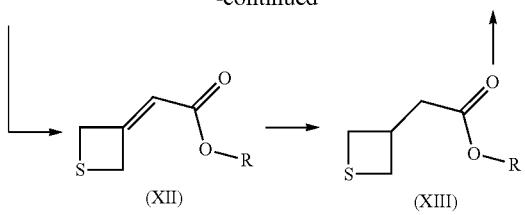

12) Compound (1V) may be prepared by reduction of a nitromethylene compound of formula (XI). Reducing agents suitable for this reduction include for example metal hydride reagents such as sodium borohydride or lithium aluminium hydride optionally in the presence of a catalyst, for example nichel chloride. Hydrogenation in the presence of metal catalyst such as raney nickel or palladium on charcoal is an alternative for such reductions. Examples of such methods can be found in Journal of the American Chemical Society (2003), 125(40), 12125-12136, US patent n° 20050261327, or in Journal of Medicinal Chemistry (2010), 53(7), 2942-2951.

13) Compounds of formula (X1) can be prepared by reaction of the ketone of formula (VII) with nitromethane under standard conditions (Henry reaction), as described for example in Angewandte Chemie, International Edition, 45(46), 7736-7739; 2006 or in Journal of Medicinal Chemistry, 53(8), 3227-3246; 2010.

14) Alternatively, the amine of formula (IV) may be obtained from the carboxylic acid of formula (XIII) using Schmidt or Curtius rearrangement. Schmidt rearrangement involves treatment with hydrazoic acid under a range of possible conditions known to the person skilled of the art, for example as described in Journal of Organic Chemistry, 58(6), 1372-6; 1993 for the conversion of bicyclo[1.1.1]pentane-2-carboxylic acid to bicyclo[1.1.1]pentane-2-amine Curtius rearrangement can be carried out under different possible conditions known to the person skilled in the art, for example treatment of (XIII) with diphenylphosphoryl azide followed by heating and reaction with an alcohol such as benzyl alcohol or tert-butanol; the corresponding ester is obtained and subsequently deprotected to the amine by hydrogenolysis (benzyl ester) or treatment with trifluoroacetic acid (tert-butyl ester). Such conditions are for example described in Journal of Organic Chemistry, 75(17), 5941-5952, 2010 or Tetrahedron: Asymmetry, 14(23), 3773-3778; 2003.

15) The acid of formula (XII) may derive from the ketone of formula (VII) after homologation of the ketone (VII) to an ester of formula (XII) followed by hydride reduction or hydrogenation of the double bond. Similar synthetic sequences from related substrates are described for example in Chemical & Pharmaceutical Bulletin, 52(6), 675-687; 2004, Synlett (2005), (10), 1559-1562, WO 2005019221, or WO 2010031735.

Scheme 5

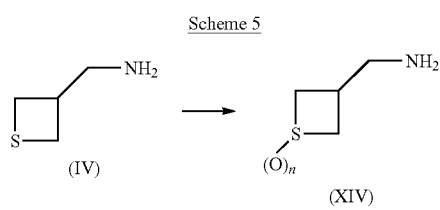

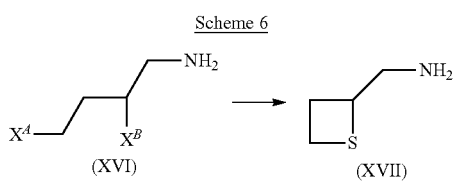

16) Amines of formula (IV) and (X) may be converted to further amine intermediates of formula (XIV) and (XV) wherein n is 1 or 2. The amines may be directly oxidized or first protected, oxidized and then deprotected.

Scheme 6

17) The amine of formula (XVII) may be obtained from a compound of formula (XVI) wherein $X^A$ and $X^B$ are independently hydroxy, halogen or a leaving group such as mesylate, tosylate or triflate. The sequence is then similar to that described for example in WO 2007080131 for the conversion of serinol to thietan-3-ylamine. Compounds of formula (XVI) are either known compounds or can be prepared by known methods to the person skilled in the art. Compounds of formula (XVII) may be oxidised as described in 16).

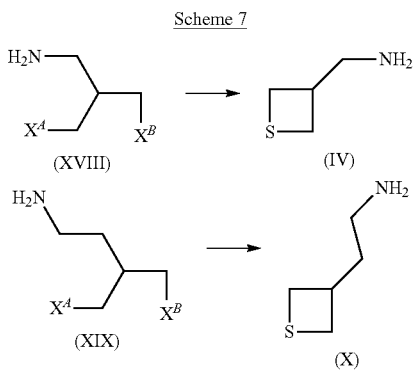

Scheme 7

18) Similarly, the amine of formula (IV) and (X) may be obtained from compounds of formula (XVIII) and (XIX) wherein $X^A$ and $X^B$ are independently hydroxy, halogen or a leaving group such as mesylate, tosylate or triflate. Compounds of formula (XVIII) and (XIX) are either known compounds or can be prepared by known methods to the person skilled in the art.

Protecting a crop of useful plants from insects, acarines, nematodes or molluscs, means e.g. controlling the population of insects, acarines, nematodes or molluscs in said crop of useful plants, e.g. such that the population of said insects, acarines, nematodes or molluscs is less than would be present in the absence of said compound, preferably significantly less, e.g. at least 5, 10, 15, 20, 25, 30, 35, 40, 45 50, 55, 60, 65, 70, 75, 80, 85, 90, 95 or even at least 99% less than in the absence of said compound.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies). The compounds of the invention may be used for example on turf, ornamentals, such as flowers, shrubs, broad-leaved trees or evergreens, for example conifers, as well as for tree injection, pest management and the like. Compositions comprising the compound of formula I may be used on ornamental garden plants (e.g. flowers, shrubs, broad-leaved trees or evergreens), e.g. to control aphids, whitefly, scales, meelybug, beetles and caterpillars. Compositions comprising the compound of formula I may be used on garden plants (e.g. flowers, shrubs, broad-leaved trees or evergreens), on indoor plants (e.g. flowers and shrubs) and on indoor pest e.g. to control aphids, whitefly, scales, meelybug, beetles and caterpillars.

Furthermore, the compounds of the invention may be effective against harmful insects, without substantially imposing any harmful side effects to cultivated plants. Application of the compounds of the invention may increase the harvest yields, and may improve the quality of the harvested material. The compounds of the invention may have favourable properties with respect to amount appled, residue formulation, selectivity, toxicity, production methodology, high activity, wide spectrum of control, safety, control of resistant organisms, e.g. pests that are resistant to organic phosphorus agents and/or carbamate agents.

Examples of pest species which may be controlled by the compounds of formula (I) include *coleopterans*, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis; lepidopterans*, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella; hemipterans*, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; *thysanopterans*, for example, *Thrips palmi, Franklinella occidental; orthopterans*, for example, *Blatella germanica, Periplaneta americana, Gryllotalpa Africana, Locusta migratoria migratoriodes; isopterans*, for example, *Reticulitermes speratus, Coptotermes formosanus; dipterans*, for example, *Musca domestica, Aedes aegypti, Hylemia platura, Culex pipiens, Anopheles sinensis, Culex tritaeniorhynchus, Liriomyza trifolii; acari*, for example, *Tetranychus cinnabarinus, Tetranychus urticae, Panonychus citri, Aculops pelekassi, Tarsonemus* spp.; nematodes, for example, *Meloidogyne incognita, Bursaphelenchus lignicolus Mamiya* et *Kiyohara, Aphelenchoides besseyi, Heterodera glycines, Pratylenchus* spp.

Examples of further pest species which may be controlled by the compounds of formula (I) include: from the order of the Anoplura (Phthiraptera), for example, *Damalinia* spp., *Haematopinus* spp., *Linognathus* spp., *Pediculus* spp., *Trichodectes* spp.; from the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*; from the class of the Bivalva, for example, *Dreissena* spp.; from the order of the Chilopoda, for example, *Geophilus* spp., *Scutigera* spp.; from the order of the Coleoptera, for example, *Acanthoscehdes obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.; from the order of the Collembola, for example, *Onychiurus armatus*; from the order of the Dermaptera, for example, *Forficula auricularia*; from the order of the Diplopoda, for example, *Blaniulus guttulatus*; from the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.; from the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*; ft may be furthermore possible to control protozoa, such as *Eimeria*; from the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.; from the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulaconthum solani, Bemisia* spp., *Brachycaudus helichrysii, Brachycolus* spp., *Brevicoryne brassicae, Calligypona manginata, Carneocephala fulgida, Ceratovacuna lanigena, Cercopidae, Cenoplastes* spp., *Chaetosiphon fragaefolii, Chionaspis tegalensis, Chlorita onukii, Chromaphis juglandicola, Chiysomphalus ficus, Cicadulina mbila, Coccomytilus halli, Coccus* spp., *Cryptomyzus ribis, Dalbulus* spp., *Dialeunodes* spp., *Diaphorina* spp., *Diaspis* spp., *Dorsalis* spp., *Drosicha* spp., *Dysaphis* spp., *Dysmicoccus* spp., *Empoasca* spp., *Eniosoma* spp., *Erythnoneuna* spp., *Euscelis bilobatus, Geococcus coffeae, Homalodisca coagulata, Hyaloptenus arundinis, Icerya* spp., *Idiocerus* spp., *Idioscopus* spp., *Laodelphax stniatellus, Lecanium* spp., *Lepidosaphes* spp., *Lipaphis erysimi, Macnosiphum* spp., *Mahanarva fimbniolata, Melanaphis sacchari, Metcalfiella* spp., *Metopolophium dinhodum, Monellia costalis, Monelliopsis pecanis, Myzus* spp., *Nasonovia ribisnigri, Nephotettix* spp., *Nilaparvata lugens, Oncometopia* spp., *Onthezia pnaelonga, Panabemisia mynicae, Paratrioza* spp., *Panlatonia* spp., *Pemphigus* spp., *Peregrinus maidis, Phenacoccus* spp., *Phloeomyzus passeninii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Ptenomalus* spp., *Pynilla* spp., *Quadnaspidiotus* spp., *Quesada gigas, Rastrococcus* spp., *Rhopalosiphum* spp., *Saissetia* spp., *Scaphoides titanus, Schizaphis graminum, Selenaspidus anticulatus, Sogata* spp., *Sogatella furcifera, Sogatodes* spp., *Stictocephala festina, Tenalaphana malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*; from the order of the Hymenoptera, for example, *Diprion* spp., *Hoplocampa* spp., *Lasius* spp., *Mono-morium pharaonic, Vespa* spp.; from the order of the Isopoda, for example, *Armadillidium vulgare, Oniscus asellus, Porcellio scaber*; from the order of the Isoptera, for example, *Reticulitermes* spp., *Odontotermes* spp.; from the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila*

*pseudospretella, Homona magnanima, Hyponomeuta padella, Laphygma* spp., *Lithocolletis blancardella, Lithophane antenna, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.; from the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*; from the order of the Siphonaptera, for example, *Ceratophyllus* spp., *Xenopsylla cheopis*. From the order of the Symphyla, for example, *Scutigerella immaculata*; from the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.; from the order of the Thysanura, for example, *Lepisma saccharina*. The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In particular, the compounds of the invention may be used to control the following pest species:

*Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (twospotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium* pharaonic (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compound of formula I may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables, cucurbits and pulses (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used for pest control on various plants, including soybean, corn, sugarcane, alfalfa, brassicas, oilseed rape (e.g. canola), potatoes (including sweet potatoes), cotton, rice, coffee, citrus, almonds, fruiting vegetables, cucurbits and pulses (e.g. tomatoes, pepper, chili, eggplant, cucumber, squash etc.), tea, bulb vegetables (e.g. onion, leek etc.), grapes, pome fruit (e.g. apples, pears etc.), stone fruit (e.g. pears, plums etc.), and cereals.

The compounds of the invention may be used on soybean to control, for example, *Elasmopalpus lignosellus, Diloboderus abderus, Diabrotica speciosa, Trialeurodes* spp., *Bemisia* spp., aphids, *Sternechus subsignatus, Formicidae, Agrotis ypsilon, Julus* spp., *Murgantia* spp., *Halyomorpha* spp., *Thyanta* spp., *Megascelis* ssp., *Procornitermes* ssp., *Gryllotalpidae, Nezara viridula, Piezodorus* spp., *Acrosternum* spp., *Neomegalotomus* spp., *Cerotoma trifurcata, Popillia japonica, Edessa* spp., *Liogenys fuscus*, stalk borer, *Scaptocoris castanea, phyllophaga* spp., *Migdolus* spp., *Pseudoplusia includens, Anticarsia gemmatalis, Epinotia* spp., *Rachiplusia* spp., *Spodoptera* spp. (e.g. *Spodoptera frugiperda*), *Bemisia tabaci, Tetranychus* spp., *Agriotes* spp., *Euschistus* spp. (e.g. *Euschistus heros*). The compounds of the invention are preferably used on soybean to control *Diloboderus abderus, Diabrotica speciosa, Trialeurodes* spp., *Bemisia* spp., *Nezara viridula, Piezodorus* spp., *Acrosternum* spp., *Cerotoma trifurcata, Popillia japonica, Euschistus heros, Scaptocoris castanea, phyllophaga* spp., *Migdolus* spp., *Agriotes* spp., *Euschistus* spp.

The compounds of the invention may be used on corn to control, for example, *Euschistus* spp. (e.g. *Euschistus heros*), *Dichelops furcatus, Diloboderus abderus, Thyanta* spp., *Elasmopalpus lignosellus, Halyomorpha* spp., *Spodoptera frugiperda, Nezara viridula, Cerotoma trifurcata, Popillia japonica, Agrotis ypsilon, Diabrotica speciosa*, aphids, *Heteroptera, Procornitermes* spp., *Scaptocoris castanea, Formicidae, Julus* ssp., *Dalbulus maidis, Diabrotica* spp. (e.g. *Diabrotica virgifera*), *Mocis latipes, Bemisia tabaci, heliothis* spp., *Tetranychus* spp., thrips spp., *phyllophaga* spp., *Migdolus* spp., *scaptocoris* spp., *Liogenys fuscus, Spodoptera* spp., *Ostrinia* spp., *Sesamia* spp., wireworms, *Agriotes* spp., *Halotydeus destructor*. The compounds of the invention are preferably used on corn to control *Euschistus* spp., (e.g. *Eus-*

*chistus heros*), *Dichelops furcatus*, *Diloboderus abderus*, *Nezara viridula*, *Cerotoma trifurcata*, *Popillia japonica*, *Diabrotica* spp. (e.g. *Diabrotica speciosa*, *Diabrotica virgifera*), *Tetranychus* spp., *Thrips* spp., *Phyllophaga* spp., *Migdolus* spp., *Scaptocoris* spp., *Agriotes* spp.

The compounds of the invention may be used on sugar cane to control, for example, *Sphenophorus* spp., termites, *Migdolus* spp., *Diloboderus* spp., *Telchin licus*, *Diatrea saccharalis*, *Mahanarva* spp., Mealybugs, *Chilo* spp.

The compounds of the invention may be used on alfalfa to control, for example, *Hypera brunneipennis*, *Hypera postica*, *Colias eurytheme*, *Collops* spp., *Empoasca solana*, *Epitrix* spp., *Geocoris* spp., *Lygus hesperus*, *Lygus lineolaris*, *Spissistilus* spp., *Spodoptera* spp., Aphids, *Trichoplusia ni*. The compounds of the invention are preferably used on alfalfa to control *Hypera brunneipennis*, *Hypera postica*, *Empoasca solana*, *Epitrix* spp., *Lygus hesperus*, *Lygus lineolaris*, *Trichoplusia ni*.

The compounds of the invention may be used on brassicas to control, for example, *Chrysodeixis* spp., *Plutella xylostella*, *Pieris* spp. (e.g. *Pieris brassicae*, *Pieris rapae*, *Pieris napi*), *Mamestra* spp. (e.g. *Mamestra brassicae*), *Plusia* spp., *Trichoplusia* spp. (e.g. *Trichoplusia ni*), *Phyllotreta* spp. (e.g. *Phyllotreta cruciferae*, *Phyllotreta striolata*), *Spodoptera* spp., *Empoasca* spp., *thrips* spp., *Delia* spp., *Murgantia* spp., *Trialeurodes* spp., *Bemisia* spp., *Microtheca* spp., Aphids, *Chaetocnema* spp., *Psylliodes* spp. (e.g. *Psylliodes chrysocephala*). The compounds of the invention are preferably used on brassicas to control *Plutella xylostella*, *Pieris* spp., *Plusia* spp., *Trichoplusia ni*, *Phyllotreta* spp., *Thrips* spp., *Chaetocnema* spp.

The compounds of the invention may be used on oil seed rape, e.g. canola, to control, for example, *Meligethes* spp. (e.g. *Meligethes aeneus*), *Ceutorhynchus* spp., (e.g. *Ceutorhynchus assimilis*, *Ceutorhynchus napi*), *Halotydeus destructor*, *Psylloides* spp. (e.g. *Psylliodes chrysocephala*), *Phyllotreta* spp. (e.g. *Phyllotreta cruciferae*, *Phyllotreta striolata*), *Chaetocnema* spp.

The compounds of the invention may be used on potatoes, including sweet potatoes, to control, for example, *Empoasca* spp., *Leptinotarsa* spp., *Diabrotica speciosa*, *Phthorimaea* spp., *Paratrioza* spp., *Maladera matrida*, *Agriotes* spp., Aphids, wireworms. The compounds of the invention are preferably used on potatoes, including sweet potatoes, to control *Empoasca* spp., *Leptinotarsa* spp., *Diabrotica speciosa*, *Phthorimaea* spp., *Paratrioza* spp., *Agriotes* spp.

The compounds of the invention may be used on cotton to control, for example, *Anthonomus grandis*, *Pectinophora* spp., *heliothis* spp., *Spodoptera* spp., *Tetranychus* spp. (e.g. *Tetranychus urticae*), *Empoasca* spp., *Thrips* spp. (e.g. *Thrips tabaci*, *Thrips palmi*), *Bemisia tabaci*, *Trialeurodes* spp., Aphids, *Lygus* spp. (e.g. *Lygus lineolaris*, *Lygus Hesperus*), *phyllophaga* spp., *Scaptocoris* spp., *Austroasca viridigrisea*, *Creontiades* spp., *Nezara* spp., *Piezodorus* spp., *Halotydeus destructor*, *Oxycaraenus hyalinipennis*, *Dysdercus cingulatus*, *Amrasca* spp. (e.g. *Amrasca biguttula biguttula*), *Frankliniella* spp. (e.g. *Frankliniella schultzei*), *Scirtothrips* spp. (e.g. *Scirtothrips dorsali*), *Anaphothrips* spp., *Polyphagotarsonemus latus*. The compounds of the invention are preferably used on cotton to control *Anthonomus grandis*, *Tetranychus* spp., *Empoasca* spp., *thrips* spp., *Lygus* spp., *phyllophaga* spp., *Scaptocoris* spp.

The compounds of the invention may be used on rice to control, for example, *Leptocorisa* spp. (e.g. *Leptocorisa oratorius*, *Leptocorisa chinensis*, *Leptocorisa acuta*), *Cnaphalocrosis* spp., *Chilo* spp. (e.g. *Chilo suppressalis*, *Chilo polychrysus*, *Chilo auricilius*), *Scirpophaga* spp. (e.g. *Scirpophaga incertulas*, *Scirpophaga innotata*, *Scirpophaga nivella*), *Lissorhoptrus* spp., *Oebalus pugnax*, *Scotinophara* spp. (e.g. *Scotinophara coarctata*, *Scotinophara lurida*, *Scotinophara latiuscula*), *Nephotettix* spp. (e.g. *Nephotettix malayanus*, *Nephotettix nigropictus*, *Nephotettix parvus*, *Nephottetix virescens*, *Nephotettix cincticeps*), Mealybugs, *Sogatella furcifera*, *Nilaparvata lugens*, *Orseolia* spp. (e.g. *Orseolia oryzae*), *Cnaphalocrocis medinalis*, *Marasmia* spp. (e.g. *Marasmia patnalis*, *Marasmia exigua*), *Stenchaetothrips biformis*, *Thrips* spp., *Hydrellia* spp. (e.g. *Hydrellia philippina*), Grasshoppers, *Pomacea canaliculata*, *Scirpophaga innotata*, *Sesamia inferens*, *Laodelphax striatellus*, *Nymphula depunctalis*, *Oulema oryzae*, Stinkbugs. The compounds of the invention are preferably used on rice to control *Leptocorisa* spp., *Lissorhoptrus* spp., *Oebalus pugnax*, *Nephotettix* spp. (e.g. *Nephotettix malayanus*, *Nephotettix nigropictus*, *Nephotettix parvus*, *Nephottetix virescens*, *Nephotettix cincticeps*), *Sogatella furcifera*, *Stenchaetothrips biformis*, *Thrips* spp., *Hydrellia* spp. (e.g. *Hydrellia philippina*), Grasshoppers, *Pomacea canaliculata*, *Scirpophaga innotata*, *Chilo* spp., *Oulema oryzae*.

The compounds of the invention may be used on coffee to control, for example, *Hypothenemus* spp. (e.g. *Hypothenemus Hampei*), *Perileucoptera Coffeella*, *Tetranychus* spp., *Brevipalpus* spp., Mealybugs. The compounds of the invention are preferably used on coffee to control *Hypothenemus Hampei*, *Perileucoptera Coffeella*.

The compounds of the invention may be used on citrus to control, for example, *Panonychus citri*, *Phyllocoptruta oleivora*, *Brevipalpus* spp. (e.g. *Brevipalpus californicus*, *Brevipalpus phoenicis*), *Diaphorina citri*, *Scirtothrips* spp. (e.g. *Scirtothrips dorsalis*), *Thrips* spp., *Unaspis* spp., *Ceratitis capitata*, *Phyllocnistis* spp. (e.g. *Phyllocnistis citrella*), Aphids, Hardscales, Softscales, Mealybugs. The compounds of the invention are preferably used on citrus to control *Panonychus citri*, *Phyllocoptruta oleivora*, *Brevipalpus* spp., *Diaphorina citri*, *Scirtothrips* spp., *thrips* spp., *Phyllocnistis* spp.

The compounds of the invention may be used on almonds to control, for example, *Amyelois transitella*, *Tetranychus* spp.

The compounds of the invention may be used on fruiting vegetables, cucurbits and pulses, including tomatoes, pepper, chili, eggplant, cucumber, squash etc., to control, for example, *Thrips* spp., *Tetranychus* spp. (e.g. *Tetranychus urticae*), *Polyphagotarsonemus* spp. (e.g. *Polyphagotarsonemus latus*), *Aculops* spp. (e.g. *Aculops lycopersici*), *Empoasca* spp. (e.g. *Empoasca fabae*), *Spodoptera* spp., *heliothis* spp., *Tuta absoluta*, *Liriomyza* spp. (e.g. *Liriomyza brassicae*, *Liriomyza bryoniae*, *Liriomyza huidobrensis*, *Liriomyza sativae*, *Liriomyza trifolii*), *Bemisia tabaci*, *Trialeurodes* spp., Aphids, *Paratrioza* spp., *Frankliniella* spp. (e.g. *Frankliniella occidentalis*, *Frankliniella intonsa*, *Frankliniella bispinosa*), *Spodoptera* spp. (e.g. *Spodoptera exigua*, *Spodoptera littoralis*, *Spodoptera litura*, *Spodoptera frugtperda*, *Spodoptera eridania*), *Anthonomus* spp., *Phyllotreta* spp., *Amrasca* spp. (e.g. *Amrasca biguttula biguttula*), *Epilachna* spp., *Halyomorpha* spp., *Scirtothrips* spp., *Leucinodes* spp. (e.g. *Leucinodes orbonalis*), *Neoleucinodes* spp. (e.g. *Neoleucinodes elegantalis*), *Maruca* spp., Fruit flies, Stinkbugs, Lepidopteras, Coleopteras, *Helicoverpa* spp. (e.g. *Helicoverpa armigera*), *Heliothis* spp. (e.g. *Heliothis virescens*), *Paratrioza* spp. (e.g. *Paratrioza cockerelli*), The compounds of the invention are preferably used on fruiting vegetables, cucurbits and pulses, including tomatoes, pepper, chili, eggplant, cucumber, squash etc., to control *Thrips* spp., *Tetranychus* spp., *Polyphagotarsonemus* spp., *Aculops* spp.,

*Empoasca* spp., *Spodoptera* spp., *heliothis* spp., *Tuta absoluta, Liriomyza* spp., *Paratrioza* spp., *Frankliniella occidentalis, Frankliniella* spp., *Amrasca* spp., *Scirtothrips* spp., *Leucinodes* spp., *Neoleucinodes* spp.

The compounds of the invention may be used on tea to control, for example, *Pseudaulacaspis* spp., *Empoasca* spp., *Scirtothrips* spp., *Caloptilia theivora, Tetranychus* spp. The compounds of the invention are preferably used on tea to control *Empoasca* spp., *Scirtothrips* spp.

The compounds of the invention may be used on bulb vegetables, including onion, leek etc. to control, for example, *Thrips* spp., *Spodoptera* spp., *heliothis* spp. The compounds of the invention are preferably used on bulb vegetables, including onion, leek etc. to control *Thrips* spp.

The compounds of the invention may be used on grapes to control, for example, *Empoasca* spp., *Lobesia* spp., *Eupoecilia ambiguella, Frankliniella* spp., *Thrips* spp., *Tetranychus* spp., *Rhipiphorothrips Cruentatus, Eotetranychus Willamettei, Erythroneura Elegantula, Scaphoides* spp., *Scelodonta strigicollis*, Mealybugs. The compounds of the invention are preferably used on grapes to control *Frankliniella* spp., *Thrips* spp., *Tetranychus* spp., *Rhipiphorothrips Cruentatus, Scaphoides* spp.

The compounds of the invention may be used on pome fruit, including apples, pears etc., to control, for example, *Cacopsylla* spp., *Psylla* spp., *Panonychus ulmi, Cydia pomonella, Lepidopteras*, Aphids, Hardscales, Softscales. The compounds of the invention are preferably used on pome fruit, including apples, pears etc., to control *Cacopsylla* spp., *Psylla* spp., *Panonychus ulmi.*

The compounds of the invention may be used on stone fruit to control, for example, *Grapholita molesta, Scirtothrips* spp., *Thrips* spp., *Frankliniella* spp., *Tetranychus* spp., Aphids, Hardscales, Softscales, Mealybugs. The compounds of the invention are preferably used on stone fruit to control *Scirtothrips* spp., *Thrips* spp., *Frankliniella* spp., *Tetranychus* spp.

The compounds of the invention may be used on cereals to control, for example, Aphids, Stinkbugs, earthmites, *Eurygaster integriceps, Zabrus tenebrioides, Anisoplia austriaca, Chaetocnema aridula, Phyllotreta* spp., *Oulema melanopus, Oscinella* spp., *Delia* spp., *Mayetiola* spp., *Contarinia* spp., *Cephus* spp., *Steneotarsonemus* spp., *Apamea* spp.

In another embodiment compounds of formula I may be used on rice to control *Baliothrips biformis* (*Thrips*), *Chilo* spp. (e.g. *Chilo polychrysus* (Dark headed striped borer), *Chilo suppressalis* (Rice stemborer), *Chilo indicus* (Paddy stem borer), *Chilo polychrysus* (Dark-headed rice borer), *Chilo suppressalis* (Stripe stem borer)), *Cnaphalocrocis medinalis* (Rice leaf folder), *Dicladispa armigera* (Hispa), *Hydrellia philipina* (Rice whorl-maggot), *Laodelphax* spp. (Smaller brown planthopper) (e.g. *Laodelphax striatellus*), *Lema oryzae* (Rice leafbeetle), *Leptocorsia acuta* (Rice bug), *Leptocorsia oratorius* (rice bug), *Lissorhoptrus oryzophilus* (rice water weevil), *Mythemina separata* (armyworm), *Nephottetix* spp. (Green leafhopper) (e.g. *Nephotettix cincticeps, Nephotettix malayanus, Nephotettix nigropictus, Nephottetix parvus, Nephottetix virescens*), *Nilaparvata lugens* (Brown Planthopper), *Nymphula depunctalis* (Rice caseworm), *Orseolia oryzae* (Rice Gall midge), *Oulema oryzae* (Rice leafbeetle), *Scirpophaga incertulas* (Yellow Stemborer), *Scirpophaga innotata* (White Stemborer), *Scotinophara coarctata* (Rice black bug), *Sogaella frucifera* (White-backed planthopper), *Steneotarsonemus spinki.*

The compounds of the invention may be used to control animal housing pests including. Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leafminers (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, *Thrips*, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The compounds of formula (I), in particular those in the tables above, may be used for soil applications, including as a seed application, to target at least the following: sucking pests such as aphids, *thrips*, brown plant hopper (e.g. on rice), sting bugs, white flies (e.g. on cotton and vegetables), mites; on soil pests such as corn root worm, wireworms, white grubs, *zabrus*, termites (e.g. on sugar cane, soy, pasture), maggots, cabbage root fly, red legged earth mite; on lepidoptera, such as *spodoptera*, cutworms, *elasmoplpus, plutella* (e.g. *brassica*), stem borers, leaf miners, flea beetle, *Sternechus*; on nematicides, such as *Heterodera glycines* (e.g. on soybean), *Pratylenchus brachyurus* (e.g. on corn), *P. zeae* (e.g. oncorn), *P. penetrans* (e.g. on corn), *Meloidogyne incognita* (e.g. on vegetables), *Heterodera schachtii* (e.g. on sugar beet), *Rotylenchus reniformis* (e.g. on cotton), *Heterodera avenae* (e.g. on cereals), *Pratylenchus neglectus* (e.g. on cereals), *thornei* (e.g. on cereals).

The compounds of formula (I), in particular those in the tables above may be used for seed applications at least on the following: soil grubs for corn, soybeans, sugarcane: *Migdolus* spp; *Phyllophaga* spp.; *Diloboderus* spp; *Cyclocephala* spp; *Lyogenys fuscus*; sugarcane weevils: *Sphenophorus levis* & *Metamasius hemipterus*; termites for soybeans, sugarcane, pasture, others: *Heterotermes tenuis; Heterotermes longiceps; Cornitermes cumulans; Procornitermes triacifer; Neocapritermes opacus; Neocapritermes parvus*; corn root worms for corn and potatoes: *Diabrotica* spp., seed Maggot: *Delia platura*; soil stinkbugs: *Scaptocoris castanea*; wireworms: *Agriotes* spp; *Athous* spp *Hipnodes bicolor; Ctenicera destructor; Limonius canu; Limonius californicus*; rice water weevil: *Lissorhoptrus oryzophilus*; Red Legged earth mites: *Halotydeus destructor.*

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

The compounds of the invention may be applied to plant parts. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Compounds of formula I may be used on transgenic plants (including cultivars) obtained by genetic engineering methods and/or by conventional methods. These are understood as meaning plants having novel properties ("traits") which have been obtained by conventional breeding, by mutagenesis or by recombinant DNA techniques. Depending on the plant species or plant cultivars, their location and growth conditions (soils, climate, vegetation period, diet), the treatment according to the invention may also result in superadditive "synergistic") effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes).

Compounds of formula I may be used on transgenic plants that are capable of producing one or more pesticidal proteins which confer upon the transgenic plant tolerance or resistance to harmful pests, e.g. insect pests, nematode pests and the like. Such pesticidal proteins include, without limitation, Cry proteins from *Bacillus thuringiensis* Cry1Ab, Cry1Ac, Cry1F, Cry2Ab, Cry2Ae, Cry3A, Cry3Bb, or Cry9C; engineered proteins such as modified Cry3A (U.S. Pat. No. 7,030, 295) or Cry1A.105; or vegetative insecticidal proteins such as Vip1, Vip2 or Vip3. A full list of Bt Cry proteins and VIPs useful in the invention can be found on the worldwide web at *Bacillus thuringiensis* Toxin Nomenclature Database maintained by the University of Sussex (see also, Crickmore et al. (1998) *Microbiol. Mol. Biol. Rev.* 62:807-813). Other pesticidal proteins useful in the invention include proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. Further examples of such pesticidal proteins or transgenic plants capable of synthesizing such proteins are disclosed, e.g., in EP-A 374753, WO 93/007278, WO 95/34656, EP-A 427529, EP-A 451878, WO 03/18810 and WO 03/52073. The methods for producing such transgenic plants are generally known to the person skilled in the art and some of which are commercially available such as Agrisure®CB (corn producing Cry1Ab), Agrisure®RW (corn producing mCry3A), Agrisure® Viptera (corn hybrids producing Vip3Aa); Agrisure300GT (corn hybrids producing Cry1Ab and mCry3A); YieldGard® (corn hybrids producing the Cry1Ab protein), YieldGard® Plus (corn hybrids producing Cry1Ab and Cry3Bb1), Genuity® SmartStax® (corn hybrids with Cry1A.105, Cry2Ab2, Cry1F, Cry34/35, Cry3Bb); Herculex® I (corn hybrids producing Cry1Fa) and Herculex®RW (corn hybrids producing Cry34Ab1, Cry35Ab1 and the enzyme Phosphinothricin-N-Acetyltransferase [PAT]); NuCOTN®33B (cotton cultivars producing Cry1Ac), Bollgard®I (cotton cultivars producing Cry1Ac), Bollgard®II (cotton cultivars producing Cry1Ac and Cry2Ab2) and VIPCOT® (cotton cultivars producing a Vip3Aa). Soybean Cyst Nematode resistance soybean (SCN®—Syngenta) and soybean with Aphid resistant trait (AMT®) are also of interest.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1A(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1A(b) toxin. Bt176 maize also transgenically expresses the enzyme PAT to achieve tolerance to the herbicide glufosinate ammonium.

3. MIR604Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1A(b) toxin obtained from *Bacillus thuringiensis* subsp. *kurstaki* which brings about tolerance to certain Lepidoptera, include the European corn borer.

Further examples of transgenic plants, and of very high interest, are those carrying traits conferring resistance to 2.4D (e.g. Enlist®) (e.g. WO 2011066384), glyphosate (e.g. Roundup Ready®, Roundup Ready 2 Yield®), sulfonylurea (e.g. STS®), glufosinate (e.g. Liberty Link®, Ignite®), Dicamba (Monsanto), HPPD tolerance (e.g. isoxaflutole herbicide) (Bayer CropScience, Syngenta). Double or triple stacks of any of the traits described here are also of interest, including glyphosate and sulfonyl-urea tolerance ((e.g. Optimum GAT®), plants stacked with STS® and Roundup Ready® or plants stacked with STS® and Roundup Ready 2 Yield®), dicamba and glyphosate tolerance (Monsanto). Of particular interest are soybean plants carrying trains conferring resistance to 2.4D (e.g. Enlist®), glyphosate (e.g. Roundup Ready®, Roundup Ready 2 Yield®), sulfonylurea (e.g. STS®), glufosinate (e.g. Liberty Link®, Ignite®), Dicamba (Monsanto) HPPD tolerance (e.g. isoxaflutole herbicide) (Bayer CropScience, Syngenta). Double or triple stack in soybean plants of any of the traits described here are also of interest, including glyphosate and sulfonyl-urea tolerance (e.g. Optimum GAT®, plants stacked with STS® and Roundup Ready® or Roundup Ready 2 Yield®), dicamba and glyphosate tolerance (Monsanto).

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

Examples of cotton transgenic events include MON 531/757/1076 (Bollgard I®-Monsanto), MON1445 (Roundup ready Cotton®—Monsanto), MON531×MON1445 (Bollgard I+RR®—Monsanto), MON15985 (Genuity Bollgard II Cotton®—Monsanto), MON88913 (Genuity RR FLEX Cotton®—Monsanto), MON15985×MON1445 (Genuity Bollgard II+RR FELX cotton 35®—Monsanto), MON15983× MON88913 (Genuity Bollgard II+RR FLEX Cotton®— Monsanto), MON15985 (FibreMax Bollgard II Cotton®— Monsanto), LL25 (FibreMax LL Cotton®—BCS Stoneville), GHB614 (FibreMax GlyTol Cotton®—BCS Stoneville), LL25×MON15985 (FibreMax LL Bollgard II Cotton®—BCS Stoneville/Monsanto), GHB614×LL25 (FibreMax LL GlyTol Cotton®—BCS Stoneville), GHB614× LL25×MON15985 (FibreMax RR GlyTol Bollgard II Cotton®—BCS Stoneville), MON88913×MON15985 (FibreMax LL GlyTol Bollgard II Cotton®—Monsanto), MON88913 (FibreMax RR Flex Cotton®—Monsanto), GHB119+T304-40 (Twinlink®—BCS Stoneville), GHB119+T304-40×LL25×GHB614 (Twinlink LL GT®— BCS Stoneville), 3006-210-23×281-24-236 (PhytoGen Widestrike Insect Protection®—Dow), 3006-210-23×281-24-236×MON88913 (PhytoGen Widestrike Insect Protection+RR FLEX—®—Dow/Monsanto), 3006-210-23×281-24-236×MON1445 ((PhytoGen Widestrike Insect Protection+RR®—Dow/Monsanto), MON1445 (PhytoGen Roundup Ready®—Monsanto), MON88913 (PhytoGen Roundup Ready FLEX®—Monsanto), COT102×COT67B (Vipcot®—Syngenta), COT102×COT67B×MON88913 (Vipcot RR FLEX®—Syngenta/Monsanto), 281-24-236 (Dow), 3006-210-23 (Dow), COT102 (Syngenta), COT67B (Syngenta), T304-40 (BCS Stoneville).

Examples of Soy transgenic events include MON87701× MON89788 (Genuity Roundup ready 2 Yield Soybeans®— Monsanto), MON89788 (Roundup Ready2Yield®, RR2Y®—Monsanto), MON87708 (Monsanto), 40-3-2 (Roundup Ready®, RR1®—Monsanto), MON87701 (Monsanto), DAS-68416 (Enlist Weed Control System®—Dow), DP356043 (Optimum GAT®—Pioneer), A5547-127 (LibertyLink Soybean®—Bayercropscience), A2704-12 (Bayercropscience), GU262 (Bayercropscience), W62 W98 (Bayercropscience), CRV127 (Cultivance®—BASF/EMBRAPA) SYHT0H2 (WO2012/082548).

Examples of Maize transgenic events include T25 (LibertyLink®, LL®—Bayerscropscience),
DHT-1 (Dow), TC1507 (Herculex I®—Dow), DAS59122-7 (Herculex RW®—Dow), TC1507+DAS59122-7—Herculex Xtra®—Dow), TC1507×DAS-59122-7×NK603 (Herculex Xtra+RR®—Dow), TC1507×DAS-59122-×MON88017×MON89034 (Genuity Smartstax Corn®, Genuity Smartstax RIB Complete®—Monsanto/Dow), MON89034×NK603 (Genuity VT double PRO®—Monsanto), MON89034+MON88017 (Genuity VT Triple PRO®—Monsanto), NK603 (Roundup Ready 2®, RR2®—Monsanto), MON810 (YieldGard BT®, Yieldgard Cornborer®—Monsanto), MON810×NK603 (YieldGard cornborer RR Corn 2®—Monasnto), MON810×MON863 (YieldGard Plus®—Monsanto), MON863×MON810×NK603 (YieldGard Plus+RR Corn2®/YieldGard RR Maize®—Monsanto), MON863×NK603 (YieldGard Rotworm+RR Corn 2®—Monsanto), MON863 (YieldBard RW®—Monsanto), MON89034 (YieldGard RW®—Monsanto), MON88017 (YieldGard VT RW®—Monsanto), MON810+MON88017 (YieldGard VT Triple®—Monsanto), MON88017+MON89034 (YieldGard VT Triple Pro®—Monsanto), Bt11+MIR604+GA21 (Agrisure 3000®—Syngenta), Bt11+TC1507+MIR604+5307+GA21 (Syngenta), Bt11+TC1507+MIR604+DAS59122+GA21 (Agrisure 3122®—Syngenta), BT11 (Agrisure CB®—Syngenta), GA21—(Agrisure GT®—Syngenta), MIR604 (Agrisure RW®—Syngenta), Bt11+MIR162 (Agrisure TL VIP®—Syngenta), BT11+MIR162+GA21 (Agrisure Viptra 31100—Syngenta), BT11+MIR162+MIR604 (Agrisure TM 3100®—Syngenta), Event3272+BT11+MIR604+GA21 (Syngenta), BT11+MIR1692+MIR604+GA21 (Agrisure Viptera 3111®—Syngenta), BT11+MIR 162+TC1507+GA21 (Agrisure Viptera 3220®—Syngenta), BT11+MIR162+TC1507+MIR604+5307+GA21 (Agrisure Viptera 3222®—Syngenta), MIR162 (Syngenta), BT11+GA21+MIR162+MIR604+5307 (Syngenta), 5307 (Syngenta).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_5$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following (where "Tx" means a compound of formula (I), and in particular a compound selected from Tables 1P to 90P and 1Q to 36Q, which may result in a synergistic combination with the given active ingredient):

a) Pyrethroids, such as permethrin+Tx, cypermethrin+Tx, fenvalerate+Tx, esfenvalerate+Tx, deltamethrin+Tx, cyhalothrin+Tx (in particular lambda-cyhalothrin+Tx and gamma cyhalothrin+Tx), bifenthrin+Tx, fenpropathrin+Tx, cyfluthrin+Tx, tefluthrin+Tx, fish safe pyrethroids+Tx (for example ethofenprox+Tx), natural pyrethrin+Tx, tetramethrin+Tx, S-bioallethrin+Tx, fenfluthrin+Tx, prallethrin+Tx, acrinathirin+Tx, etofenprox+Tx or 5-benzyl-3-furylmethyl-(E)-(1R,3S)-2,2-dimethyl-3-(2-oxothiolan-3-ylidenemethyl)cyclopropane carboxylate+Tx;

b) Organophosphates, such as profenofos+Tx, sulprofos+Tx, acephate+Tx, methyl parathion+Tx, azinphos-methyl+Tx, demeton-s-methy+Tx 1, heptenophos+Tx, thiometon+Tx, fenamiphos+Tx, monocrotophos+Tx, profenofos+Tx, triazophos+Tx, methamidophos+Tx, dimethoate+Tx, phosphamidon+Tx, malathion+Tx, chlorpyrifos+Tx, phosalone+Tx, terbufos+Tx, fensulfothion+Tx, fonofos+Tx, phorate+Tx, phoxim+Tx, pirimiphos-methyl+Tx, pirimiphos-ethyl+Tx, fenitrothion+Tx, fosthiazate+Tx or diazinon+Tx;

c) Carbamates (including aryl carbamates), such as pirimicarb+Tx, triazamate+Tx, cloethocarb+Tx, carbofuran+Tx, furathiocarb+Tx, ethiofencarb+Tx, aldicarb+Tx, thiofurox+Tx, carbosulfan+Tx, bendiocarb+Tx, fenobucarb+Tx, propoxur+Tx, methomyl+Tx or oxamyl+Tx;

d) Benzoyl ureas, such as diflubenzuron+Tx, triflumuron+Tx, hexaflumuron+Tx, flufenoxuron+Tx, diafenthiuron+Tx, lufeneron+Tx, novaluron+Tx, noviflumuron+Tx or chlorfluazuron+Tx;

e) Organic tin compounds, such as cyhexatin+Tx, fenbutatin oxide+Tx or azocyclotin+Tx;

f) Pyrazoles, such as tebufenpyrad+Tx, tolfenpyrad+Tx, ethiprole+Tx, pyriprole+Tx, fipronil+Tx, and fenpyroximate+Tx;

g) Macrolides, such as avermectins or milbemycins, for example abamectin+Tx, emamectin benzoate+Tx, ivermectin+Tx, milbemycin+Tx, spinosad+Tx, azadirachtin+Tx, milbemectin+Tx, lepimectin+Tx or spinetoram+Tx;

h) Hormones+Tx or pheromones+Tx;

i) Organochlorine compounds, such as endosulfan+Tx (in particular alpha-endosulfan+Tx), benzene hexachloride+Tx, DDT+Tx, chlordane+Tx or dieldrin+Tx;

j) Amidines, such as chlordimeform+Tx or amitraz+Tx;

k) Fumigant agents, such as chloropicrin+Tx, dichloropropane+Tx, methyl bromide+Tx or metam+Tx;

l) Neonicotinoid compounds, such as imidacloprid+Tx, thiacloprid+Tx, acetamiprid+Tx, nitenpyram+Tx, dinotefuran+Tx, thiamethoxam+Tx, clothianidin+Tx, or nithiazine+Tx;

m) Diacylhydrazines+Tx, such as tebufenozide+Tx, chromafenozide+Tx or methoxyfenozide+Tx;

n) Diphenyl ethers, such as diofenolan+Tx or pyriproxifen+Tx;

o) Pyrazolines such as Indoxacarb+Tx or metaflumizone+Tx;

p) Ketoenols, such as Spirotetramat+Tx, spirodiclofen+Tx or spiromesifen+Tx;

q) Diamides, such as flubendiamide+Tx, chlorantraniliprole+Tx (Rynaxypyr®) or cyantraniliprole+Tx;

r) Essential oils such as Bugoil®—(PlantImpact); or s) a compound selected from buprofezine+Tx, flonicamid+Tx, acequinocy+Tx 1, bifenazate+Tx, cyenopyrafen+Tx, cyflumetofen+Tx, etoxazole+Tx, flometoquin+Tx, fluacrypyrim+Tx, fluensulfone+Tx, flufenerim+Tx, flupyradifuone+Tx, harpin+Tx, iodomethane+Tx, dodecadienol+Tx, pyridaben+Tx, pyridalyl+Tx, pyrimidifen+Tx, flupyradifurone+Tx, 4-[(6-Chloro-pyridin-3-ylmethyl)-(2,2-difluoroethyl)-amino]-5H-furan-2-one (DE 102006015467), CAS: 915972-17-7+Tx (WO 2006129714; WO2011/147953; WO2011/147952), CAS: 26914-55-8 (WO 2007020986), chlorfenapyr+Tx, pymetrozine+Tx, sulfoxaflor+Tx and pyrifluqinazon+Tx.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap+Tx) or hopper specific insecticides (combinations such as buprofezin+Tx) for use in rice may be employed. Alternatively insecticides or acaricides specific for particular insect species/stages may also be included in the compositions (for example acaricidal ovolarvicides, to give combinations such as clofentezine+Tx, flubenzimine+Tx, hexythiazox+Tx or tetradifon+Tx; acaricidal motilicides, to give combinations such as dicofol+Tx or propargite+Tx; acaricides, to give combinations such as bromopropylate+Tx or chlorobenzilate+Tx; or growth regulators, such as hydramethylnon+Tx, cyromazine+Tx, methoprene+Tx, chlorfluazuron+Tx or diflubenzuron+Tx).

Examples of fungicidal compounds and combinations which may be included in the composition of the invention are (E)-N-methyl-2-[2-(2,5-dimethylphenoxymethyl)phenyl]-2-methoxy-iminoacetamide (SSF-129)+Tx, 4-bromo-2-cyano-N,N-dimethyl-6-trifluoromethyl-benzimidazole-1-sulfonamide+Tx, α-[N-(3-chloro-2,6-xylyl)-2-methoxyacetamido]-γ-butyrolactone+Tx, 4-chloro-2-cyano-N,N-dimethyl-5-p-tolylimidazole-1-sulfonamide (IKF-916, cyamidazosulfamid)+Tx, 3-5-dichloro-N-(3-chloro-1-ethyl-1-methyl-2-oxopropyl)-4-methylbenzamide (RH-7281, zoxamide)+Tx, N-allyl-4,5,-dimethyl-2-trimethylsilylthiophene-3-carboxamide (MON65500)+Tx, N-(1-cyano-1,2-dimethylpropyl)-2-(2,4-dichlorophenoxy)-propionamide (AC382042)+Tx, N-(2-methoxy-5-pyridyl)-cyclopropane carboxamide+Tx, acibenzolar (CGA245704) (e.g. acibenzolar-5-methyl)+Tx, alanycarb+Tx, aldimorph+Tx, anilazine+Tx, azaconazole+Tx, azoxystrobin+Tx, benalaxyl+Tx, benomyl+Tx, benthiavalicarb+Tx, biloxazol+Tx, bitertanol+Tx, bixafen+Tx, blasticidin S+Tx, boscalid+Tx, bromuconazole+Tx, bupirimate+Tx, captafol+Tx, captan+Tx, carbendazim+Tx, carbendazim+Tx, chlorhydrate+Tx, carboxin+Tx, carpropamid+Tx, carvone+Tx, CGA41396+Tx, CGA41397+Tx, chinomethionate+Tx, chlorothalonil+Tx, chlorozolinate+Tx, clozylacon+Tx, copper containing compounds to give combinations such as copper oxychloride+Tx, copper oxyquinolate+Tx, copper sulfate+Tx, copper tallate+Tx and Bordeaux mixture+Tx, cyclufenamid+Tx, cymoxanil+Tx, cyproconazole+Tx, cyprodinil+Tx, debacarb+Tx, di-2-pyridyl disulfide 1,1'-dioxide+Tx, dichlofluanid+Tx, diclomezine+Tx, dicloran+Tx, diethofencarb+Tx, difenoconazole+Tx, difenzoquat+Tx, diflumetorim+Tx, O,O-di-iso-propyl-5-benzyl thiophosphate+Tx, dimefluazole+Tx, dimetconazole+Tx, dimethomorph+Tx, dimethirimol+Tx, diniconazole+Tx, dinocap+Tx, dithianon+Tx, dodecyl dimethyl ammonium chloride+Tx, dodemorph+Tx, dodine+Tx, doguadine+Tx, edifenphos+Tx, epoxiconazole+Tx, ethirimo+Tx 1, ethyl-(Z)—N-benzyl-N-([methyl(methyl-thioethylideneamino-oxycarbonyl)amino]thio)-β-alaninate+Tx, etridiazole+Tx, famoxadone+Tx, fenamidone (RPA407213)+Tx, fenarimol+Tx, fenbuconazole+Tx, fenfuram+Tx, fenhexamid (KBR2738)+Tx, fenpiclonil+Tx, fenpropidin+Tx, fenpropimorph+Tx, fentin acetate+Tx, fentin hydroxide+Tx, ferbam+Tx, ferimzone+Tx, fluazinam+Tx, fludioxonil+Tx, flumetover+Tx, fluopyram+Tx, fluoxastrobin+Tx, fluoroimide+Tx, fluquinconazole+Tx, flusilazole+Tx, flutolanil+Tx, flutriafol+Tx, fluxapyroxad+Tx, folpet+Tx, fuberidazole+Tx, furalaxyl+Tx, furametpyr+Tx, guazatine, +Tx hexaconazole+Tx, hydroxyisoxazole+Tx, hymexazole+Tx, imazalil+Tx, imibenconazole+Tx, iminoctadine+Tx, iminoctadine triacetate+Tx, ipconazole+Tx, iprobenfos+Tx, iprodione+Tx, iprovalicarb (SZX0722)+Tx, isopropanyl butyl carbamate+Tx, isoprothiolane+Tx, isopyrazam+Tx, kasugamycin+Tx, kresoxim-methyl+Tx, LY186054+Tx, LY211795+Tx, LY248908+Tx, mancozeb+Tx, mandipropamid+Tx, maneb+Tx, mefenoxam+Tx, metalaxyl+Tx, mepanipyrim+Tx, mepronil+Tx, metalaxyl+Tx, metconazole+Tx, metiram+Tx, metiram-zinc+Tx, metominostrobin+Tx, myclobutanil+Tx, neoasozin+Tx, nickel dimethyldithiocarbamate+Tx, nitrothal-isopropyl+Tx, nuarimol+Tx, ofurace+Tx, organomercury compounds, +Tx oxadixyl+Tx, oxasulfuron+Tx, oxolinic acid+Tx, oxpoconazole+Tx, oxycarboxin+Tx, pefurazoate+Tx, penconazole+Tx, pencycuron+Tx, penflufen+Tx, penthiopyrad+Tx, phenazin oxide+Tx, phosetyl-Al+Tx, phosphorus acids+Tx, phthalide+Tx, picoxystrobin (ZA1963)+Tx, polyoxinD+Tx, polyram+Tx, probenazole+Tx, prochloraz+Tx, procymidone+Tx, propamocarb+Tx, propiconazole+Tx, propineb+Tx, propionic acid+Tx, prothioconazole+Tx, pyrazophos+Tx, pyrifenox+Tx, pyrimethanil+Tx, pyraclostrobin+Tx, pyroquilon+Tx, pyroxyfur+Tx, pyrroInitrin+Tx, quaternary ammonium compounds+Tx, quinomethionate+Tx, quinoxyfen+Tx, quintozene+Tx, sedaxane+Tx, sipconazole (F-155)+Tx, sodium pentachlorophenate+Tx, spiroxamine+Tx, streptomycin+Tx, sulfur+Tx, tebuconazole+Tx, tecloftalam+Tx, tecnazene+Tx, tetraconazole+Tx, thiabendazole+Tx, thifluzamid+Tx, 2-(thiocyanomethylthio)benzothiazole+Tx, thiophanate-methyl+Tx, thiram+Tx, timibenconazole+Tx, tolclofos-methyl+Tx, tolylfluanid+Tx, triadimefon+Tx, triadimenol+Tx, triazbutil+Tx, triazoxide+Tx, tricyclazole+Tx, tridemorph+Tx, trifloxystrobin (CGA279202)+Tx, triforine+Tx, triflumizole+Tx, triticonazole+Tx, validamycin A+Tx, vapam+Tx, vinclozolin+Tx, zineb+Tx and ziram+Tx, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1]+Tx, 1-methyl-3-difluoromethyl-1H-pyrazole-4-carboxylic acid (2-dichloromethylene-3-ethyl-1-methyl-indan-4-yl)-amide+Tx, and 1-methyl-3-difluoromethyl-4H-pyrazole-4-carboxylic acid [2-(2,4-dichloro-phenyl)-2-methoxy-1-methyl-ethyl]-amide+Tx.

The active ingredients combinations described above comprising a compound selected of the invention, in particularly from Tables 1P to 90P and 1Q to 36Q and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

In addition, biological agents may be included in the composition of the invention e.g. *Bacillus* species such as *Bacillus firmus*+Tx, *Bacillus cereus*+Tx, *Bacillus subtilis*+Tx, and *Pasteuria* species such as *Pasteuria penetrans*+Tx and *Pasteuria nishizawae*+Tx. A suitable *Bacillus firmus* strain is strain CNCM 1-1582 which is commercially available as BioNem™. A suitable *Bacillus cereus* strain is strain CNCM 1-1562. Of both *Bacillus* strains more details can be found in U.S. Pat. No. 6,406,690. Other biological organisms that may be included in the compositions of the invention are bacteria such as *Streptomyces* spp. such as *S. avermitilis*, and fungi such as *Pochonia* spp. such as *P. chlamydosporia*+Tx. Also of interest are *Metarhizium* spp. such as *M. anisopliae*+Tx; *Pochonia* spp. such as *P. chlamydosporia*+Tx.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment. In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-5-methyl, demeton-5-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, Buprofezine pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, *kurstaki*, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I), and in particular a compound selected from Tables 1P to 90P and 1Q to 36Q, which may result in a synergistic combination with the given active ingredient): imidacloprid+Tx, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, fipronil+Tx, ivermectin+Tx, omeprazole+Tx, tiamulin+Tx, benazepril+Tx, milbemycin+Tx, cyromazine+Tx, thiamethoxam+Tx, pyriprole+Tx, deltamethrin+Tx, cefquinome+Tx, florfenicol+Tx, buserelin+Tx, cefovecin+Tx, tulathromycin+Tx, ceftiour+Tx, selamectin+Tx, carprofen+Tx, metaflumizone+Tx, moxidectin+Tx, methoprene (including S-methoprene)+Tx, clorsulon+Tx, pyrantel+Tx, amitraz+Tx, triclabendazole+Tx, avermectin+Tx, abamectin+Tx, emamectin+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, fipronil+Tx, lufenuron+Tx, ecdysone+Tx or tebufenozide+Tx; more preferably, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx, pyrantel+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, lufenuron+Tx or ecdysone+Tx; even more preferably enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx or pyrantel+Tx.

Examples of ratios of compounds of formula I to mixing partner include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms.

Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool), cultured fish, honeybees. By combating parasites, fatalities and performance reduction (in terms of meat, milk, wool, skins, eggs, etc.) are reduced, so that applying the compounds of the invention allows more economic and simple husbandry of animals.

By controlling these pests it is intended to reduce deaths and improve performance (in the case of meat, milk, wool, hides, eggs, honey and the like) and health of the host animal. Also, controlling parasites may help to prevent the transmittance of infectious agents, the term "controlling" referring to the veterinary field, meaning that the active compounds are effective in reducing the incidence of the respective parasite in an animal infected with such parasites to innocuous levels, e.g. the active compound is effective in killing the respective parasite, inhibiting its growth, or inhibiting its proliferation.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc. and protozoae, such as coccidia).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals.

Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, ($6^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites, e.g. insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like. These include e.g. flies such as *Haematobia* (Lyperosia) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Examples of species of animal health pesets include those from the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus*; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*; from the order of the Heteropterida, for example *Cimex* spp., *Triatoma* spp., *Rhodnius* spp., *Panstrongylus* spp; from the order of the Blattarida, for example *Blatta orientalis, Periplaneta americana, Blattela germanica, Supella* spp.

(e.g. *Suppella longipalpa*); from the subclass of the *Acari* (*Acarina*) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi; Gasterophilus* spp., *Stomoxys* spp., *Trichodectes* spp., *Rhodnius* spp., *Ctenocephalides canis, Cimx lecturius, Ctenocephalides felis, Lucilia cuprina*; examples of *acari* include *Ornithodoros* spp., *Ixodes* spp., *Boophilus* spp.

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration; or by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection. The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates.

Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

It has now been found, surprisingly, that the animal health active ingredient mixtures according to the invention not only delivers about the additive enhancement of the spectrum of action with respect to the pest to be controlled that was in principle to be expected but achieves a synergistic effect which can extend the range of action of the component A and of the component B in two ways. Firstly, the rates of application of the component A and of the component B are lowered whilst the action remains equally good. Secondly, the active ingredient mixture still achieves a high degree of pest control, sometimes even where the two individual components have become totally ineffective in such a low application rate range. This allows increased safety in use.

This synergistic effect applies in particular to mixtures where component A is a compound of formula I, in particular the compounds listed in Tables 1P to 90P, and component B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide. More preferably, component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone. Even more preferably, component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

The following Examples illustrate, but do not limit, the invention. Documents referred to herein are incorporated by reference.

EXPERIMENTAL PROCEDURES

Preparation of 4 thietane-3-carbonitrile

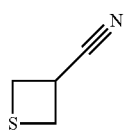

To a solution of epithiochlorohydrine (2.7 g) in benzene (10 ml) was added at room temperature a solution of potassium cyanide (4 g) in water (10 ml). The resulting mixture was heated to 50° C. for 12 hours. The mixture was extracted with benzene then the organic phase was washed with aqueous saturated sodium hydrogenocarbonate solution then water and brine. The organic phase was dried with sodium sulphate then the solvent was evaporated to dryness to give the crude residue as a yellow oil (1.76 g). 1 g of the crude was purified by a flash chromatography to obtain the title product as a brown solid (0.5 g). $^1$H-NMR (CDCl$_3$, 400 MHz): 3.25-3.35 (m, 2H), 3.65-3.75 (m, 2H), 4.10-4.25 (m, 1H). $^1$H-NMR (CDCl$_3$, 100 MHz) 27.3 (1C), 28.7 (2C), 119.7 (1C). GCMS (Method C): rt=5.07 min (87%) m/z: [M-CN]$^+$=73; [M+1]$^+$=100.

Preparation of 4 thietane-3-carbonitrile

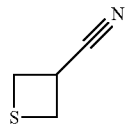

To a solution of epithiochlorohydrine (5.4 g) in tetrahydrofuran (20 ml) was added at room temperature a solution of potassium cyanide (4.9 g) in water (20 ml). The resulting mixture was heated to 50° C. for 12 hr. The mixture was extracted with tetrahydrofuran then the organic phase was washed with aqueous saturated sodium hydrogenocarbonate solution then water and brine. The organic phase was dried with sodium sulphate then the solvent was evaporated to dryness to give the crude title product as a violet oil (3.75 g), which was analysed by NMR and GCMS and contained ca 10% of 2-aminothiophene.

Preparation of thietan-3-ylmethanamine

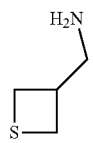

To a solution of lithium aluminium hydride (540 mg) in diethyl ether (30 ml) was added in a suspension of thietane-3-carbonitrile (1.4 g) in diethyl ether (30 ml) at 0° C. then the mixture was stirred at room temperature for 30 min. The mixture was then diluted with ether (50 ml), cooled to 0° C. then water (0.55 ml), 15% aqueous sodium hydroxide (0.55 ml) and water (1.60 ml) were added. The mixture was allowed to warm to room temperature and stirred for 15 min Anhydrous magnesium sulphate was added and stirring was continued for 15 min, then the suspension was filtered on a celite pad. The solvent was evaporated to dryness to give the crude title product as an oil (980 mg). $^1$H-NMR (CDCl$_3$, 400 MHz): 3.21 (m, 3H); 3.00 (m, 2H); 2.86 (m, 2H).

Preparation of 2-(thietan-3-ylidene)acetonitrile

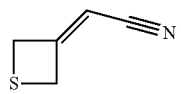

To a solution of thietan-3-one (900 mg) in 10 ml of dry methylene chloride was added a solution of (triphenylphosphoranylidene)acetonitrile (3.31 g) in 20 ml of dry methylene chloride at 0° C. The solution was allowed to warm to room temperature and after stirring for 15 min the solvent was removed under reduced pressure. The residue was purified by a flash chromatography (silica gel: Dichloromethane as an eluant) to give the title compound (785 mg) as a yellow-brown oil. GC/MS (Method C): rt=2.89 min (54.7%) m/z: [M+1]⁺=112. ¹H-NMR (CDCl₃, 400 MHz): 5.11 (m, 1H), 4.15 (m, 2H), 4.03 (m, 2H).

Preparation of 2-(thietan-3-yl)acetonitrile

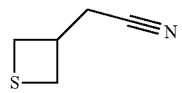

To a stirred solution of 2-(thietan-3-ylidene)acetonitrile (2.775 g) in dry methanol (250 mL), cooled to 0° C., was added sodium borohydride (9.250 g) in small portions over 30 min. The reaction mixture was allowed to warm to room temperature and stirred for a further hour.

The solvent was removed under reduced pressure. The purple residue was dissolved in ethyl acetate (50 ml) and extracted with saturated sodium hydrogenocarbonate (2×50 ml). The organic layer, dried over sodium sulphate, filtered and the solvent was removed under reduced pressure to yield a oil yellow. The residue was purified by a flash chromatography (silica gel: cyclohexane/ethyl acetate as an eluant) to give the title compound (2.2 g) as a yellow oil. GC/MS (Method C): rt=5.99 min (100%) m/z: [M+1]⁺=114. ¹H-NMR (CDCl₃, 400 MHz): 3.56 (m, 1H), 3.35 (dd, 2H), 3.09 (dd, 2H), 2.55 (d, 2H).

Preparation of 2-(thietan-3-yl)ethanamine

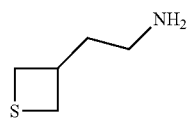

To a solution of lithium aluminium hydride (76 mg) in diethyl ether (4 ml) was added in a suspension of 2-(thietan-3-yl)acetonitrile (226 mg) in diethyl ether (30 ml) at 0° C. then the mixture was stirred at room temperature until the end of the gas evolution. The mixture was then diluted with ether (6 ml), cooled to 0° C. then water (0.08 ml), 15% aqueous sodium hydroxide (0.08 ml) and water (0.25 ml) were added. The mixture was allowed to warm to room temperature and stirred for 15 min. Anhydrous magnesium sulphate was added and stirring was continued for 15 min, then the suspension was filtered on a celite pad. The solvent was evaporated to dryness to give the crude title product as a brown oil (196 mg). ¹H-NMR (CDCl₃, 400 MHz): 3.4-3.35 (m, 1H); 3.20-3.10 (2H); 3.1-3.0 (m, 2H); 2.6 (m, 2H). GC/MS (Method C): rt=5.80 min (90%) m/z: [M+1]⁺=118.

Preparation of 4-tert-Butoxycarbonylamino-3-hydroxy-butyric acid

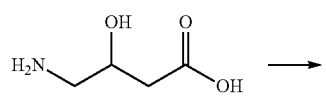

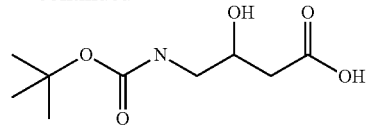

To a solution of 4-amino-3-hydroxybutyric acid (1.9 g) in aqueous 1M sodium hydroxide (35 ml) di-tert-butyl dicarbonate dissolve in dioxane (10 ml) was added drop wise. The reaction mixture was stirred at ambient temperature for 72 hours. Dioxane was evaporated and the pH was adjusted to 2-3 by adding 1M hydrochloric acid. The mixture was extracted three times with ethyl acetate. The organic phases were combined, dried over anhydrous sodium sulfate and concentrated. The residue was purified over silica gel (ethyl acetate/methanol 1:1) to give 4-tert-butoxycarbonylamino-3-hydroxy-butyric acid (3.42 g).

¹H-NMR (CDCl₃, 400 MHz): 5.05 (s, 1H), 4.07 (s, 1H), 3.28 (m, 1H), 3.10 (s, 1H), 2.48 (m, 2H), 1.40 (s, 9H).

Preparation of (2,4-Dihydroxy-butyl)-carbamic acid tert-butyl ester

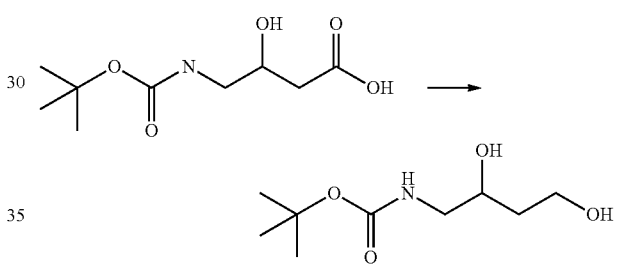

To a borane tetrahydrofuran complex solution 1M in tetrahydrofuran (15 ml) was added at 0° C. under an atmosphere of argon a solution of 4-tert-butoxycarbonylamino-3-hydroxy-butyric acid (1.5 g) in tetrahydrofuran (35 ml). The reaction mixture was stirred at 0° C. for 3 hours. The reaction was quenched by drop wise addition of 10% acetic acid in methanol (30 ml). Ethyl acetate was added (250 ml) and the mixture was washed with 1M hydrochloric acid (60 ml) and 1M sodium hydrogenocarbonate (80 ml). The organic phase was dried over anhydrous sodium sulfate and concentrated. The residue was purified over silica gel (ethyl acetate/methanol 9:1) to give (2,4-dihydroxy-butyl)-carbamic acid tert-butyl ester (0.83 g).

¹H-NMR (CDCl₃, 400 MHz): 5.02 (s, 1H), 3.95 (s, 1H), 3.88 (m, 2H), 3.25 (m, 1H), 3.15 (m, 1H), 1.70 (m, 2H), 1.45 (s, 9H).

Preparation of Methanesulfonic acid 1-(tert-butoxycarbonylamino-methyl)-3-methanesulfonyloxy-propyl ester

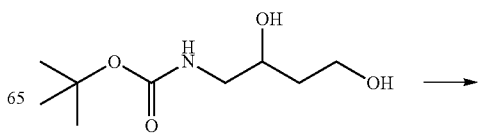

-continued

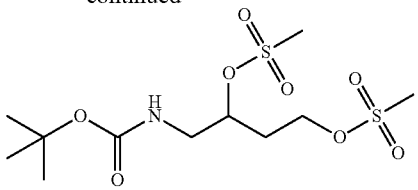

To a solution of (2,4-Dihydroxy-butyl)-carbamic acid tert-butyl ester in dichloromethane (15 ml) was added triethylamine (1.96 ml). The reaction mixture was cooled to 0° C. and methanesulfonyl chloride (0.82 ml) was added drop wise. The mixture was stirred at 0° C. for 2 hours. The mixture was filtered and dichloromethane was added (200 ml). The mixture was washed with 0.2M hydrochloric acid (50 ml), water (30 ml) and 0.2M sodium carbonate (50 ml). The organic phase was dried over anhydrous sodium sulfate and concentrated to give crude methanesulfonic acid 1-(tert-butoxycarbonylamino-methyl)-3-methanesulfonyloxy-propyl ester (1.24 g) which was used in the next step without further purification.

$^1$H-NMR (CDCl$_3$, 400 MHz): 4.95 (m, 1H), 3.85 (m, 2H), 3.95 (m, 2H), 3.10 (m, 6H), 2.15 (m, 2H), 1.45 (s, 9H).

Preparation of Thietan-2-ylmethyl-carbamic acid tert-butyl ester

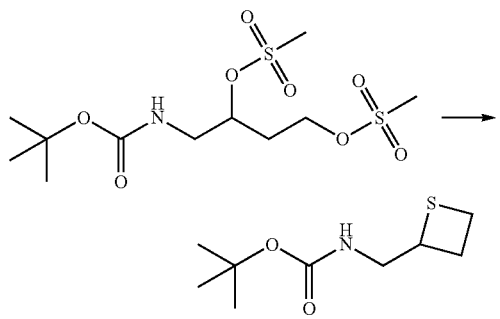

To a solution of crude methanesulfonic acid 1-(tert-butoxycarbonylamino-methyl)-3-methanesulfonyloxy-propyl ester (1.24 g) in methanol (25 ml) was added sodium sulfide monohydrate (0.84 g). The reaction mixture was stirred at 40° C. for 3 hours. The methanol was partially removed by distillation. Water was added and the mixture was extracted three times with ethyl acetate. The organic phases were combined, dried over anhydrous sodium sulfate and concentrated. The residue was purified over silica gel (ethyl acetate/heptanes, from 1:4 to 1:1) to give thietan-2-ylmethyl-carbamic acid tert-butyl ester (0.15 g).

$^1$H-NMR (CDCl$_3$, 400 MHz): 4.95 (s, 1H), 3.70 (m, 1H), 3.40 (m, 2H), 3.15 (m, 1H), 3.05 (m, 1H), 2.95 (m, 1H), 2.60 (m, 1H), 1.45 (s, 9H).

Preparation of Thietan-2-yl-methylamine hydrochloride

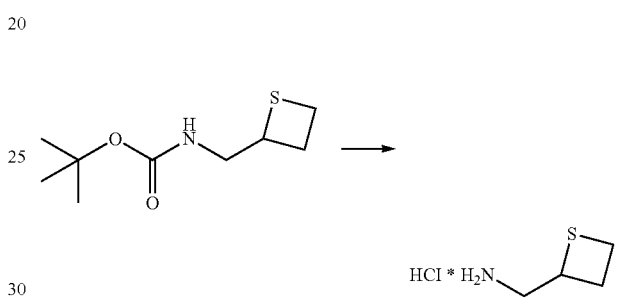

To a solution of thietan-2-ylmethyl-carbamic acid tert-butyl ester (2 g) in diethyl ether (20 ml) was added 2M hydrochloric acid in diethyl ether (24.5 ml) at 0° C. The reaction mixture was allowed to warm to ambient and stirred for 72 hours. The diethyl ether was removed by distillation. The residue was washed with hexane and filtered to give thietan-2-yl-methylamine hydrochloride (1.11 g).

$^1$H-NMR (D$_2$O, 400 MHz): 4.95 (m, 1H), 3.35 (m, 2H), 3.25-3.05 (m, 3H), 2.65 (m, 1H).

General Method BOP T° C. For Preparing the Compounds of the Invention in Parallel

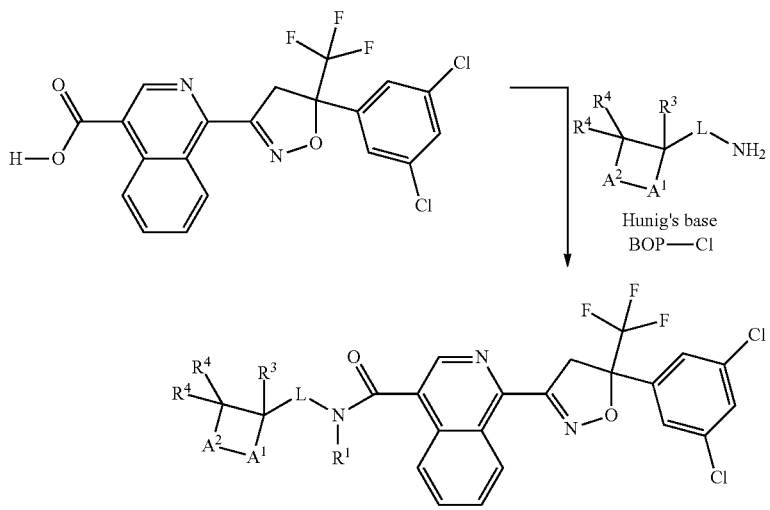

This general method was used to prepare a number of compounds in parallel.

To a solution of the appropriate carboxylic acid (30 µmol), for example 1-[5-(3,5-dichlorophenyl)-5-(trifluoromethyl)-4H-isoxazol-3-yl]isoquinoline-4-carboxylic acid for Compound D14 of Table D, in N,N-dimethylacetamide ("DMA") (0.4 ml) was added a solution of the appropriate amine (36 µmol), for example 3-methyl-thietan-3-ylamine (made as described in WO 2007/080131) for Compound D14 of Table D, in N,N-dimethylacetamide (0.145 ml) followed by diisopropylethylamine (Hunig's base) (0.04 ml, 60 µmol) and a solution of bis(2-oxo-3-oxazolidinyl)phosphonic chloride ("BOP-Cl") (15.3 mg) in N,N-dimethylacetamide (0.2 ml). The reaction mixture was stirred for 16 hours at T° C. Then the mixture was diluted with acetonitrile (0.6 ml) and a sample was used for the LC-MS analysis. The remaining mixture was further diluted with acetonitrile/N,N-dimethylformamide (4:1) (0.8 ml) and purified by HPLC to give the desired compound.

LC/MS Methods:

Method A:

ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation
Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY UPLC with the following HPLC gradient conditions
(Solvent A: Water/Methanol 9:1, 0.1% formic acid and Solvent B: Acetonitrile, 0.1% formic acid)
Type of column: Waters ACQUITY UPLC HSS T3; Column length: 30 mm; Internal diameter of column: 2.1 mm; Particle Size: 1.8 micron; Temperature: 60° C.

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3 | 100 | 0 | 0.75 |

Method B:

ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da.

1100er Series HPLC from Agilent: quaternary pump, heated column compartment and diode-array detector.
Column: Waters Atlantis dc18; length: 20 mm; internal diameter: 3 mm; particle size: 3 µm, temperature (° C.) 40, DAD wavelength range (nm): 200 to 500, solvent gradient: A=0.1% of formic acid in water and B: 0.1% of formic acid in acetonitrile.

| Time (minutes) | A (%) | B (%) | Flow rate (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method C:

ZMD Mass Spectrometer from Waters (Single quadrupole mass spectrometer)
Ionisation method: Electrospray
Polarity: positive ions
Capillary (kV) 3.00, Cone (V) 30.00, Extractor (V) 3.00, Source Temperature (° C.) 150, Desolvation Temperature (° C.) 320, Cone Gas Flow (L/Hr) 50, Desolvation Gas Flow (L/Hr) 400
Mass range: 150 to 800 Da
Column: Waters Atlantis dc18; length: 20 mm; internal diameter: 3 mm; particle size: 3 µm, temperature (° C.) 40, DAD wavelength range (nm): 200 to 500,
Waters Alliance 2795 LC with the following HPLC gradient conditions (Solvent A: 0.1% of formic acid in water and Solvent B: 0.1% of formic acid in acetonitrile)

| Time (minutes) | A (%) | B (%) | Flow rate (ml/min) |
|---|---|---|---|
| 0 | 80 | 20 | 1.7 |
| 5 | 0 | 100 | 1.7 |
| 5.6 | 0 | 100 | 1.7 |
| 6 | 80 | 20 | 1.7 |

Method D:

ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da.

1100er Series HPLC from Agilent: quaternary pump, heated column compartment and diode-array detector.
Column: Waters Atlantis dc18; length: 20 mm; internal diameter: 3 mm; particle size: 3 µm, temperature (° C.) 40, DAD wavelength range (nm): 200 to 500, solvent gradient: A=0.1% of formic acid in water and B: 0.1% of formic acid in acetonitrile.

| Time (minutes) | A (%) | B (%) | Flow rate (ml/min) |
|---|---|---|---|
| 0 | 80 | 20 | 1.7 |
| 2.5 | 0 | 100 | 1.7 |
| 2.8 | 0 | 100 | 1.7 |
| 2.9 | 80 | 20 | 1.7 |

Method E:

ZMD Mass Spectrometer from Waters (Single quadrupole mass spectrometer)
Ionisation Method: Electrospray
Polarity: positive ions
Capillary (kV) 3.00, Cone (V) 30.00, Extractor (V) 3.00, Source Temperature (° C.) 150, Desolvation Temperature (° C.) 320, Cone Gas Flow (L/Hr) 50, Desolvation Gas Flow (L/Hr) 400
Mass range: 150 to 800 Da
Column: Waters Atlantis dc18; length: 20 mm; internal diameter: 3 mm; particle size: 3 µm, temperature (° C.) 40, DAD wavelength range (nm): 200 to 500, Waters Alliance 2795 LC with the following HPLC gradient conditions (Solvent A: 0.1% of formic acid in water and Solvent B: 0.1% of formic acid in acetonitrile)

| Time (minutes) | A (%) | B (%) | Flow rate (ml/min) |
|---|---|---|---|
| 0 | 80 | 20 | 1.7 |
| 2.5 | 0 | 100 | 1.7 |
| 2.8 | 0 | 100 | 1.7 |
| 2.9 | 80 | 20 | 1.7 |

Method e:
ZQ Mass Spectrometer from Waters (Single quadrupole mass spectrometer)
Instrument Parameter:
Ionisation method: Electrospray
Polarity: positive ions
Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400
Mass range: 150 to 1000 Da
HP 1100 HPLC from Agilent: solvent degasser, quaternary pump (ZCQ)/binary pump (ZDQ), heated column compartment and diode-array detector.
Column: Phenomenex Gemini C18, 3 □m, 30×3 mm,
Temp: 60° C.
DAD Wavelength range (nm): 200 to 500
Solvent Gradient:
A=water+0.05% HCOOH
B=Acetonitril/Methanol (4:1, v:v)+0.04% HCOOH

| Time | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method i:
ZQ Mass Spectrometer from Waters (Single quadrupole mass spectrometer)
Instrument Parameter:
Ionisation method: Electrospray
Capillary (kV) 3.00, Cone (V) 30.00 45V, Extractor (V) 2.00, Source Temperature (° C.) 100, Desolvation Temperature (° C.) 250, Cone Gas Flow (L/Hr) 50, Desolvation Gas Flow (L/Hr) 400
Mass range: 100 to 900 Da (LC8 apolar: 150-1000 Da)
HP 1100 HPLC from Agilent: solvent degasser, quaternary pump (ZCQ)/binary pump (ZDQ), heated column compartment and diode-array detector.
Column: Phenomenex Gemini C18, 3 □m, 30×3 mm,
Temp: 60° C.
DAD Wavelength range (nm): 200 to 500
Solvent Gradient:
A=water+0.05% HCOOH
B=Acetonitril/Methanol (4:1, v:v)+0.04% HCOOH

| Time | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method k:
SQD Mass Spectrometer from Waters (Single quadrupole mass spectrometer)
Instrument Parameter:
Ionization method: Electrospray
Polarity: positive and negative ions
Capillary: 3.00 kV
Cone: 45.00 V
Extractor: 2.00 V
Source Temperature: 150° C.,
Desolvation Temperature: 250° C.
Cone Gas Flow: 0 L/Hr
Desolvation Gas Flow: 650 L/Hr
Mass range: 100 to 900 Da
Acquity UPLC from Waters:
Binary pump, heated column compartment and diode-array detector.
Solvent degasser, binary pump, heated column compartment and diode-array detector.
Column: Phenomenex Gemini C18, 3 □m, 30×2 mm,
Temp: 60° C.
DAD Wavelength range (nm): 210 to 500
Solvent Gradient:
A=H2O+5% MeOH+0.05% HCOOH
B=Acetonitril+0.05% HCOOH

| Time | A % | B % | Flow (ml/min) |
|---|---|---|---|
| 0.00 | 100 | 0 | 0.850 |
| 1.2 | 0 | 100.0 | 0.850 |
| 1.50 | 0 | 100.0 | 0.850 |

TABLE D

Table D discloses compounds of formula (I).

| Compound number | Compound name | LC/MS Method | retention time (min) | observed mass | Preparation method |
|---|---|---|---|---|---|
| D01 | 4-[4-bromo-5-(3,5-dichlorophenyl)-5-(trifluoromethyl)-4H-isoxazol-3-yl]-N-(1,1-dioxothietan-3-yl)naphthalene-1-carboxamide | D | 2.06 | 634.64 | |
| D02 | 4-[4-bromo-5-(3,5-dichlorophenyl)-5-(trifluoromethyl)-4H-isoxazol-3-yl]-N-(3-methylthietan-3-yl)naphthalene-1-carboxamide | D | 2.35 | 616.71 | |

TABLE D-continued

Table D discloses compounds of formula (I).

| Compound number | Compound name | LC/MS Method | retention time (min) | observed mass | Preparation method |
|---|---|---|---|---|---|
| D03 | 4-[4-bromo-5-(3,5-dichlorophenyl)-5-(trifluoromethyl)-4H-isoxazol-3-yl]-N-(1-oxothietan-3-yl)naphthalene-1-carboxamide | D | 1.94 | 618.66 | |
| D04 | 4-[4-bromo-5-(3,5-dichlorophenyl)-5-(trifluoromethyl)-4H-isoxazol-3-yl]-N-(thietan-3-yl)naphthalene-1-carboxamide | D | 2.15 | 602.67 | |
| D05 | 4-[5-(3,5-dichlorophenyl)-5-(trifluoromethyl)-4H-isoxazol-3-yl]-N-[2-[(1,1-dioxothietan-3-yl)amino]-2-oxo-ethyl]naphthalene-1-carboxamide | B | 3.67 | 613.7 | BOP-Cl 100° C. |
| D06 | 4-[5-(3,5-dichlorophenyl)-5-(trifluoromethyl)-4H-isoxazol-3-yl]-N-[2-[(3-methylthietan-3-yl)amino]-2-oxo-ethyl]naphthalene-1-carboxamide | B | 3.67 | 595.7 | BOP-Cl 100° C. |
| D07 | 4-[5-(3,5-dichlorophenyl)-5-(trifluoromethyl)-4H-isoxazol-3-yl]-N-[2-oxo-2-[(1-oxothietan-3-yl)amino]ethyl]naphthalene-1-carboxamide | B | 3.13 | 597.7 | BOP-Cl 100° C. |
| D08 | 4-[5-(3,5-dichlorophenyl)-5-(trifluoromethyl)-4H-isoxazol-3-yl]-N-[2-oxo-2-(thietan-3-ylamino)ethyl]naphthalene-1-carboxamide | B | 3.56 | 581.7 | BOP-Cl 100° C. |
| D09 | 8-[5-(3,5-dichlorophenyl)-5-(trifluoromethyl)-4H-isoxazol-3-yl]-N-(1,1-dioxothietan-3-yl)quinoline-5-carboxamide | B | 3.72 | 557.97 | BOP-Cl 100° C. |
| D10 | 8-[5-(3,5-dichlorophenyl)-5-(trifluoromethyl)-4H-isoxazol-3-yl]-N-(thietan-3-yl)quinoline-5-carboxamide | B | 4.09 | 525.95 | BOP-Cl 100° C. |
| D11 | 8-[5-(3,5-dichlorophenyl)-5-(trifluoromethyl)-4H-isoxazol-3-yl]-N-(1-oxothietan-3-yl)quinoline-5-carboxamide | B | 3.46 | 541.98 | BOP-Cl 100° C. |
| D12 | 5-[5-(3,5-dichlorophenyl)-5-(trifluoromethyl)-4H-isoxazol-3-yl]-N-(thietan-3-yl)quinoline-8-carboxamide | B, * | 2.28 min | ES$^{+-}$: 526/528 (M + H) | |
| D13 | 1-[5-(3,5-dichlorophenyl)-5-(trifluoromethyl)-4H-isoxazol-3-yl]-N-(1,1-dioxothietan-3-yl)isoquinoline-4-carboxamide | A | 1.95 | 558.25 | BOP-Cl 80° C. |
| D14 | 1-[5-(3,5-dichlorophenyl)-5-(trifluoromethyl)-4H-isoxazol-3-yl]-N-(3-methylthietan-3-yl)isoquinoline-4-carboxamide | A | 2.23 | 540.28 | BOP-Cl 80° C. |
| D15 | 1-[5-(3,5-dichlorophenyl)-5-(trifluoromethyl)-4H-isoxazol-3-yl]-N-(thietan-3-yl)isoquinoline-4-carboxamide | A | 2.16 | 526.24 | BOP-Cl 80° C. |
| D16 | 1-[5-(3,5-dichlorophenyl)-5-(trifluoromethyl)-4H-isoxazol-3-yl]-N-(1-oxothietan-3-yl)isoquinoline-4-carboxamide | A | 1.86 | 542.24 | BOP-Cl 80° C. |

* NMR data as follows: $^1$H-NMR (400 MHz, CDCl$_3$, in ppm)
D12: 3.55 (m, 2H), 3.62 (m, 2H), 3.96 (d, 1H), 4.30 (d, 1H), 5.58 (m, 1H), 7.45 (s, 1H), 7.56 (s, 2H), 7.67 (dd, 1H), 10.01 (m, 1H).

Biological Examples

This Example illustrates the insecticidal and acaricidal properties of compounds of formula (I). Tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera* littoralis:

D01, D02, D03, D04, D05, D06, D07, D08, D09, D10, D11, D12, D13, D15, D16.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*:
D01, D02, D03, D04, D05, D06, D10, D11, D12, D13, D14, D15, D16.

*Plutella xylostella* (Diamond Back Moth):
24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*:
D01, D02, D03, D04, D05, D06, D07, D08, D09, D10, D11, D12, D13, D14, D15, D16.

*Diabrotica balteata* (Corn Root Worm):
A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compounds gave at least 80% control of *Diabrotica balteata*:
D01, D02, D03, D04, D05, D06, D08, D10, D12, D13, D14, D15, D16.

*Thrips tabaci* (Onion *Thrips*):
Sunflower leaf discs were placed on agar in a 24-well microtiter plate and sprayed with test solutions at an application rate of 200 ppm. After drying, the leaf discs were infested with a thrip population of mixed ages. After an incubation period of 7 days, samples were checked for mortality.

The following compounds gave at least 80% control of *Thrips tabaci*:
D01, D02, D03, D04, D05, D06, D07, D08, D12, D14, D15, D16.

*Tetranychus urticae* (Two-Spotted Spider Mite):
Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*:
D01, D02, D03, D04, D05, D06, D07, D08, D12, D14, D15, D16.

The invention claimed is:

1. A compound of formula I

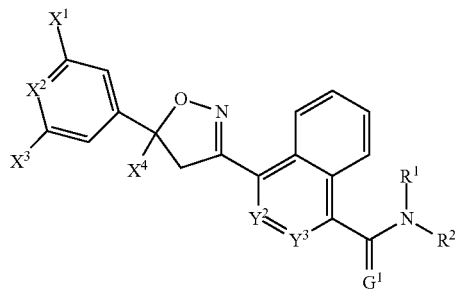

wherein
$G^1$ is oxygen;
$R^1$ is hydrogen;
$R^2$ is group P

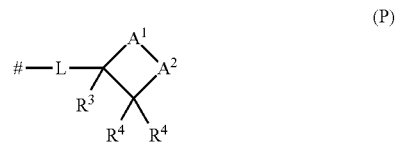

L is a bond, methylene or ethylene;
one of $A^1$ and $A^2$ is S, SO or $SO_2$ and the other is —C($R^4$)$R^4$—;
$R^3$ is hydrogen or methyl;
each $R^4$ is independently hydrogen or methyl;
$Y^2$ and $Y^3$ are independently CH or nitrogen, wherein $Y^2$ and $Y^3$ are not both nitrogen;
$X^1$ is chloro, $X^2$ is CH, $X^3$ is trifluoromethyl, or
$X^1$ is fluoro, $X^2$ is CH, $X^3$ is trifluoromethyl, or
$X^1$ is chloro, $X^2$ is C—Cl, $X^3$ is trifluoromethyl, or
$X^1$ is trifluoromethyl, $X^2$ is CH, $X^3$ is trifluoromethyl, or
$X^1$ is trifluoromethyl, $X^2$ is C—Cl, $X^3$ is trifluoromethyl, or
$X^1$ is trifluoromethyl, $X^2$ is CH, $X^3$ is hydrogen, or
$X^1$ is trifluoromethyl, $X^2$ is N, $X^3$ is trifluoromethyl,
$X^4$ is trifluoromethyl, difluoromethyl or chlorodifluoromethyl.

2. A compound according to claim 1, wherein $R^2$ is thietan-3-yl-, 1-oxo-thietan-3-yl-, 1,1-Dioxo-thietan-3-yl-, 2,2-dimethylthietan-3-yl-, 2,2-dimethyl-1-oxo-thietan-3-yl-, 2,2-dimethyl-1,1-Dioxo-thietan-3-yl-, 3-Methyl-thietan-3-yl-, 3-Methyl-1-oxo-thietan-3-yl-, 3-Methyl-1,1-Dioxo-thietan-3-yl-, thietan-3-ylmethyl-, 1-oxo-thietan-3-ylmethyl-, 1,1-Dioxo-thietan-3-ylmethyl-, thietan-2-ylmethyl-, (1-oxothietan-2-yl)methyl-, (1,1-dioxothietan-2-yl)methyl-, 2-(thietan-3-yl)ethanyl, 2-(1,1-dioxothietan-3-yl)ethanyl, or 2-(1-oxothietan-3-yl)ethanyl.

3. A compound according to claim 1, wherein
$Y^2$ is N, $Y^3$ is CH, or
$Y^2$ is N, $Y^3$ is CH, or
$Y^2$ is CH, $Y^3$ is N.

4. A compound according to claim 1, wherein $X^2$ is C—$X^6$, $Y^2$ and $Y^3$ are C—H, $R^3$ is hydrogen and each $R^4$ is hydrogen.

5. A method of controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I) as defined in claim 1.

6. An insecticidal, acaricidal, nematicidal or molluscicidal composition comprising an insecticidally, acaricidally, nematicidally or molluscicidally effective amount of a compound of formula (I) as defined in claim 1.

7. An insecticidal, acaricidal, nematicidal or molluscicidal composition according to claim 6 comprising at least one additional compound having biological activity.

8. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide, wherein the combination product is for use in a method of therapeutic treatment.

9. A combination product comprising a pesticidally effective amount of a component A and a pesticidally effective amount of component B, wherein component A is a compound of formula (I) as defined in claim 1, wherein component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone.

10. A combination product according to claim 8, wherein component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

\* \* \* \* \*